US010780020B2

(12) United States Patent
Hunt et al.

(10) Patent No.: US 10,780,020 B2
(45) Date of Patent: Sep. 22, 2020

(54) MAINTAINING ACTIVE COMPRESSION DECOMPRESSION DEVICE ADHERENCE

(71) Applicant: ZOLL Medical Corporation, Chelmsford, MA (US)

(72) Inventors: Scott Edward Hunt, Franklin, MA (US); Elangovan Ramanathan, Shrewsbury, MA (US); James R. Homuth, Corcoran, MN (US); Christopher Joseph Desmarais, Acushnet, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 405 days.

(21) Appl. No.: 15/721,101

(22) Filed: Sep. 29, 2017

(65) Prior Publication Data
US 2018/0092804 A1 Apr. 5, 2018

Related U.S. Application Data

(60) Provisional application No. 62/402,619, filed on Sep. 30, 2016.

(51) Int. Cl.
*A61H 31/00* (2006.01)
*A61N 1/04* (2006.01)
*A61N 1/39* (2006.01)

(52) U.S. Cl.
CPC .......... *A61H 31/004* (2013.01); *A61H 31/00* (2013.01); *A61H 31/005* (2013.01);
(Continued)

(58) Field of Classification Search
CPC .......... A61H 7/00; A61H 7/001; A61H 7/007; A61H 23/00; A61H 23/06;
(Continued)

(56) References Cited

U.S. PATENT DOCUMENTS 517,481 A 4/1894 Pressey
728,003 A 5/1903 Pfanshmidt et al.
(Continued)

FOREIGN PATENT DOCUMENTS

| CH | 188989 | 1/1937 |
| WO | WO8500018 | 1/1985 |
| WO | WO2009089096 | 7/2009 |

OTHER PUBLICATIONS

Yannopoulos et al., "Intrathoracic Pressure Regulation Improves 24-Hour Survival in a Porcine Model of Hypovolemic Shock." Anesthesia & Analgesia, ITPR and Survival in Hypovolemic Shock, vol. 104, No. 1, Jan. 2007, pp. 157-162.
(Continued)

*Primary Examiner* — Colin W Stuart
(74) *Attorney, Agent, or Firm* — Fish & Richardson P.C.

(57) ABSTRACT

Systems and apparatuses related to the field of cardiac resuscitation, and in particular to devices for assisting rescuers in the administration of cardio-pulmonary resuscitation (CPR) are described herein. The system includes an adhesive pad configured to be adhered to at least a portion of a patient's chest, a sensor configured to be placed on the patient's chest and to measure at least one chest compression parameter during CPR treatment, and a landing pad having a coupling surface at least partially surrounding the sensor and configured for maintaining adherence with an active compression decompression device, the adherence sufficient to transfer decompression force between the active compression decompression device and the patient's chest during the CPR treatment.

34 Claims, 31 Drawing Sheets

(52) U.S. Cl.
CPC .......... *A61H 31/007* (2013.01); *A61N 1/046* (2013.01); *A61N 1/39044* (2017.08); *A61H 2031/001* (2013.01); *A61H 2031/002* (2013.01); *A61H 2201/013* (2013.01); *A61H 2201/10* (2013.01); *A61H 2201/1619* (2013.01); *A61H 2201/5043* (2013.01); *A61H 2201/5061* (2013.01); *A61H 2201/5084* (2013.01); *A61H 2201/5097* (2013.01); *A61H 2205/084* (2013.01); *A61N 1/0492* (2013.01); *A61N 1/3993* (2013.01)

(58) Field of Classification Search
CPC ........ A61H 2023/002; A61H 2201/013; A61H 2201/1619; A61H 2201/1621; A61H 2205/084; A61H 31/00; A61H 31/004; A61H 31/005; A61H 31/006; A61H 31/007; A61H 2031/001; A61H 2031/002; A61H 2031/003; A61N 1/39044
See application file for complete search history.

(56) References Cited

U.S. PATENT DOCUMENTS

| | | | |
|---|---|---|---|
| 1,175,671 | A | 3/1916 | Ackeen |
| 1,460,927 | A | 7/1923 | Thompson et al. |
| 2,029,951 | A | 2/1936 | Smith |
| 2,067,268 | A | 1/1937 | Hans |
| 2,071,365 | A | 1/1937 | Stroop |
| 2,069,449 | A | 2/1937 | Jensen |
| 2,204,738 | A | 6/1940 | swan |
| 2,571,606 | A | 10/1951 | Peterson |
| 2,742,251 | A | 4/1956 | Udvardy |
| 2,879,765 | A | 3/1959 | Featherston |
| 3,460,182 | A | 8/1969 | Grande, Jr. |
| 3,509,899 | A | 5/1970 | Hewson |
| 3,534,733 | A | 10/1970 | Phipps et al. |
| 3,783,865 | A | 1/1974 | Ricketts |
| 3,958,564 | A | 5/1976 | Langguth |
| 4,059,099 | A | 11/1977 | Davis |
| 4,077,400 | A | 3/1978 | Harrigan |
| 4,095,590 | A | 6/1978 | Harrigan |
| 4,166,458 | A | 9/1979 | Harrigan |
| 4,196,722 | A | 4/1980 | Vanderwoude |
| 4,198,963 | A | 4/1980 | Barkalow et al. |
| 4,237,872 | A | 12/1980 | Harrigan |
| 4,273,114 | A | 6/1981 | Barkalow et al. |
| 4,429,688 | A | 2/1984 | Duffy |
| 4,513,737 | A | 4/1985 | Mabuchi |
| 4,570,615 | A * | 2/1986 | Barkalow ............ A61H 31/006 601/106 |
| 4,745,910 | A | 5/1988 | Day et al. |
| 4,747,397 | A | 5/1988 | Magovum |
| 4,809,683 | A * | 3/1989 | Hanson .................. A61H 31/00 601/107 |
| 4,852,574 | A | 8/1989 | Inoue et al. |
| 4,881,527 | A | 11/1989 | Lerman |
| 4,984,987 | A | 1/1991 | Brault et al. |
| 5,295,481 | A | 3/1994 | Geeham |
| 5,454,779 | A | 10/1995 | Lurie et al. |
| 5,551,420 | A | 9/1996 | Lurie et al. |
| 5,645,522 | A | 7/1997 | Lurie et al. |
| 5,657,751 | A | 8/1997 | Karr, Jr. |
| 5,692,498 | A | 12/1997 | Lurie et al. |
| 6,062,219 | A | 5/2000 | Lurie et al. |
| 6,155,257 | A | 12/2000 | Lurie et al. |
| 6,174,295 | B1 | 1/2001 | Cantrell et al. |
| 6,178,357 | B1 * | 1/2001 | Gliner .................... A61N 1/046 600/392 |
| 6,224,562 | B1 | 5/2001 | Lurie et al. |
| 6,234,985 | B1 | 5/2001 | Lurie et al. |
| 6,312,399 | B1 | 11/2001 | Lurie et al. |
| 6,356,785 | B1 | 3/2002 | Snyder et al. |
| 6,425,393 | B1 | 7/2002 | Lurie et al. |
| 6,463,327 | B1 | 10/2002 | Lurie et al. |
| 6,477,430 | B1 | 11/2002 | Feuersanger et al. |
| 6,533,739 | B1 | 3/2003 | Palmer et al. |
| 6,604,523 | B2 | 8/2003 | Lurie et al. |
| 6,676,613 | B2 | 1/2004 | Cantrell et al. |
| 6,863,656 | B2 | 3/2005 | Lurie |
| 6,935,336 | B2 | 8/2005 | Lurie |
| 6,938,618 | B2 | 9/2005 | Lurie et al. |
| 6,951,546 | B2 | 10/2005 | Palmer et al. |
| 6,986,349 | B2 | 1/2006 | Lurie |
| 7,044,128 | B2 | 5/2006 | Lurie et al. |
| 7,082,945 | B2 | 8/2006 | Lurie |
| 7,174,891 | B2 | 2/2007 | Lurie et al. |
| 7,185,649 | B2 | 3/2007 | Lurie |
| 7,195,012 | B2 | 3/2007 | Lurie |
| 7,195,013 | B2 | 3/2007 | Lurie |
| 7,204,251 | B2 | 4/2007 | Lurie |
| 7,210,480 | B2 | 5/2007 | Lurie et al. |
| 7,211,056 | B2 | 5/2007 | Petelenz et al. |
| 7,220,235 | B2 | 5/2007 | Geheb et al. |
| 7,226,427 | B2 | 6/2007 | Steen |
| 7,275,542 | B2 | 10/2007 | Lurie et al. |
| 7,297,125 | B2 | 11/2007 | Palmer et al. |
| 7,335,085 | B2 | 2/2008 | Lyman |
| 7,569,021 | B2 | 8/2009 | Sebelius et al. |
| 7,618,383 | B2 | 11/2009 | Palmer et al. |
| 7,682,312 | B2 | 3/2010 | Lurie |
| 7,753,845 | B2 | 7/2010 | Gopinathan et al. |
| 7,766,011 | B2 | 8/2010 | Lurie et al. |
| 7,836,881 | B2 | 11/2010 | Lurie et al. |
| 8,011,367 | B2 | 9/2011 | Lurie et al. |
| 8,151,790 | B2 | 4/2012 | Ltuie et al. |
| 8,408,204 | B2 | 4/2013 | Lurie |
| 8,535,251 | B1 | 9/2013 | Rao |
| 8,622,940 | B2 | 1/2014 | Udassi et al. |
| 8,702,633 | B2 | 4/2014 | Voss et al. |
| 8,706,214 | B2 | 4/2014 | Tan et al. |
| 8,744,573 | B2 | 6/2014 | Freeman |
| 8,936,691 | B2 | 1/2015 | Leggett |
| 9,107,800 | B2 | 8/2015 | Sebelius et al. |
| 9,119,767 | B2 | 9/2015 | Wood |
| 9,238,115 | B2 | 1/2016 | Homuth |
| 9,283,140 | B2 | 3/2016 | Freeman et al. |
| 9,302,033 | B2 | 4/2016 | Riesinger |
| 9,339,436 | B2 | 5/2016 | Freeman et al. |
| 9,352,111 | B2 | 5/2016 | Lurie et al. |
| 9,433,554 | B2 | 9/2016 | Freeman |
| 9,521,978 | B2 | 12/2016 | Freeman et al. |
| 9,545,359 | B2 | 1/2017 | Freeman et al. |
| 9,642,547 | B2 | 5/2017 | Tan et al. |
| 9,655,809 | B2 | 5/2017 | Freeman |
| 9,662,258 | B2 | 5/2017 | Slattery, Jr. |
| 9,675,770 | B2 | 6/2017 | Lurie et al. |
| 9,693,700 | B2 | 7/2017 | Tan et al. |
| 9,707,152 | B2 | 7/2017 | Lurie et al. |
| 9,713,445 | B2 | 7/2017 | Freeman et al. |
| 9,724,266 | B2 | 8/2017 | Voss et al. |
| 9,750,453 | B2 | 9/2017 | Freeman et al. |
| 9,750,661 | B2 | 9/2017 | Lurie et al. |
| 9,782,123 | B2 | 10/2017 | Freeman |
| 9,801,782 | B2 | 10/2017 | Lurie et al. |
| 9,811,634 | B2 | 11/2017 | Lurie et al. |
| 2001/0047140 | A1 | 11/2001 | Freeman |
| 2002/0069878 | A1 | 6/2002 | Lurie et al. |
| 2002/0170562 | A1 | 11/2002 | Lurie et al. |
| 2004/0016428 | A9 | 1/2004 | Lurie |
| 2004/0200474 | A1 | 10/2004 | Lurie |
| 2004/0211415 | A1 | 10/2004 | Lurie |
| 2004/0211416 | A1 | 10/2004 | Lurie |
| 2004/0211417 | A1 | 10/2004 | Lurie |
| 2004/0231664 | A1 | 11/2004 | Lurie et al. |
| 2005/0165334 | A1 | 7/2005 | Lurie |
| 2005/0199237 | A1 | 9/2005 | Lurie |
| 2005/0209543 | A1 | 9/2005 | Palmer et al. |
| 2006/0009809 | A1 * | 1/2006 | Marcovecchio ......... A61N 1/39 607/5 |
| 2006/0047228 | A1 | 3/2006 | Petelenz et al. |
| 2006/0270952 | A1 | 11/2006 | Freeman et al. |
| 2008/0039748 | A1 | 2/2008 | Palmer et al. |

(56) References Cited

U.S. PATENT DOCUMENTS

| | | |
|---|---|---|
| 2008/0071316 A1 | 3/2008 | Freeman |
| 2008/0108905 A1 | 5/2008 | Lurie |
| 2008/0171311 A1 | 7/2008 | Centen et al. |
| 2009/0062701 A1 | 3/2009 | Yannopoulos et al. |
| 2009/0260637 A1 | 10/2009 | Sebelius et al. |
| 2010/0160839 A1 | 6/2010 | Freeman et al. |
| 2010/0179442 A1 | 7/2010 | Lurie |
| 2010/0319691 A1 | 12/2010 | Lurie et al. |
| 2012/0330200 A1 | 12/2012 | Voss et al. |
| 2014/0094724 A1* | 4/2014 | Freeman .............. A61H 31/006 601/41 |

OTHER PUBLICATIONS

Yannopoulos et al., "Intrathoracic pressure regulation improves vital organ perfusion pressures in normovolemic and hypovolemic pigs," Resuscitation, 2006, 70, pp. 445-453.

* cited by examiner

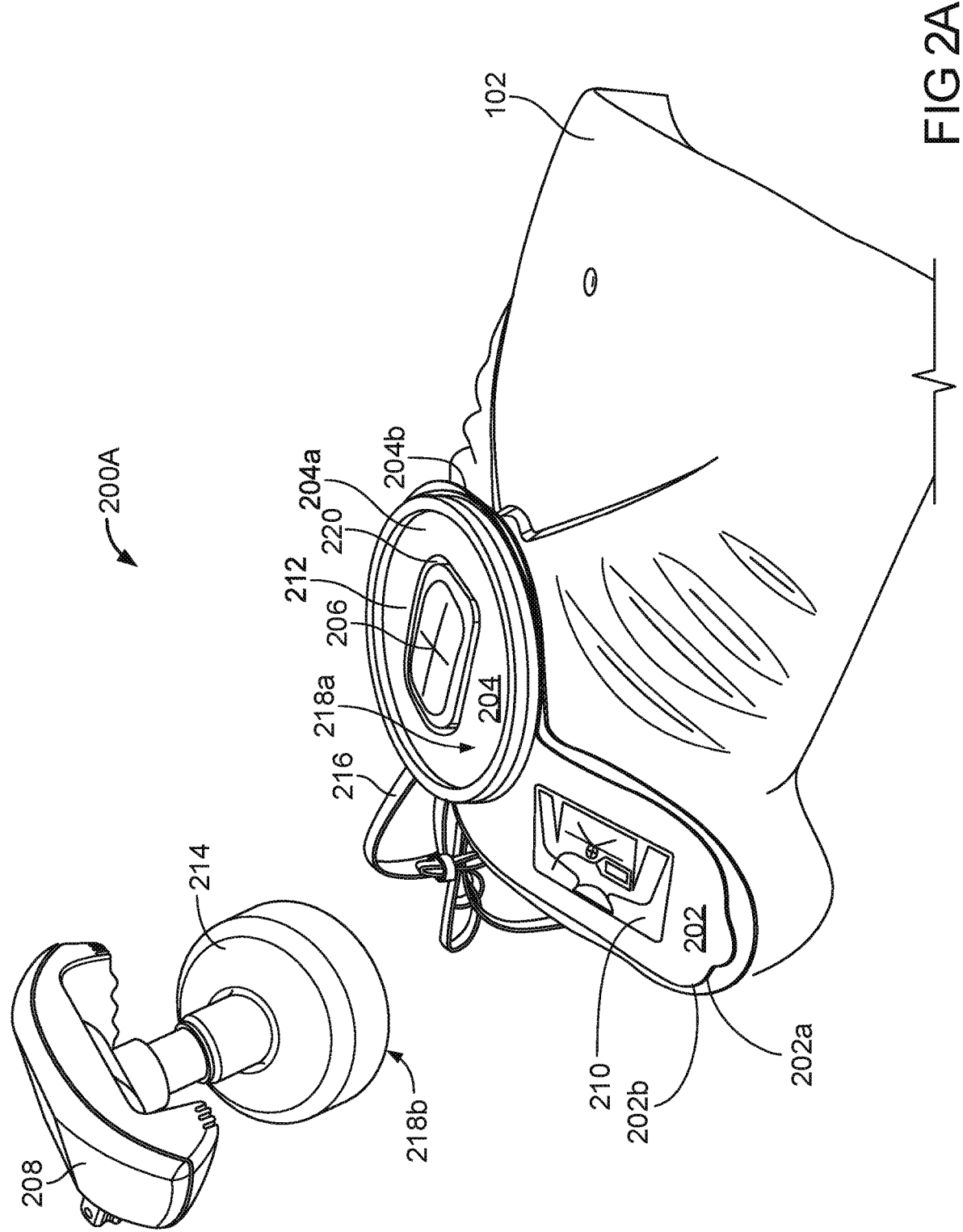

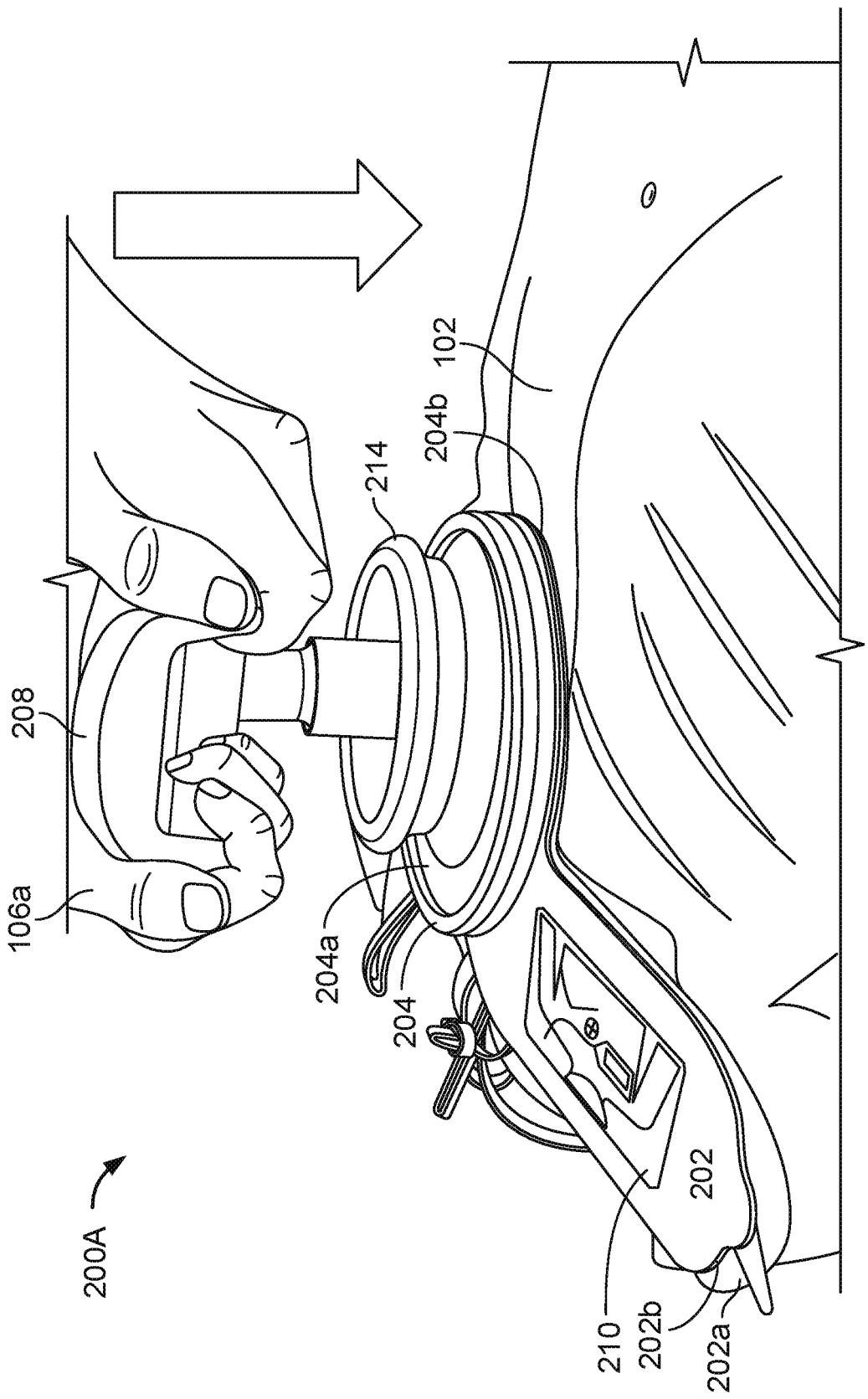

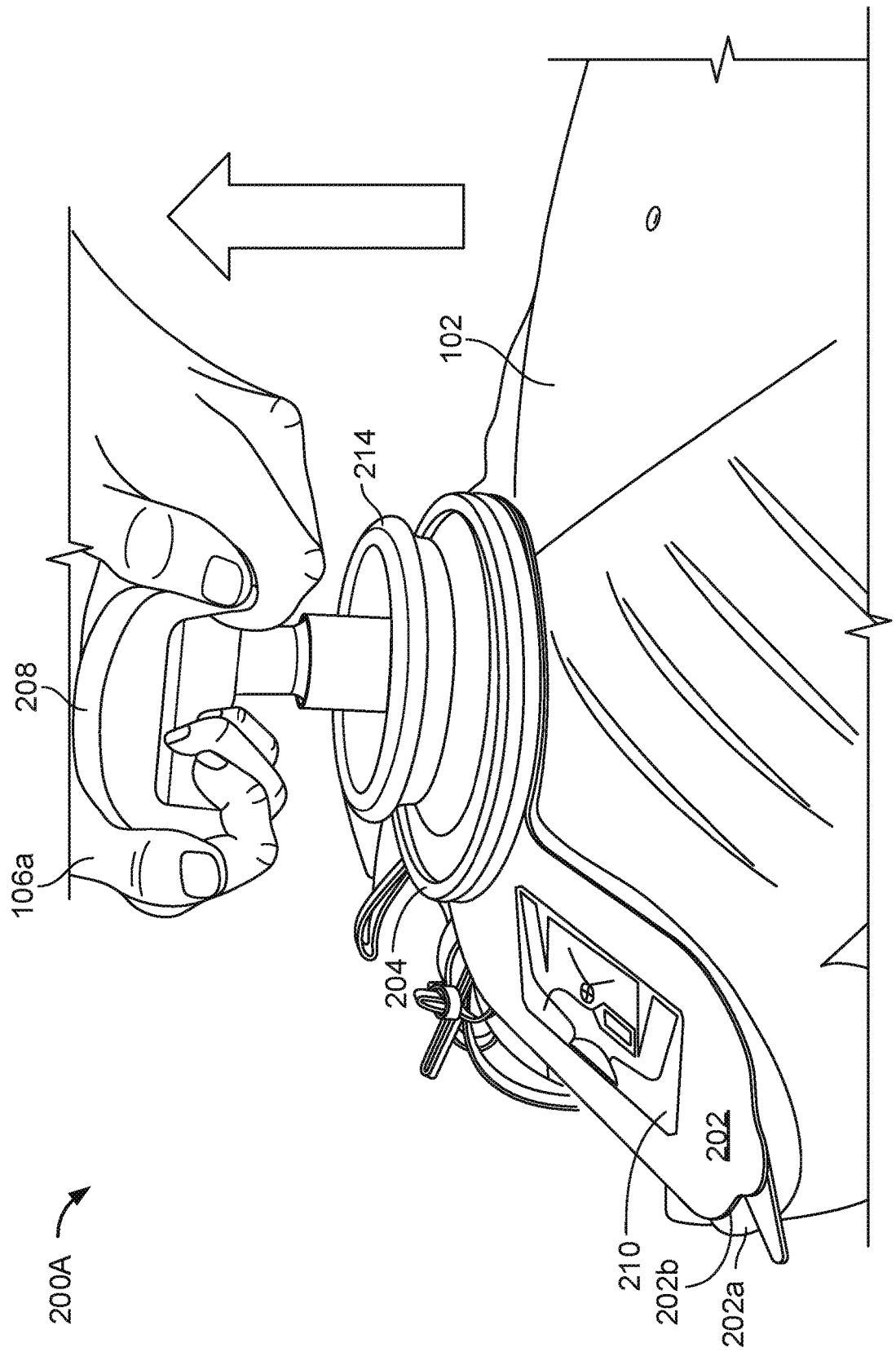

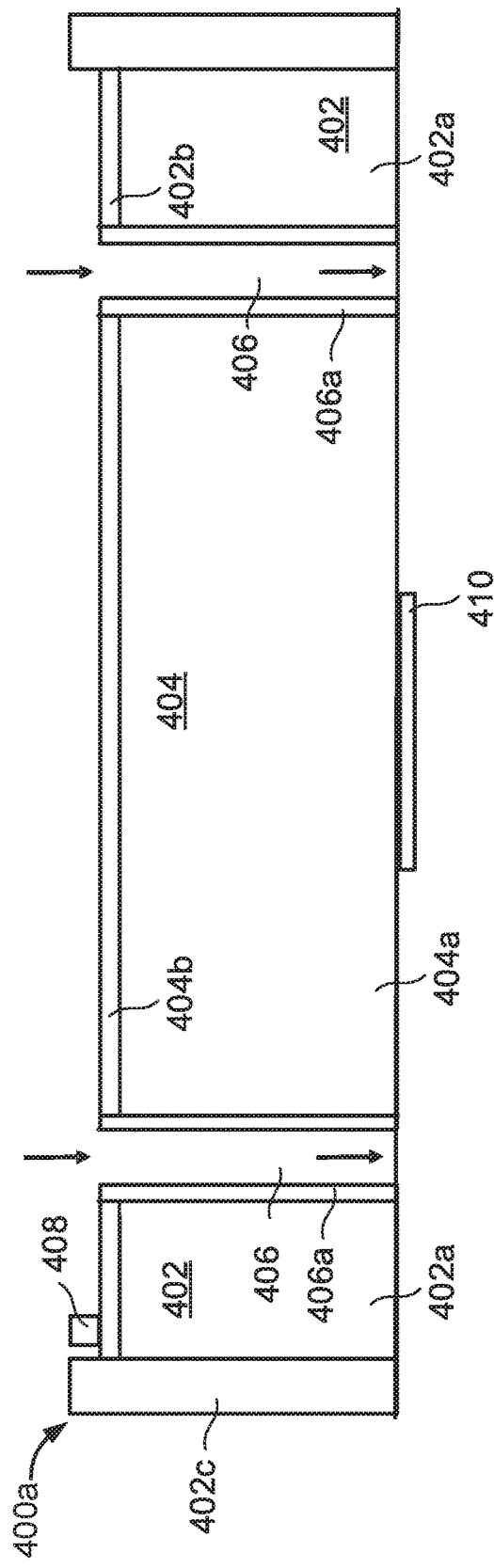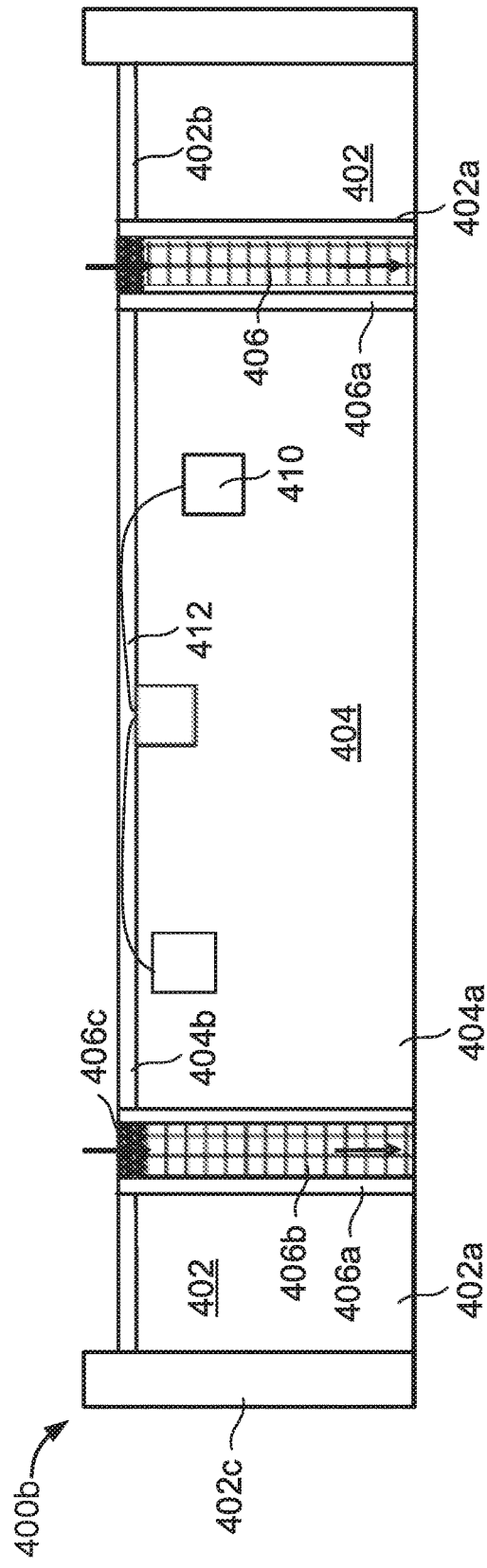

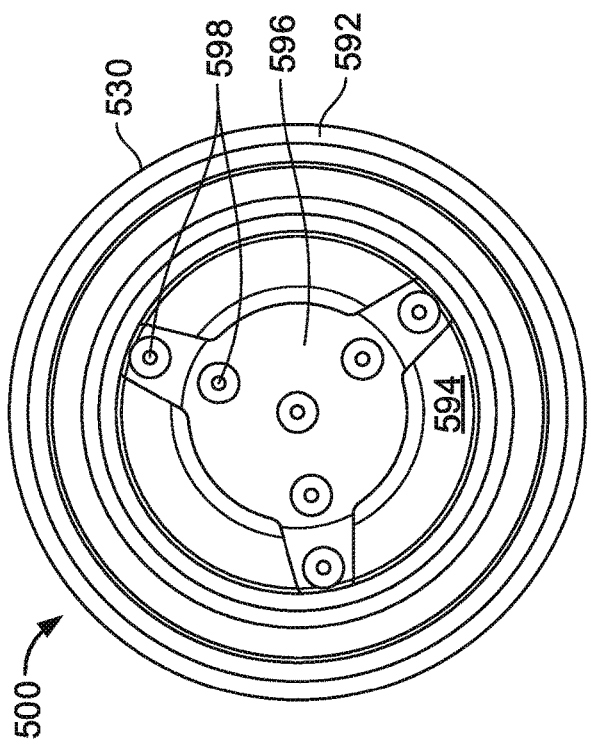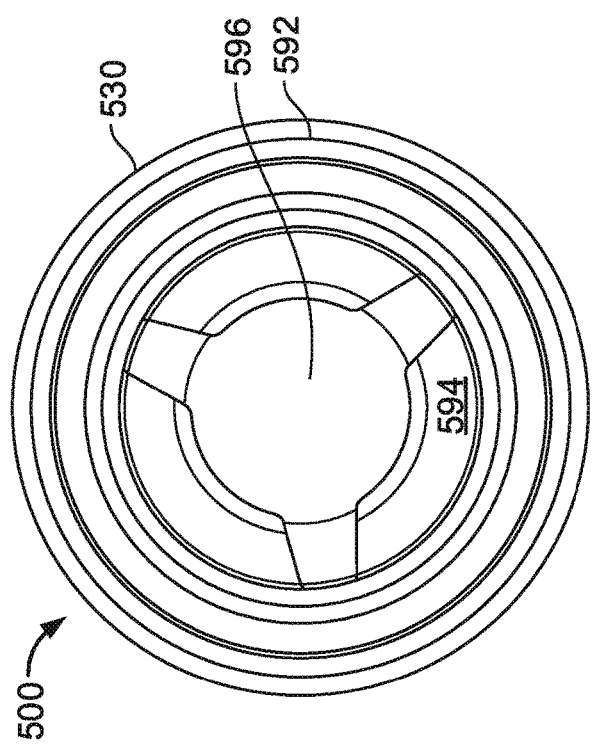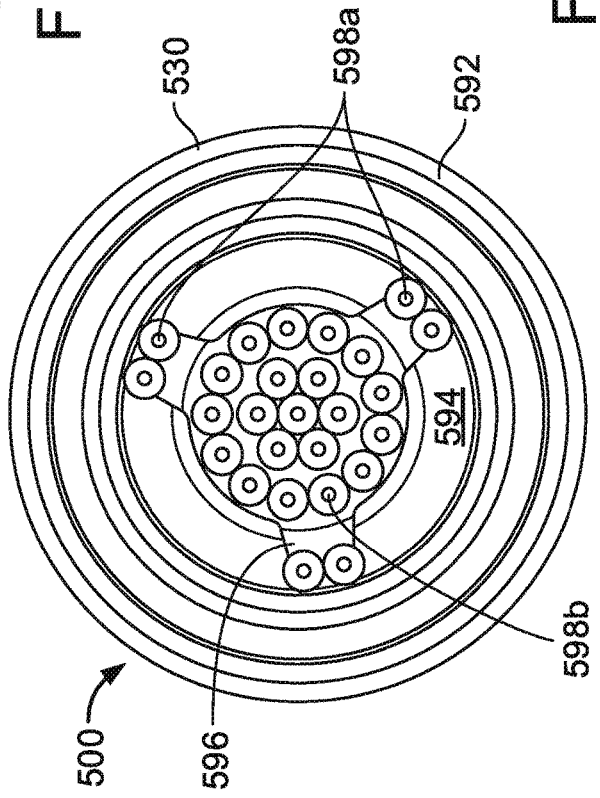

MAINTAINING ACTIVE COMPRESSION DECOMPRESSION DEVICE ADHERENCE

TECHNICAL FIELD

This document relates to cardiac resuscitation systems, and in particular, to systems for assisting rescuers in performing and optimizing cardio-pulmonary resuscitation (CPR).

BACKGROUND

CPR is a process by which one or more rescuers can provide chest compressions and ventilation to a patient who has suffered a cardiac arrest. Chest compressions are considered to be an important element of CPR during the first five to eight minutes after CPR efforts begin, because chest compressions help maintain circulation through the body, heart, and brain, which are the organs that can sustain the most damage from an adverse cardiac event. Traditional chest compressions include two phases: one, which is referred to as the "active compression phase" where the chest is compressed by the direct application of external pressure and another one, which is referred to as the "relaxation phase" and occurs when pressure is withdrawn and the natural elasticity of the patient's chest wall causes expansion. The chest expansion of the relaxation phase is generally sufficient to partially refill the cardiac chambers with blood, but it can be insufficient to ventilate the patient, by filling the lungs with air to oxygenate the blood. In conventional CPR, the air necessary for blood oxygenation is provided through periodic ventilation of the patient. Generally, American Heart Association CPR Guidelines define protocols, by which a rescuer is to apply the chest compressions in coordination with ventilations. For example, 2015 AHA Guidelines specify a ratio of 30:2 for compressions to ventilations (e.g., thirty compressions for every two breaths) and compressions are to be performed at a rate of between 100 and 120 per minute.

SUMMARY

This document describes systems and apparatuses that can be used to help manage the administration of a cardiopulmonary resuscitation (CPR) treatment to a patient in need of emergency assistance. In one implementation, a system includes an adhesive pad configured to be adhered to a portion of a patient's chest, a sensor configured to be placed on the patient's chest and to measure at least one chest compression parameter during CPR treatment. The system also includes a landing pad having a coupling surface configured to maintain adherence with an applicator body of an active compression decompression device, the adherence with the applicator body being sufficient to transfer a decompression force between the active compression decompression device and the portion of the patient's chest during the CPR treatment.

In some aspects, the adhesive pad can include an electrode configured to transmit a defibrillation current to the patient. The coupling surface may include or be part of a landing pad for the applicator body. The landing pad may include a lower portion configured to be adhered to the patient's chest and having a gel-like material that forms a seal between the patient's chest and at least one of the adhesive pad and the sensor. The sensor is coupled to the adhesive pad. The coupling surface of the landing pad at least partially surrounds the sensor.

The gel-like material comprises silicone gel. The lower portion of the landing pad includes an adhesive for adhering the landing pad to the patient's chest.

The coupling surface can include a surface that complements at least one suction cup. The coupling surface may include compliant material that is substantially smooth. The compliant material can include a foam sheet. The landing pad includes a lower portion configured to be adhered to the patient's chest, the lower portion including wings that are constructed and arranged to flex away from the coupling surface of the landing pad to maintain adherence within the patient's chest during the administration of active compression decompression. The landing pad includes an upper portion including the coupling surface for maintaining adherence with the applicator body, wherein the upper portion comprises at least one barrier extending along an outer boundary of the landing pad.

In other aspects, the system can include a wire or a cable coupled to the sensor for providing electrical connection between the sensor and a medical device. The coupling surface can cover the wire or a cable. In some implementations, the system can include a passageway located between the sensor and the coupling surface. The passageway substantially encircles the sensor. The passageway can include a gap between the sensor and the coupling surface. The passageway can include at least one filter.

In yet another aspect, the applicator body of the active compression decompression device can surround the passageway upon adherence between the coupling surface and the active compression decompression device. The passageway can have one of multiple geometrical shapes, such as a substantially donut shape or a substantially oval shape. The passageway (e.g., the geometrical center of the passageway) can be aligned with a geometrical center of the chest compression monitor. The coupling surface can include a mechanical attachment member complementary to a corresponding attachment member of the active compression decompression device. The mechanical attachment member can include a mating interface.

In another implementation, an apparatus for assisting active compression decompression cardiopulmonary resuscitation (CPR) treatment to a patient in need of emergency assistance may include a landing pad having an upper portion and a lower portion mechanically coupled to one another, wherein the lower portion is configured to be adhered to at least a portion of a patient's chest. The upper portion may further include a coupling surface configured to maintain adherence with an applicator body of an active compression decompression device. The adherence with the applicator body is sufficient to transfer a decompression force between the active compression decompression device and the portion of the patient's chest during the CPR treatment.

In one aspect, the coupling surface is substantially smooth and complements at least one suction cup. The coupling surface can include a compliant material. The compliant material can include a foam sheet. The upper portion of the landing pad can include at least one barrier extending along at least a portion of an outer boundary of the landing pad. The upper portion of the landing pad can include a top layer and the lower portion of the landing pad can include a bottom layer, the landing pad further including a middle layer that is more rigid than the top layer and the bottom layer. The lower portion of the landing pad can include a gel-like material that forms a seal between the patient's chest and a component located between the patient's chest and the lower portion of the landing pad when in use.

In other aspects, the gel-like material can include silicone gel. The gel-like material can extend around the perimeter of an opening located at a central region of the landing pad.

In yet another aspect, the lower portion of the landing pad has an outer boundary including recessed segments. The lower portion of the landing pad can include wings that are constructed and arranged to flex away from the upper portion of the landing pad to maintain adherence within the patient's chest during the administration of active compression decompression. The lower portion of the landing pad can include an adhesive for adhering the landing pad to the patient's chest.

Other features and advantages will be apparent from the description, from the drawings, and from the claims.

DESCRIPTION OF DRAWINGS

FIGS. 4A and 4B show cross-sectional views of example coupling surfaces configured to maintain suction adherence in accordance with certain implementations.

FIGS. 5C, 5D, and 5E show bottom views of an example active compression decompression device that maintains suction adherence.

DETAILED DESCRIPTION

Figure 1:
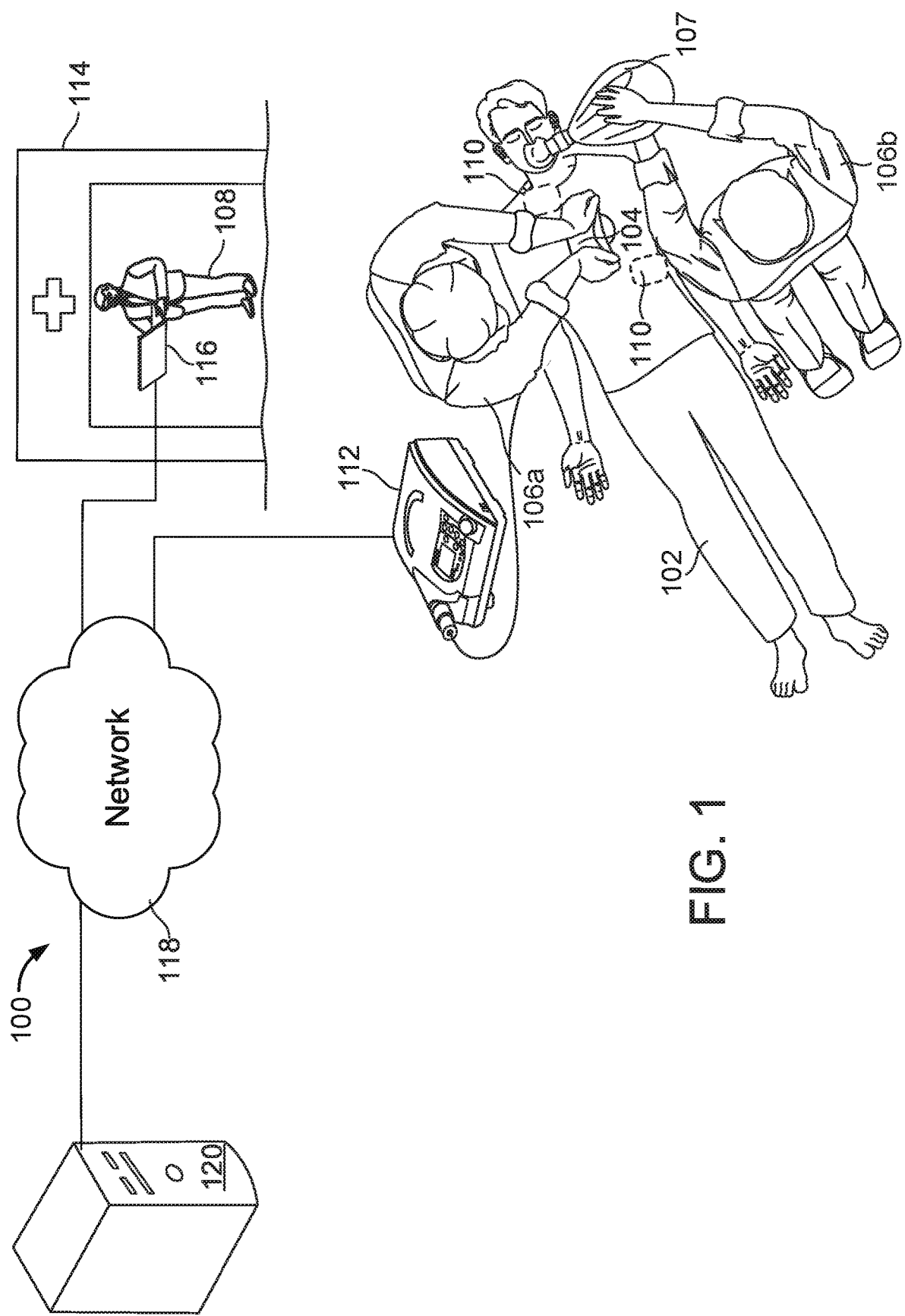
FIG. 1 shows an overhead view of rescuers providing resuscitative treatment to a patient using a CPR assistance system that maintains suction adherence.

Implementations of the present disclosure are generally directed to systems for managing a cardiopulmonary resuscitation (CPR) treatment to a patient in need of emergency assistance, such as a patient suffering of cardiac arrest. In particular, implementations of the present disclosure are generally directed to systems for assisting a rescuer to perform active compression decompression (ACD) CPR. ACD CPR differs from standard CPR chest compressions in that the patient's chest is actively pressed and lifted in an alternating manner. An exemplary device to assist in the performance of ACD CPR is the RESQPUMP® (provided by ZOLL Medical). Such devices have the ability to couple to the patient's chest to facilitate lifting of the chest during the decompression phase. By actively lifting the chest, the negative intrathoracic pressure is increased causing more venous blood to flow to the heart and lungs during the decompression phase. Thus, in addition to compression of the chest to improve blood flow from the heart to peripheral tissues of the body, decompression of the chest offered through ACD reduces intrathoracic pressure, resulting in enhanced venous return of blood from peripheral tissues back to the heart and refilling of the cardiac chambers.

In some embodiments described herein, a landing pad is provided which has a platform or coupling surface for the suction portion of an ACD device to establish and maintain adherence thereto. The landing pad has an adhesive surface on its underside (e.g., bottom layer) that adheres to the surface of the patient's chest and a coupling surface on its upper landing platform side (e.g., top layer) for an ACD device to be applied thereto (e.g., via suction cup). The underside of the landing pad may also be constructed so as to cover other medical components (e.g., cabling, electrodes, padding, etc.) and/or parts of the body (e.g., hair, anatomical crevices) and still maintain adherence to the body when being pulled upward during active decompression. For example, the underside of the landing pad may include a gel-like material (e.g., silicone gel) or other material which is readily conformable so as to maintain a seal with the medical components and/or parts of the body. Accordingly, the landing pad acts as a skin preparation device for maintaining adherence between the ACD device and the body of the patient, which may be used along with or separate from other medical components (e.g., sensors, ECG electrodes and defibrillation pads).

For performing an ACD CPR treatment, a rescuer can attach (e.g., by using an adhesive pad) the system for managing CPR treatment to the patient's chest and apply force (e.g., pushing or pulling) on a handle of the system during multiple phases of ACD CPR treatment. For example, during a compression phase, a rescuer presses downwardly on a handle of the system with sufficient force to compress the patient's chest and induce arterial blood circulation by ejecting blood from cardiac chambers. During an active decompression phase, the rescuer pulls upwardly on the handle of the system so that the adhesive pad actively expands the patient's chest, enabling cardiac chambers to refill with blood and ventilate the patient's lungs. The downward and upward strokes can be monitored and repeated at a controlled magnitude and rate to optimize blood circulation and enhance ventilation. For example, the compression magnitude can be in a range from about 3.5 cm to about 5 cm and the compression rate can be in a range from about 60 compressions to about 100 compressions per minute.

During the course of resuscitation, it may be desirable for an electrode assembly to be applied to the patient's chest. As described herein, the electrode assembly may include electrodes positioned in a manner that allows for an ECG signal to be recorded and/or for a therapeutic current to be transmitted to the heart. For example, electrodes may be placed in an A-A (anterior-anterior) position or in an A-P (anterior-posterior) position such that the therapeutic current may travel through the heart. The electrode assembly may further include a sensor (e.g., accelerometer) for collecting data related to chest compressions applied to the patient. Such data may be useful in estimating or otherwise providing chest compression parameters (e.g., compression depth, compression rate) to a system and/or the rescuer directly, to assist the rescuer in providing high quality chest compressions. The sensor may commonly be in wired communication with a CPR assistance system, such as a defibrillator, monitor and/or other resuscitative apparatus.

It may be further desirable for the rescuer to employ an applicator constructed to assist the rescuer in providing active compression decompression therapy to the patient. In some implementations, such as when the applicator relies on suction cup adherence to the patient's chest, the cable or wire that extends from the sensor can interfere with the ability of the applicator to maintain adherence with the patient's chest. That is, the cable hinders the suction cup from sustaining a partial vacuum with the chest and, hence, limits adherence, which in turn, prevents the performance of active decompression of the chest as intended.

Implementations of the present disclosure provide for electrode assemblies or other resuscitative systems having a chest compression sensor positioned at a location for performing chest compressions to further include a suitable coupling surface or other structure(s) configured to maintain adherence with an applicator body of an active compression decompression device. Such adherence with the applicator body may be sufficient to transfer the decompression force associated with active compression decompression therapy to the patient's chest in an appropriate manner (e.g., pulling up of the chest), while allowing the sensor to remain at the site where chest compressions are applied. Coupling surfaces described herein can overcome issues associated with the presence of a wire/cable that extends from the sensor. For example, a coupling mechanism including a coupling surface that provides for a substantially smooth surface located at a raised position over the cable, effectively eliminating the cable as a hindrance to suction adherence of the active compression decompression device and the coupling surface. The coupling mechanism allows the chest compression sensor to remain in suitable position and to be utilized to provide chest compression parameters while active compression decompression therapy is applied to the patient. In some implementations, the sensor and coupling surface may be provided independent from the electrode(s). Also, as discussed herein, the landing pad may include one or more adhesive materials such as a pressure sensitive adhesive and/or silicone gel, or other conformable substance that is able to form a robust seal with the body of the patient and various components (e.g., cable, electrodes, padding, etc.) on which the landing pad is placed.

Details regarding methods of using the system are described in detail with reference to FIG. 1 and the components of the system are described in detail with reference to FIGS. 1-12.

FIG. 1 shows an example of a system 100 for responding to an emergency medical condition of a patient 102 by providing CPR treatment. FIG. 1 illustrates an overhead view of rescuers 106a and 106b performing CPR on the patient 102 using an ACD CPR system 104. In the illustrated example of FIG. 1, the rescuers 106a and 106b are in position and providing care to the patient 102, with rescuer 106a in position and providing chest compressions to the torso of the patient 102 by using ACD CPR system 104, and rescuer 106b providing ventilation using a ventilation bag 107. In some implementations, the configuration and geometry of the ACD CPR system 104 enables the rescuer 106a to use the same body position and compression technique as in standard CPR treatment. In some implementations, the ACD CPR system 104 is configured to enable the rescuer 106a to perform active chest decompression by maintaining a firm grip on the ACD CPR system 104 and bringing the chest of the body upwards after compression. For example, the ACD CPR system 104 can be configured to transfer the compression force to the chest as a standard CPR device (e.g., via the device's piston and compression pad). The ACD CPR system 104 can include an adhesive pad or suction pad/cup that can be applied to the chest and can transfer the lifting force to the lower part of the patient's chest. A force gauge in the handle of the ACD CPR system 104 assists the rescuer 106a in applying the force needed to achieve desired compression characteristics, and the lift necessary for adequate decompression, as further described with reference to FIGS. 5A and 5B.

The rescuers 106a and 106b can be lay rescuers who were in the vicinity of the patient 102 when the patient 102 required care, or can be trained medical personnel, such as emergency medical personnel (EMTs). Although two rescuers are shown in FIG. 1, additional rescuers can also care for the patient 102, and can be included in a rotation of rescuers providing particular components of care to the patient 102, where the components can include chest compressions, ventilation, administration of drugs, and other provisions of care.

In general, the system 100 includes various portable devices for monitoring on-site care given to the patient 102. The various devices can be provided by emergency medical personnel, who arrive at the scene, and who provide care for the patient 102, such as rescuers 106a and 106b. The onsite rescuers 106a and 106b can be assisted by remote medical personnel 108, located at a medical facility 114 within a healthcare network. In the illustrated example, the rescuers 106a and 106b use several devices to provide an emergency treatment to the patient 102.

The devices used by the rescuers 106a, 106b, and/or the medical personnel 108 during CPR can include the ACD CPR system 104 and a portable defibrillator 112. A visual metronome can guide the rescuer 106a to compress and decompress at the appropriate rate and force. The ACD CPR system 104 can be a standalone device that is placed on the patient's chest (as illustrated in FIG. 1). The ACD CPR system 104 can also be attached or otherwise coupled to another device used by the medical personnel during CPR, such as the portable defibrillator 112. The attachment of the ACD CPR system 104 with other devices can enable synchronization of multiple CPR related procedures.

In addition to the ACD CPR system 104, FIG. 1 shows a portable defibrillator 112 and ancillary components arranged to provide feedback and instruction to rescuers 106a and 106b. FIG. 1 shows an example, in which visual feedback can be provided to the rescuer 106a from a location that is away from the defibrillator unit, and more immediately in the line of sight and focus of attention of the rescuer 106a, such as a graphical user interface of the ACD CPR system.

The portable defibrillator 112 is shown in a deployed state and is connected to the patient 102. In addition to providing defibrillation, the defibrillator 112 can serve as a patient monitor via a variety of sensors or sensor packages. For example, as shown here, electrodes 110 have been applied to the bare chest of the patient 102 and have been connected to the defibrillator 112, so that electrical shocking pulses can be provided to the electrodes in an effort to defibrillate the patient 102, and electrocardiogram (ECG) signals can be read from the patient 102. The defibrillator 112 can provide feedback in a conventional and known manner to an onsite rescuer, such as emergency medical personnel 106a and 106b.

In some implementations, additional therapeutic delivery devices (not shown) can be used to deliver the appropriate therapy to the patient. The therapeutic delivery devices can be, for example, a drug infusion device, an automatic ventilator and/or a device that includes multiple therapies such as defibrillation, chest compression, ventilation, and drug infusion. The therapeutic delivery devices are physically separate from the defibrillator 112, and control of the therapeutic delivery devices can be accomplished by a communications link from the defibrillator 112 that can be wired, wireless, or both.

In some implementations, control and coordination for the overall resuscitation treatment and the delivery of the various therapies can be accomplished through optimized chest compressions and decompressions optionally based on rescuer's profile by a processor that is integrated in the defibrillator 112 or is external to the defibrillator 112, such as the computing device 116 that is controlled by remote medical personnel 108. For instance, the computing device 116 can retrieve and process the force applied by the rescuer 106a through the ACD CPR system 104 and ECG data from the defibrillator 112. The computing device 116 can analyze the force applied by the rescuer 106a based on a profile of the rescuer 106. In parallel with analyzing the force applied by the rescuer 106a the computing device 116 can process ECG signals, and perform relevant determinations to optimize the amplitude and the frequency of the force applied by the rescuer 106a and therefore increase the success of CPR treatment. In some implementations, the processor integrated in the defibrillator 112 or a processor integrated in the ACD CPR system 104 can perform all the processing of the force applied by the rescuer 106a of the rescuer 106a and the ECG, and can display a suitable level of feedback to the rescuers 106a and 106b. The defibrillator 112 can also transmit to a separate device (e.g., ACD CPR system 104) particular sets of processed data, and in response, the separate device can perform particular control actions.

An electrode assembly 110 is illustrated as being attached to the patient 102 in a standard position. The electrode assembly 110, in this example, is an assembly that combines an electrode positioned high on the right side of the patient's torso and an electrode positioned low on the left side of the patient's torso, along with a sensor package located over the patient's sternum. The sensor package, which is obscured in the figure by the hands of rescuer 106a in this example, can include an accelerometer or similar sensor package that can be used in cooperation with a computer in the defibrillator 112 to generate an overall quality score for the chest compressions and decompressions, and the quality score can indicate instantaneous quality or average quality across a time. For example, as a simplified description, signals from an accelerometer can be double integrated to identify a vertical displacement of the sensor package, and in turn of the sternum of the patient 102, to identify the magnitude of each chest compression and decompression. The time between receiving such input from the sensor package can be used to identify the pace at which chest compressions and decompressions are being applied to the patient 102.

As discussed herein, the landing pad may be placed over the electrodes in a manner that allows the ACD device to be reliably pushed into the patient, compressing the patient's chest and also be pulled up so as to actively decompress the patient's chest, all while maintaining a suitable level of adherence. That is, the ACD device would not be unintentionally released from the patient's chest when an active decompression is desired.

The defibrillator 112 in this example is connected to the electrode package 110 and can operate according to a standard protocol (e.g., to provide defibrillating shocks to the electrode package 110). The defibrillator can be a professional defibrillator, such as the R SERIES, M SERIES, E SERIES, or X SERIES from ZOLL Medical Corporation of Chelmsford, Mass., or an automated external defibrillator (AED), including the AED PLUS, or AED PRO from ZOLL Medical Corporation. The defibrillator is shown in one position relative to the rescuers 106a and 106b here, but can be placed in other locations to better present information to them, such as in the form of lights, displays, vibrators, or audible sound generators on a chest-mounted component such as an electrode or via an addressable earpiece for each of the rescuers. Such feedback, as discussed more fully below, can be on units that are separate from the main housing of the defibrillator, and that can communication information about the patient 102 and performance of CPR to the defibrillator 112 or can receive feedback information from the defibrillator 112, through either wired or wireless connects that are made directly with the defibrillator 112 or indirectly through another device or devices.

In some implementations, the ACD CPR system 104 and the defibrillator 112 can be connected to the network 118 to transmit the acquired data to a computing device 116 that can be operated by the remote medical personnel 108. The CPR data transmitted by the ACD CPR system 104 and the defibrillator 112 to the computing device 116 can include data associated to the performance of the rescuer 106a and data associated to the response of the patient 102 to CPR treatment. The ACD CPR system 104 can send information about the performance of chest compressions and decompressions, such as depth and rate information for the chest compressions and decompressions. The defibrillator 112 can send ECG data and information related to characteristics of defibrillation signals. The computing device 116 can also receive data from the other sensors associated with the patient 102 such as an airflow sensor attached to a ventilation bag 107.

A central server system 120 can communicate with the computing device 116 or other devices at the rescue scene over a wireless network and/or a network 118, which can include portions of the Internet (where data can be appropriately encrypted to protect privacy) The central server system 120 can be provided as a server, or a virtual server, that runs server software components, and can include data storage including, but not limited to, a database and/or flat files. The central server system 120 can be part of a larger system of a healthcare continuum, in which patient data and rescuer profiles are stored. Patient data can be associated with an identification number or other identifier, and stored by the central server system 120 for later access.

Additionally, the central server system 120 can store rescuer profiles that include default rescuer profiles and rescuer specific profiles associated with particular rescuers. A rescuer specific profile associated with a particular rescuer can be retrieved by using an identification number or other identifier, stored by the central server system 120 for later access. The rescuer specific profiles can include template positions and data extracted from past rescue attempts, in which the rescuers participated. The data extracted from past rescue attempts can include rescuer's performance during CPR treatment. The rescuer's performance during CPR can include rescuer's skill level in performing CPR treatment, indicators of rescuer fatigue level, duration of CPR, and success of CPR treatment.

Users interacting with the system 100 can access the data in the central server system 120. For example, as shown in FIG. 1, medical personnel 108, operating a computing device 116 that communicates wirelessly, such as over a cellular data network can access current and past CPR data. As such, the medical personnel 108 can review CPR data stored in the central server system 120. In this manner, the system 100 permits various portable electronic devices to communicate with each other so as to coordinate and optimize care that is provided to a patient 102 based on the profile of the available rescuers 106a and 106b at the rescue scene. In such examples, the system 100 could be configured to optimize CPR treatment by providing optimal chest compressions and decompressions for shorter periods of time than the complete CPR duration and identification of the optimal moment for switching between rescuers 106a and 106b based on fatigue levels. In addition, the system 100 allows the rescuers 106a and 106b and other medical personnel to access real-time data and optimized real-time and/or historical data associated with a CPR treatment.

Example system 100 can provide real-time feedback to the rescuers 106a and 106b. For example, the defibrillator 112 or a display of a computing device can provide real-time audio-visual feedback, haptic feedback, and virtual reality support to the rescuers 106a and 106b, as described in detail with reference to FIGS. 6A and 6B. The process of observing the quality of a component of the CPR, such as the quality of chest compressions and decompressions, can continue recursively as long as care is being provided to the patient 102. In some implementations, trends in the quality of a particular CPR component can be tracked rather than absolute values of the performance, so that the defibrillator 112 can distinguish situations, in which a rescuer is giving a poor chest compressions and decompressions because he or she was trying to find the appropriate rhythm or was distracted by a temporary problem, from situations in which the user truly is tiring and rescuer's position should be optimized.

In some instances, the defibrillator 112 and/or the ACD CPR system 104 can be adaptable to different CPR protocols. For example, the defibrillator 112 and/or the ACD CPR system 104 can be programmed to execute ACD CPR protocols according to AHA general guidelines that can be personalized based on particular patient or rescuer needs or professional judgment. In such a situation, the defibrillator 112 and/or the ACD CPR system 104 can be programmed with the parameters for each of the protocols, and an operator of the defibrillator 112 can select a protocol to be executed by the defibrillator 112 (or the protocol can have been selected by a medical director) and the protocol to be executed by the ACD CPR system 104. Such a selection can occur at the time of a rescue, or at a prior time. For example, the ability to select a protocol can be differentiated based on access privileges, such as a person who runs an EMT service (e.g., a medical director of appropriate training and certification to make such a determination). A user interacting with the defibrillator 112 and/or the ACD CPR system 104 can select the protocol to be followed on each of the machines operated by the service, and other users can be prevented from making particular changes, if lacking access privileges. In this manner, the defibrillator 112 and/or the ACD CPR system 104 can be caused to match its performance to whatever protocol its users have been trained to.

Using the techniques described here, the defibrillator 112 can, in addition to providing defibrillation shocks, ECG analysis, and other features traditionally provided by a defibrillator, also provide indications to optimize the data related to compression and decompression in real-time and/or to switch rescuers between various components of providing CPR and other care to a patient. The defibrillator can be deployed in the same manner as existing defibrillators, but can provide additional functionality in a manner that can be easily understood by trained and untrained rescuers.

Figure 2B:
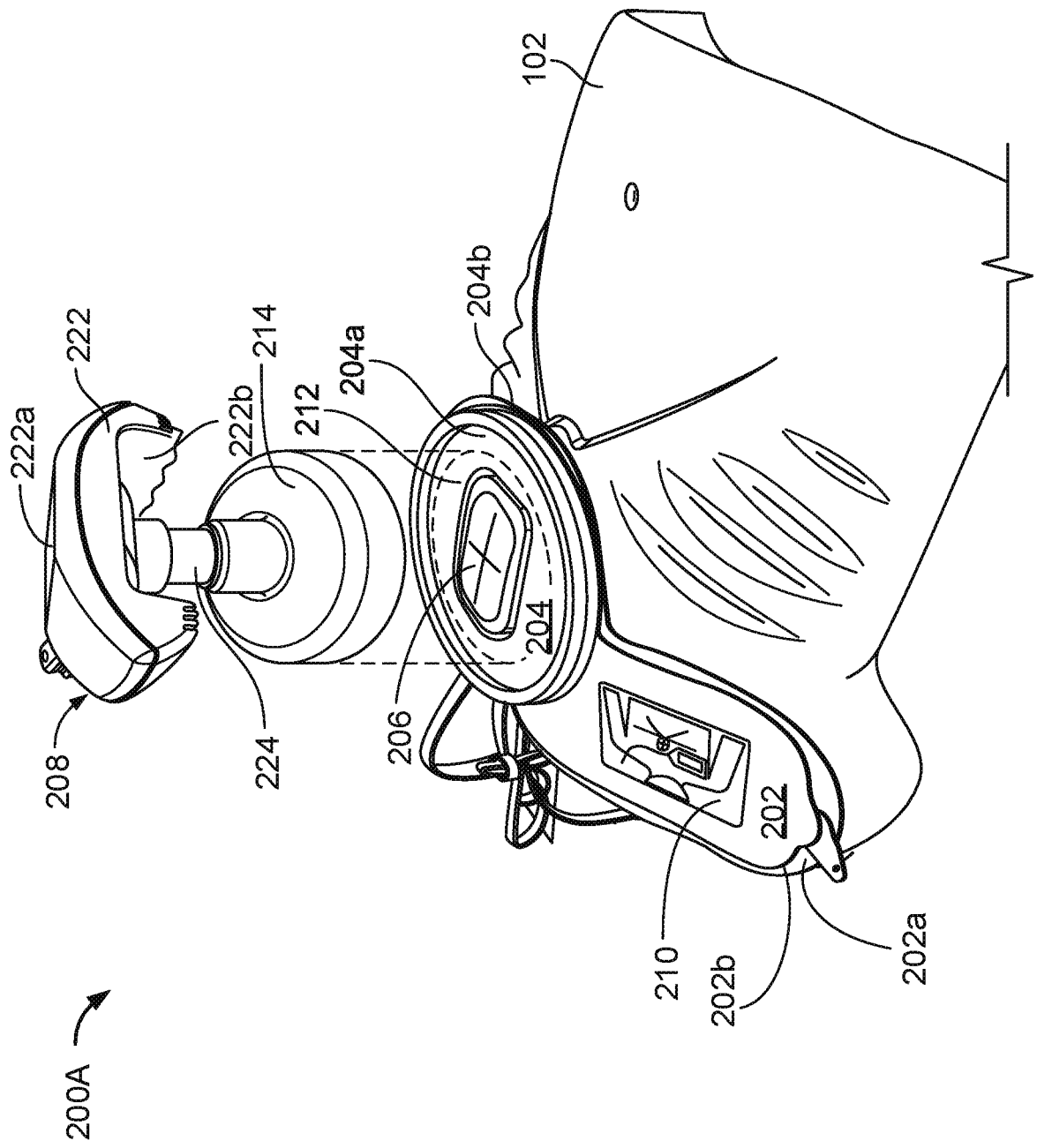
FIGS. 2A-2D multiple views of a first embodiment of the CPR assistance system that maintains suction adherence.
Figure 2E:
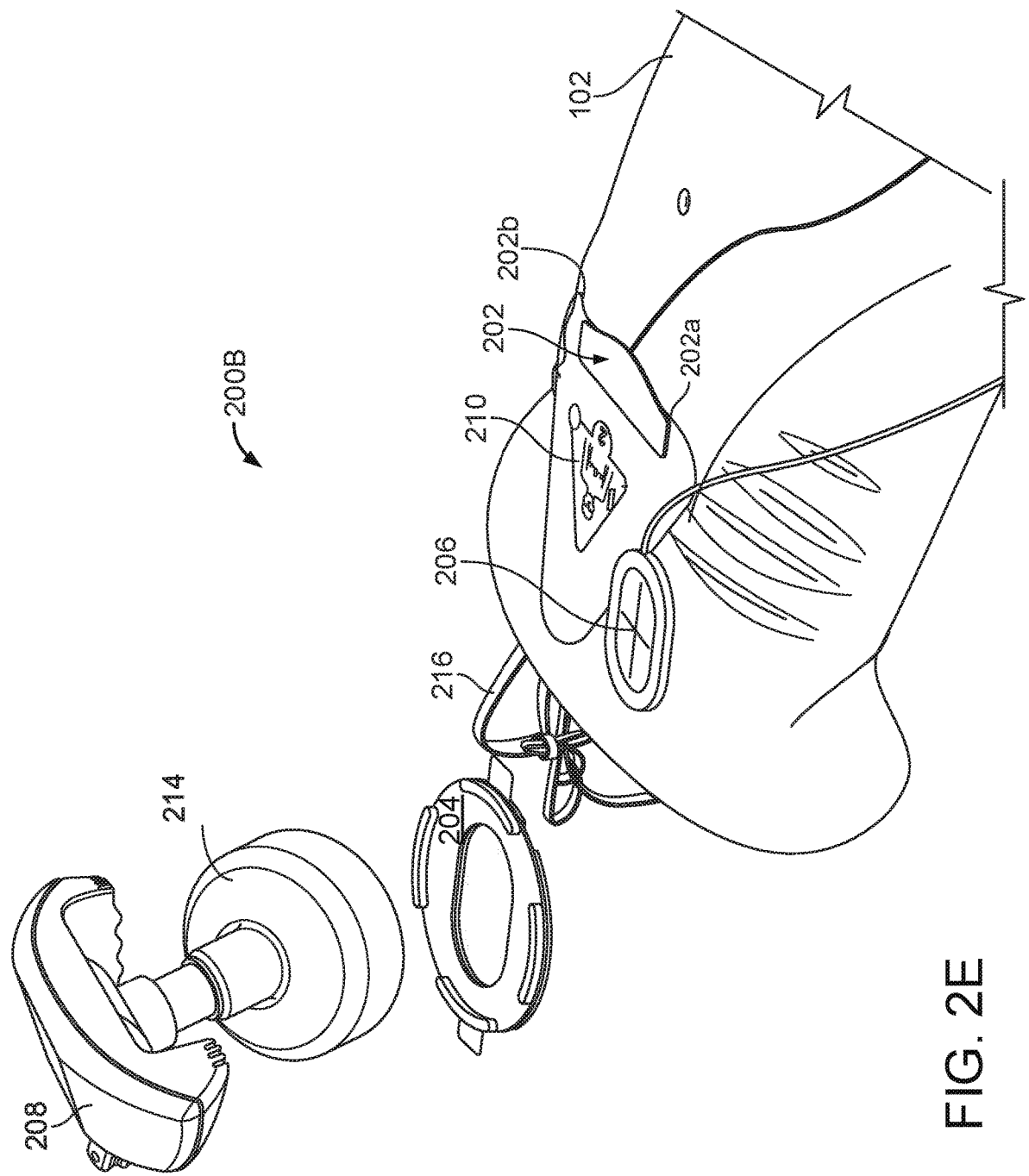
FIGS. 2E-2T show multiple views of a second embodiment of the CPR assistance system that maintains suction adherence.
Figure 2F:
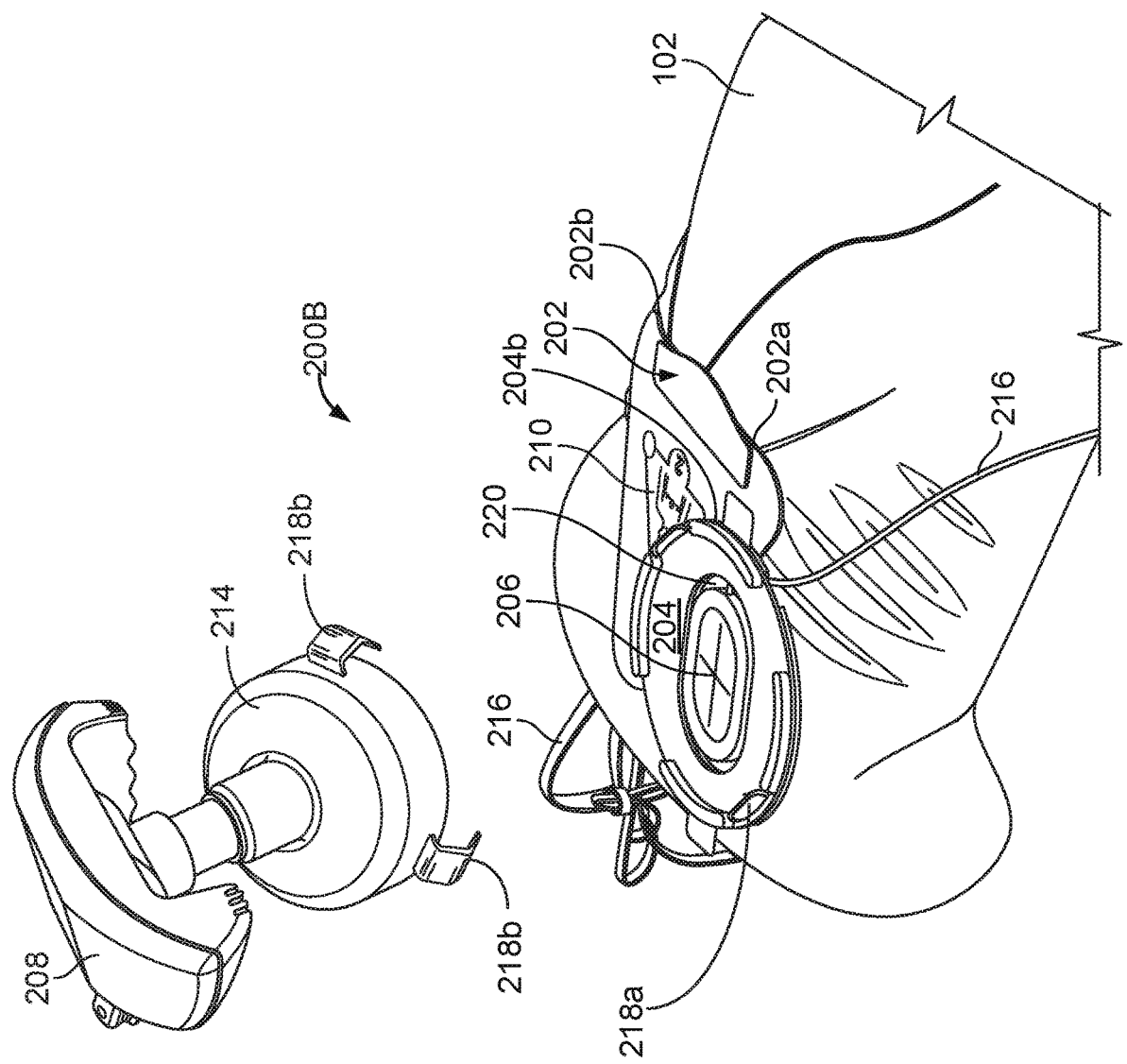
Figure 2G:
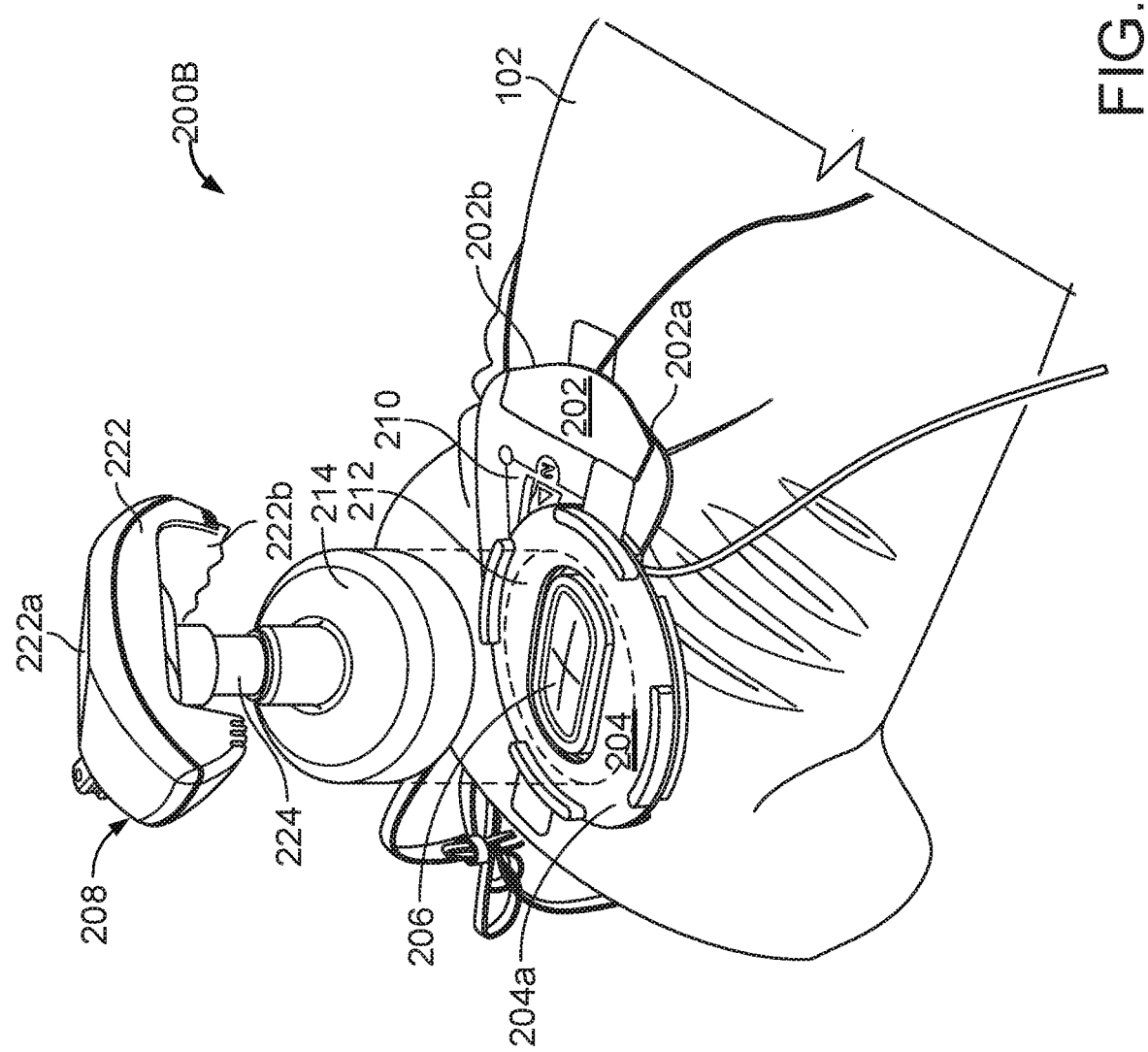
Figure 2H:
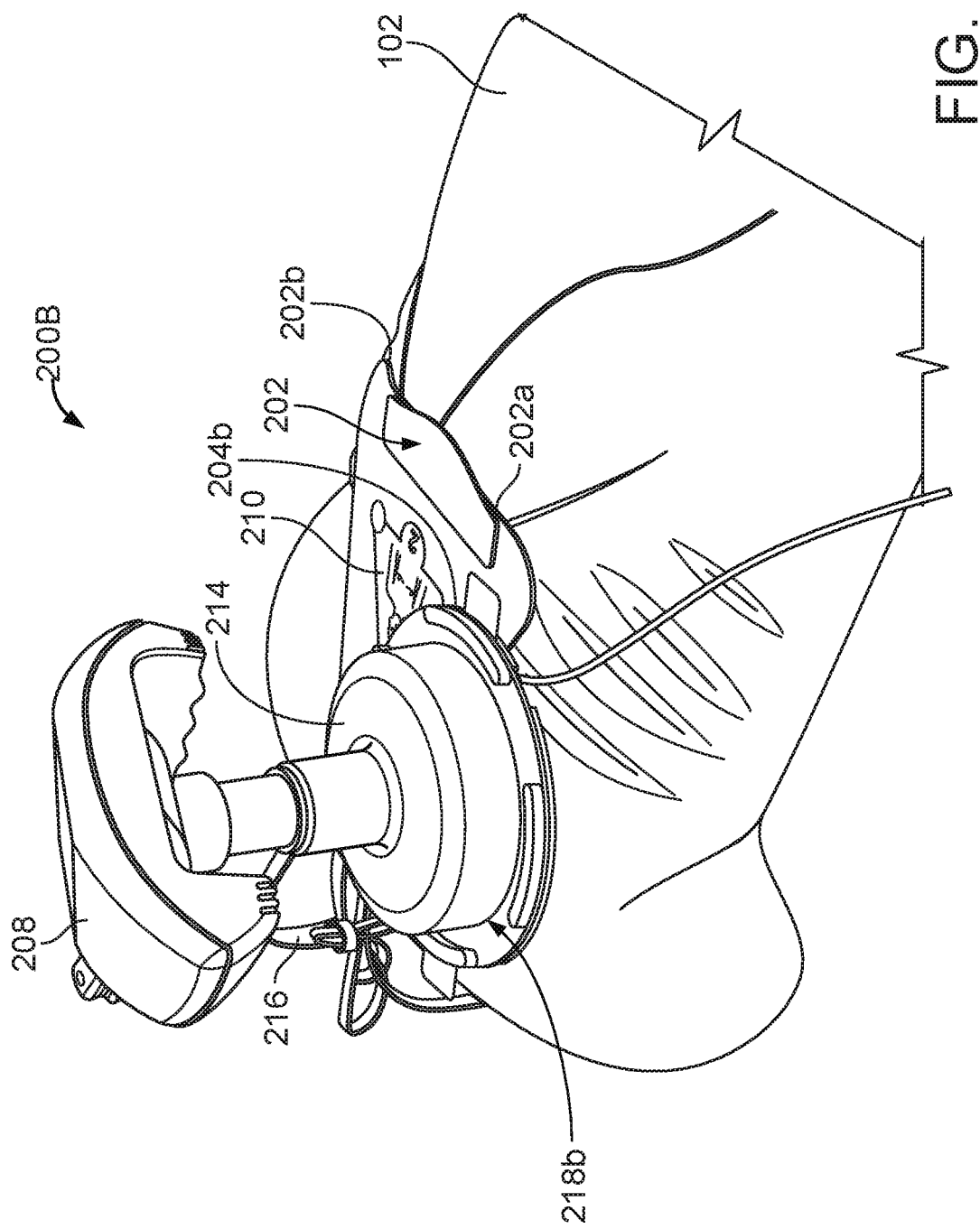
Figure 2I:
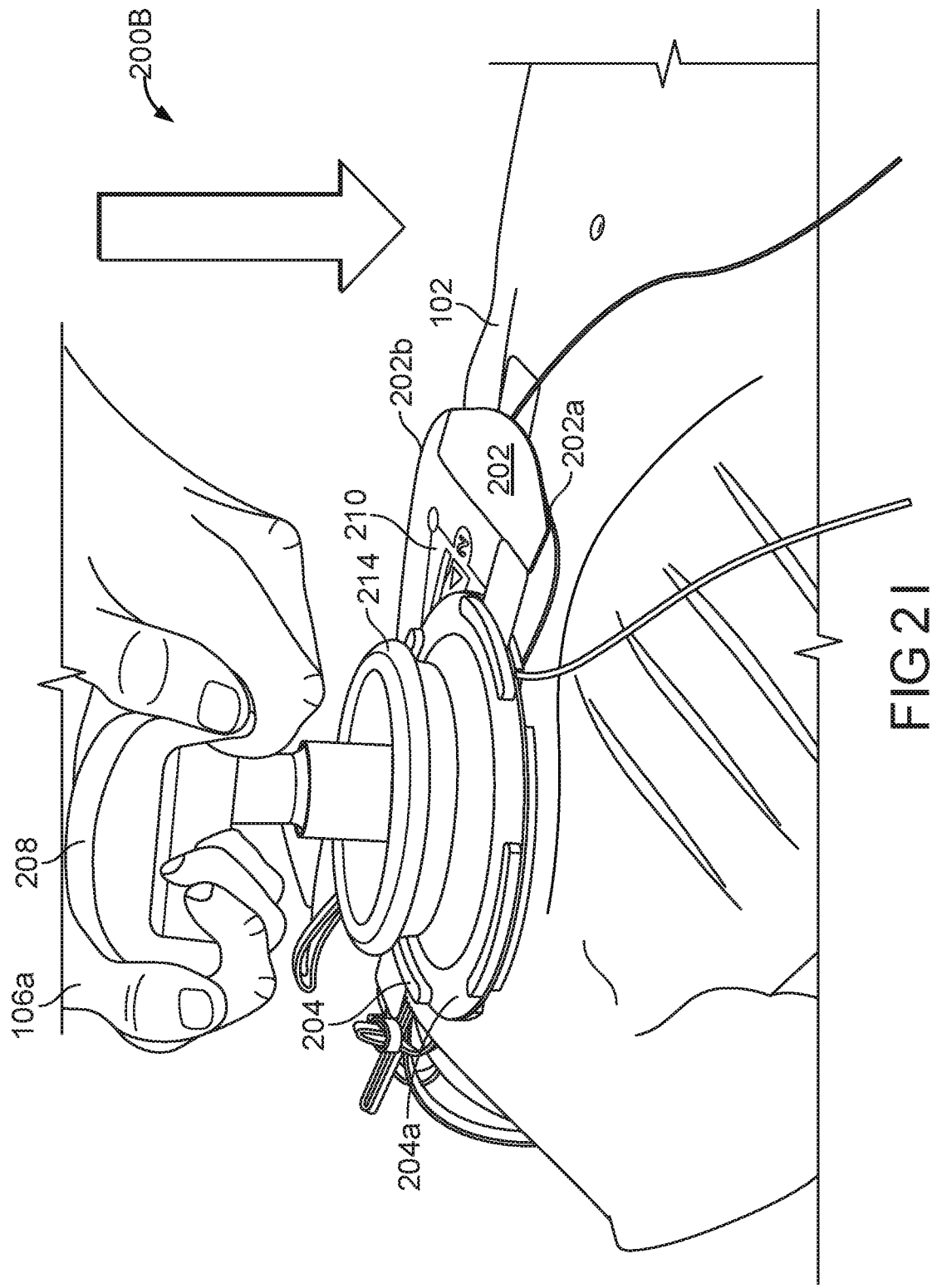
Figure 2J:
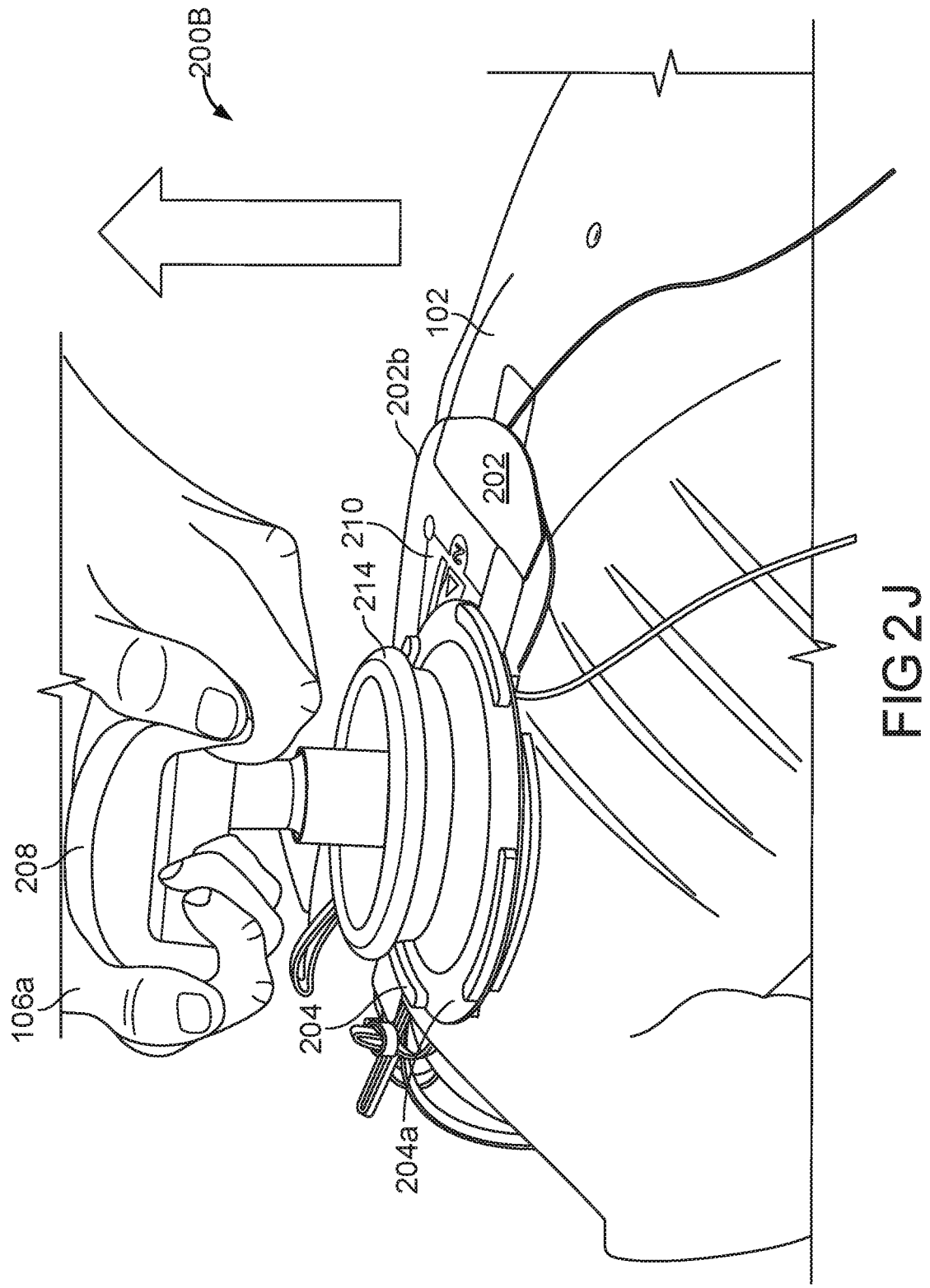
Figure 2K:
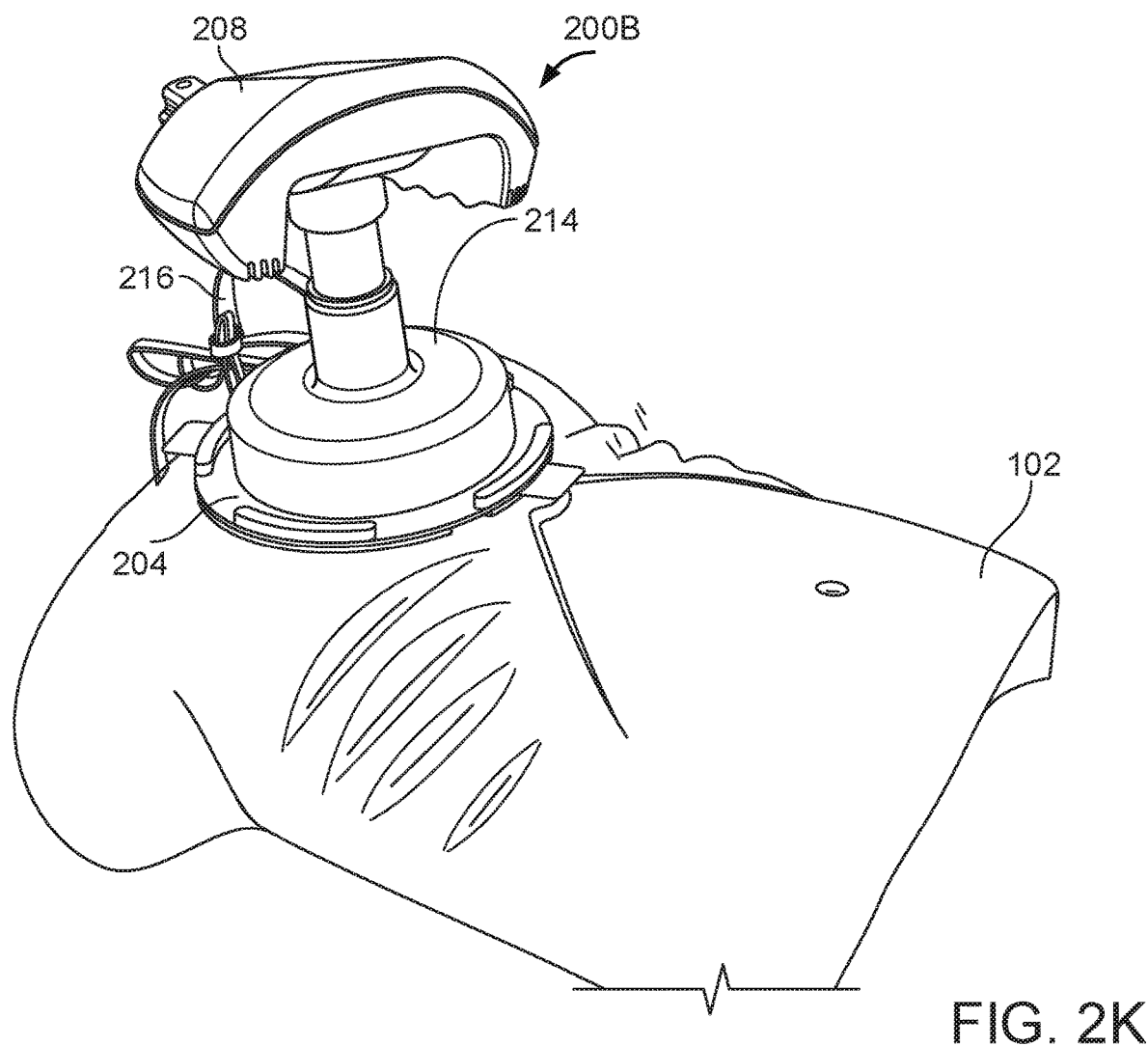
Figure 2L:
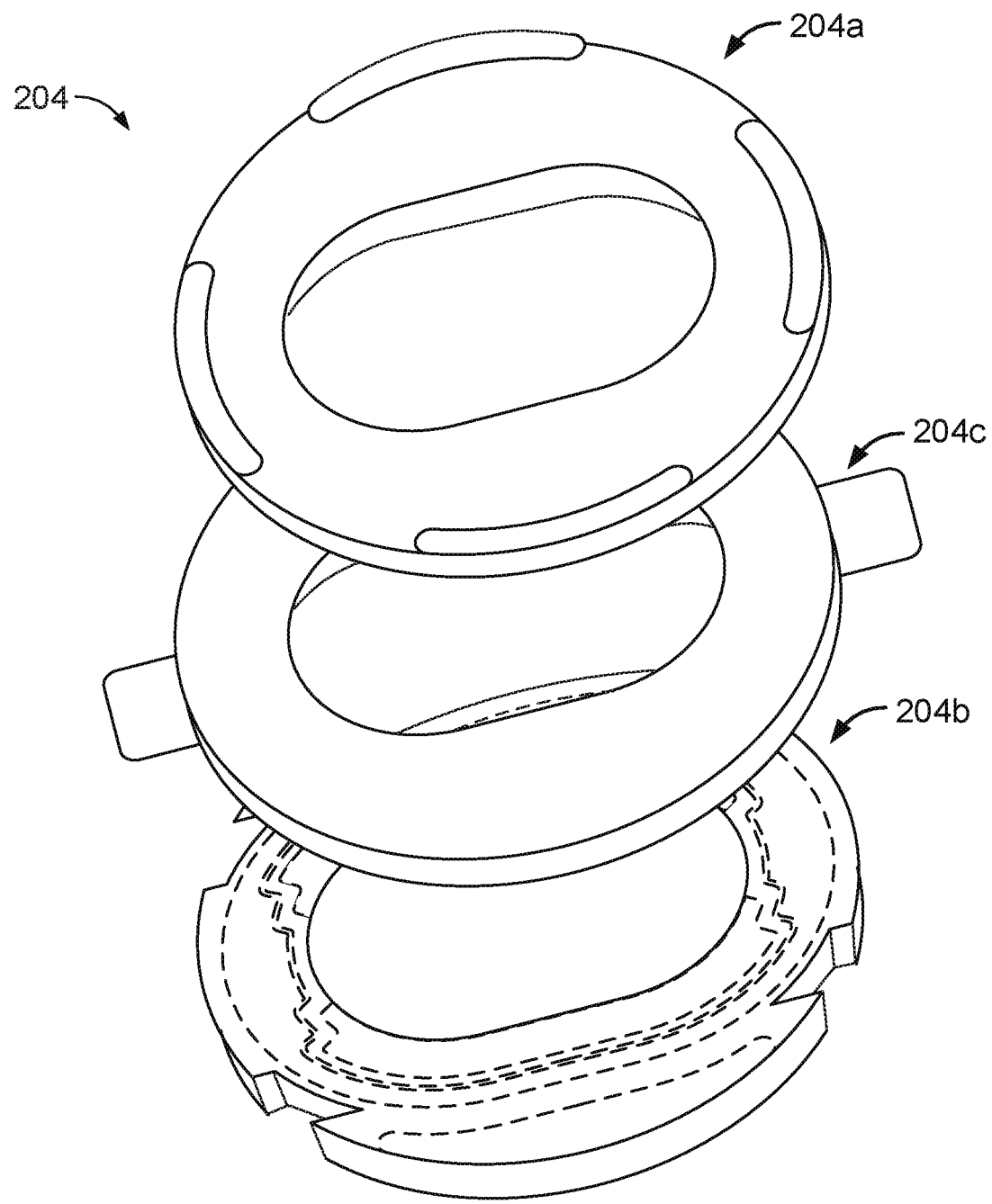

FIGS. 2A-2D illustrate examples of components of a first embodiment of an ACD CPR system 200A (e.g., ACD CPR system 104 described with reference to FIG. 1) that can be used to deliver a CPR treatment to the patient 102. FIGS. 2E-2T illustrate examples of components of a second embodiment of an ACD CPR system 200B (e.g., ACD CPR system 104 described with reference to FIG. 1) that can be used to deliver a CPR treatment to the patient 102. As shown in FIGS. 2A-2J, the ACD CPR system 200A, 200B may include an adhesive pad 202 having an electrode for delivering therapeutic energy to the patient, a landing pad 204, a sensor 206, and an active compression decompression device 208. In some implementations, as shown in FIG. 2K, the landing pad 204 can be attached directly to the chest of the patient 102 and the active compression decompression device 208 is placed on the landing pad 204.

The adhesive pad 202 can include an alignment feature 210. The alignment feature 210 can be included in the top layer of the adhesive pad 202. The alignment feature 210 can guide a rescuer in attaching the adhesive pad 202 to a desirable region of the patient's chest or other part of the thorax. In some cases, as shown, the alignment feature 210 involves indicia that help to instruct the rescuer in placement of the pad. The adhesive pad 202 can include a liner 202a and an adhesive face 202b (e.g., bottom part of the pad). The liner 202a can be removed or peeled away from the adhesive face 202b by a rescuer, to attach the adhesive pad 202 to the patient 102. The adhesive face 202b can be configured to be releasably attached or otherwise coupled to the patient's chest, for example on the sternum at the mid-nipple line as shown in FIGS. 2A-2E.

The adhesive face 202b can include a layer of high-traction or anti-slip material for contacting the skin of the patient 102, such that the adhesive pad 202 is able to remain attached to the patient's skin during CPR treatment. In some implementations, the adhesive face 202b can include pressure-sensitive adhesives, such as medical bandage adhesives, transdermal patches, and other medical applications. In some implementations, the adhesive face 202b can include natural and synthetic rubber-based formulations, such as polyisobutylenes, and acrylic and silicon-based materials, and swollen hydrogels, such as polyvinyl pyrrolidone, which are suitable in conjunction with electrodes. At completion of a CPR treatment with the ACD CPR system 200A, 200B, the adhesive face 202b can be removed by conventional means, e.g., by applying a solvent to the adhesive and/or peeling the adhesive face 202b away from the patient's chest.

The dimensions of adhesive pad 202 can be chosen to provide a desired contact area with the patient's chest. In some implementations, the larger the surface of the adhesive pad 202, the more expansion of chest can be achieved using ACD CPR system 200A, 200B (e.g., if the patient's chest is compliant or if a rib has been broken). Typically, for adult patients, adhesive pad 202 can have a generally square or rectangular shape. For children, the dimensions can be smaller. Other shapes can also be useful. For example, it can be desirable to shape the lower surface 202a of the adhesive pad 202 to conform to the general contours of the patient's chest. In addition, it may be desirable to provide a plurality of sizes and shapes of adhesive pads 202 in a single kit so that an adhesive pad 202 can be selected for the individual patient 102. The thickness of the adhesive pad 202 can depend on the resiliency of the material employed. For manual CPR operation, the adhesive pad 202 can be about 10 cm by 40 cm.

As noted above, the adhesive pad 202 can include an electrode configured to transmit a defibrillation current to the patient 102. The adhesive pad 202 may further include or be coupled to the sensor 206. The sensor 206 can be configured to measure at least one chest compression parameter during CPR treatment. A wire 216 can provide an electrical connection between the sensor 206 and a medical device (e.g., the defibrillator 112 described with reference to FIG. 1). The top upward facing layer of the landing pad 204 is spaced from its corresponding bottom downward facing layer in an elevated manner such that the wire 216 provides little to no interference in adherence between the active compression decompression device and the landing pad. That is, the coupling surface of the landing pad 204 remains substantially smooth, without the wire 216 that, absent the elevated nature of the portion of the coupling surface that adheres to the active compression decompression device, would otherwise be protruding and, hence, interfering with adherence between the suction cup and the upward facing coupling surface. The sensor 206 can be used to help assess and display the condition of the patient 102 prior to and during the CPR treatment. In some cases, the signals detected by the sensor 206 are used to initiate and optimize the CPR treatment. Examples of electrode and sensor configurations are further described with reference to FIGS. 6A and 6B.

In some implementations, the coupling surface of the landing pad 204 at least partially surrounds the sensor 206 and/or at least a portion of the wire 216. The landing pad 204 can be an integrated as part of the adhesive pad 202 or it can be releasably attached to the adhesive pad 202 as a separate component. Or, for example, the landing pad 204 may be provided as a separate component altogether from the electrodes (FIG. 2K), although the landing pad 204 may be placed over the electrodes while forming a suitable seal between the patient's body, optional components (e.g., wire 216, electrode pad) and the landing pad, as discussed herein. The components of the coupling surface of the landing pad 204 are described in detail with reference to FIGS. 2L-2T. The adherence between the coupling surface of the landing pad 204 and the active compression decompression device 208 can be sufficient to transfer a decompression force between the active compression decompression device 208 and the patient's chest during the CPR treatment without detaching in an undesirable manner (e.g., lifting off the chest during the active decompression stroke). The top layer 204a can be substantially smooth. Such a smooth surface may be helpful to maintain adherence with a suction portion of an active compression decompression device.

The active compression decompression device 208 can include an applicator body 214, a handle 222, and a stem 224. The applicator body 214 can be made of a deformable rubberized material, and it comprises a body portion and a seal portion, which extends integrally from one end of the body portion. The applicator body 214 is formed in a substantially circular, rounded, open, cup-shaped configuration so that it has an enlarged open end and a reduced end that is attached to the handle 222. An enlarged open interior area or cavity is formed in the applicator body 214 so that it opens outwardly through the open end. The applicator body 214 may include additional features, examples of which are described with reference to FIGS. 5C-5E.

The handle 222 includes an arcuate-shaped upper surface 222a and an annular planar lower surface 222b separated by a peripheral flange. The top of stem 224 is centrally located within annular lower surface 222b of the handle 222 and the bottom of stem 224 is centrally located on the upper surface 204a of the coupling surface 204. The cross-section of the applicator body 214 may have dimensions suitable for a compression/decompression area, which may correspond to a complementary region of the coupled surface 204, such as landing pad 212. The handle 222 is shaped to enable the rescuer's hands to suitably grasp the handle 222 with the palms resting on the upper surface 222a, the fingers wrapped around the ridge of the handle and the finger tips positioned against lower surface 222b (FIGS. 2C and 2D). Handle 222 and connective stem 224 can be constructed from a suitable rigid material, e.g. a molded plastic. Handle 222 can be filled with a gel, foam, padding or the like to enhance its shock-absorbing, feel and distributing capability.

The landing pad 204 includes a coupling surface 212 that complements, for example, in size and geometry, the applicator body 214. In some implementations, the coupling surface 212 includes a compliant and resilient material, such as a natural or synthetic foam. In some implementations, the landing pad 204 includes an attachment member 218a complementary to a corresponding attachment member 218b of the active compression decompression device 208. Each of the mechanical attachment members 218a and 218b can include an appropriate mating interface. The attachment members 218a and 218b can include mechanical fasteners, locking elements, gearing, hydraulics, pneumatics, electro-magnetic coupling and/or any other suitable feature(s) for maintaining adherence between the applicator body 214 and the coupling surface of the landing pad 204. For example, the attachment members 218a and 218b can form a pneumatic system for increasing or otherwise enhancing a vacuum between the applicator body 214 and the landing pad 204 (e.g., removing air there between). The attachment members 218a and 218b can also be configured to act as actuators to release the vacuum holds of the attached applicator body 214 from the landing pad 204, for instance, by injecting or allowing air to enter into the applicator body 214. The attachment members 218a and 218b can include well-known components such as a pump, valves, and/or fluid transfer lines.

In some implementations, the ACD CPR system 200A, 200B includes a passageway 220 located between the sensor 206 and the landing pad 204. The passageway 220 can be configured to optimize the propagation of the compression and decompression forces from the active compression decompression device 208 to the patient's chest. The dimensions of passageway 220 can be chosen relative to the base of the applicator body 214 and the surface of the sensor 206. For example, the passageway 220 can substantially encircle the sensor 206, such that the inner diameter of the passageway 220 is at least equal to or larger than the outer diameter of the sensor 206. Upon coupling of the applicator body 214 and the coupling surface 204, the passageway 220 can be at least partially or completely encircled by the base of the applicator body 214, such that the outer diameter of the passageway 220 is at least equal or smaller than the inner diameter of the base of the applicator body 214. The passageway 220 can have multiple configurations and structures, as described in detail with reference to FIGS. 3 and 4.

FIGS. 2C, 2D and 2H-2K illustrate perspective views of the ACD CPR system 200A, 200B, in which the active compression decompression device 208 is attached to the coupling surface of the landing pad 204. The illustrated arrangement of the ACD CPR system 200 can be used by a rescuer (e.g., rescuer 106a described with reference to FIG. 1) for performing both active compressions (FIGS. 2C and 2I) and decompressions (FIGS. 2D and 2J) for manual CPR treatment. The configuration of the active compression decompression device 208 enables the rescuer 106 to press down on upper surface 222a of handle 222 with the palms of the hands to apply a compressive force against landing pad 204 and patient's chest over the area upon which compression/decompression is applied. The configuration of the active compression decompression device 208 also allows the operator to lift up by pressing on the lower surface 222b of the handle 222 with the fingers. Since lower surface 202a of adhesive pad 202 is adhered to the contact area of patient's chest, the lifting motion on handle 222 lifts and expands patient's chest, which may be effective to lower intrathoracic pressure and enhance venous return of blood to the heart and refilling of the cardiac chambers.

FIGS. 2E-2T illustrate multiple views of the second embodiment of the ACD CPR system 200B. FIGS. 2I-2K illustrate a perspective view of the ACD CPR system 200B, in which the active compression decompression device 208B is attached to the coupling surface of the landing pad 204. FIG. 2L illustrates an exploded view of an embodiment of the landing pad 204. The landing pad 204 includes a top layer 204a, a bottom layer 204b, and a middle layer 204c. In this embodiment, the top layer 204a is constructed so as to be able to maintain adherence with the active compression decompression device 208 and is described in detail with reference to FIGS. 2M and 2N. The top layer 204a can include foam with adhesive on the side that comes in contact with the middle layer 204c. The bottom layer 204b is constructed so as to be able to maintain adherence with the patient's chest (FIG. 2K), optionally in conjunction with the adhesive pad 202 and is described in detail with reference to FIGS. 2O-2R. The middle layer 204c is constructed so as to provide structural stability to the coupling surface of the landing pad 204 and is described in detail with reference to FIGS. 2S and 2T. The top layer 204a, bottom layer 204b, and middle layer 204c may be attached to one another by any suitable manner known in the art. For example, the layers 204a, 204b, 204c may be attached by an adhesive, heat-sealed, etc. The top layer 204a can be adhered to the middle layer 204c with an adhesive, such as pressure sensitive adhesive (PSA), or any other appropriate method. Bottom layer 204b can be adhered to middle layer 204c with a thin film (of approximately 0.1 mm) that has PSA on both sides. It should be appreciated that the landing pad is not required to be formed of layers as shown in the figures, but rather may be formed as a unitary component. The shape of this film is such that its inner perimeter is the same shape as the inner perimeters 246 and 252 of the middle and bottom layers. The outer perimeter of this film is offset from the inner perimeter. Each of the layers 204a, 204b, 204c may be constructed to have any appropriate thickness. For example, one or more of the layers 204a, 204b, 204c may have a thickness of between 1 mm and 20 mm, between 1 mm and 10 mm, or each of the respective thicknesses may fall within another suitable range.

Figure 2M:
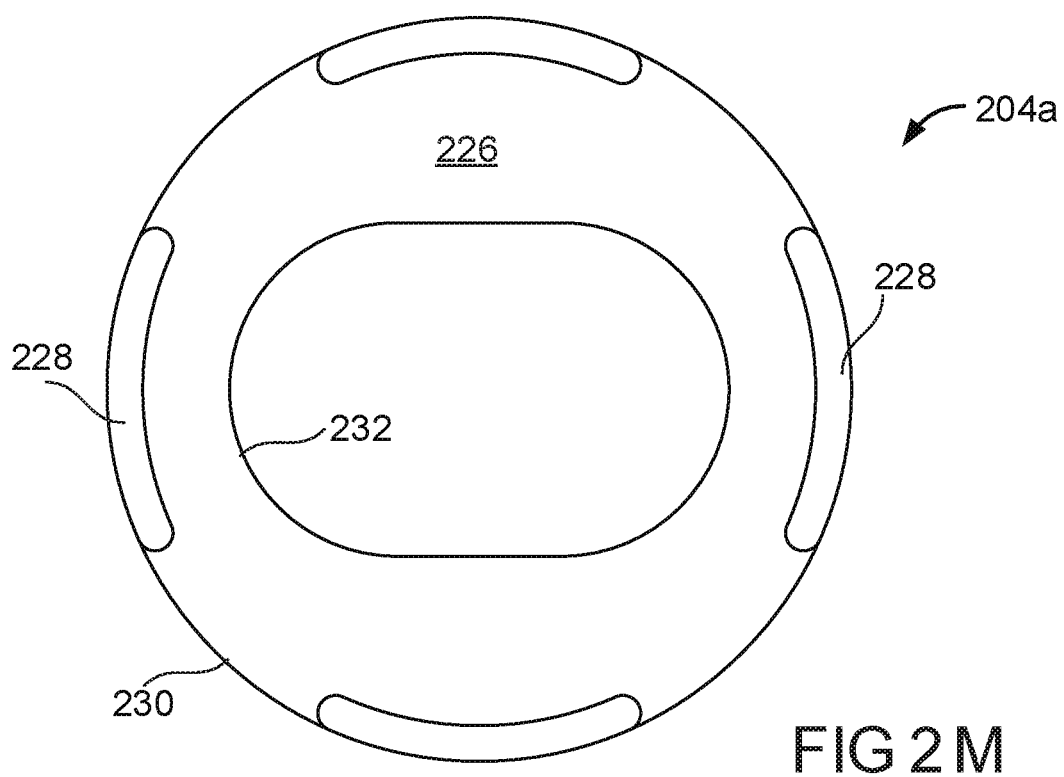
Figure 2N:
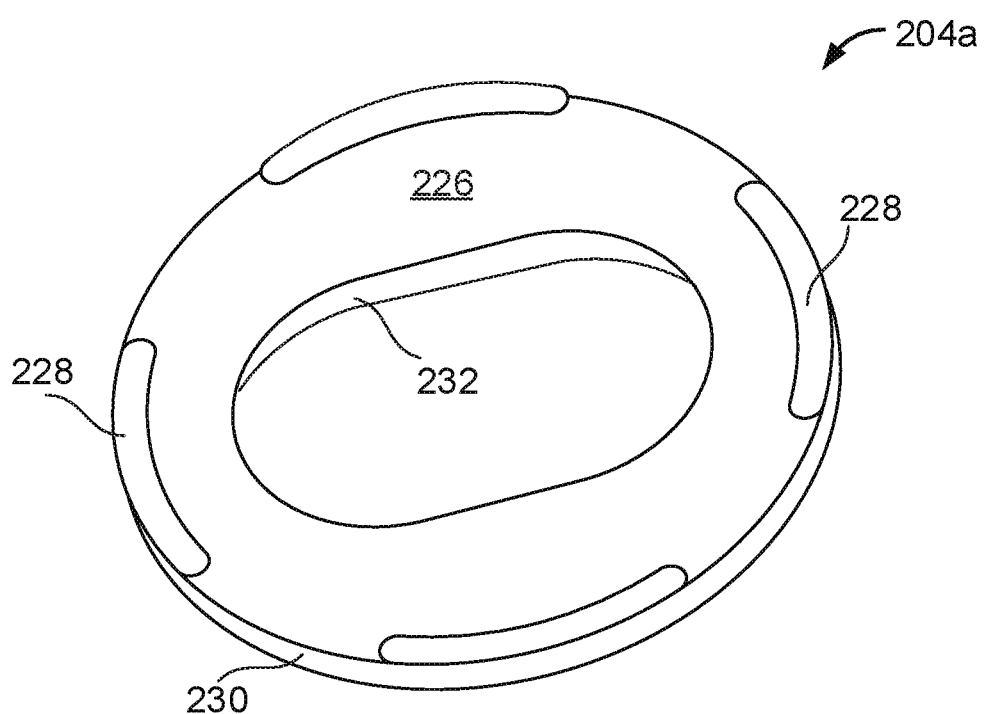
Figure 2O:
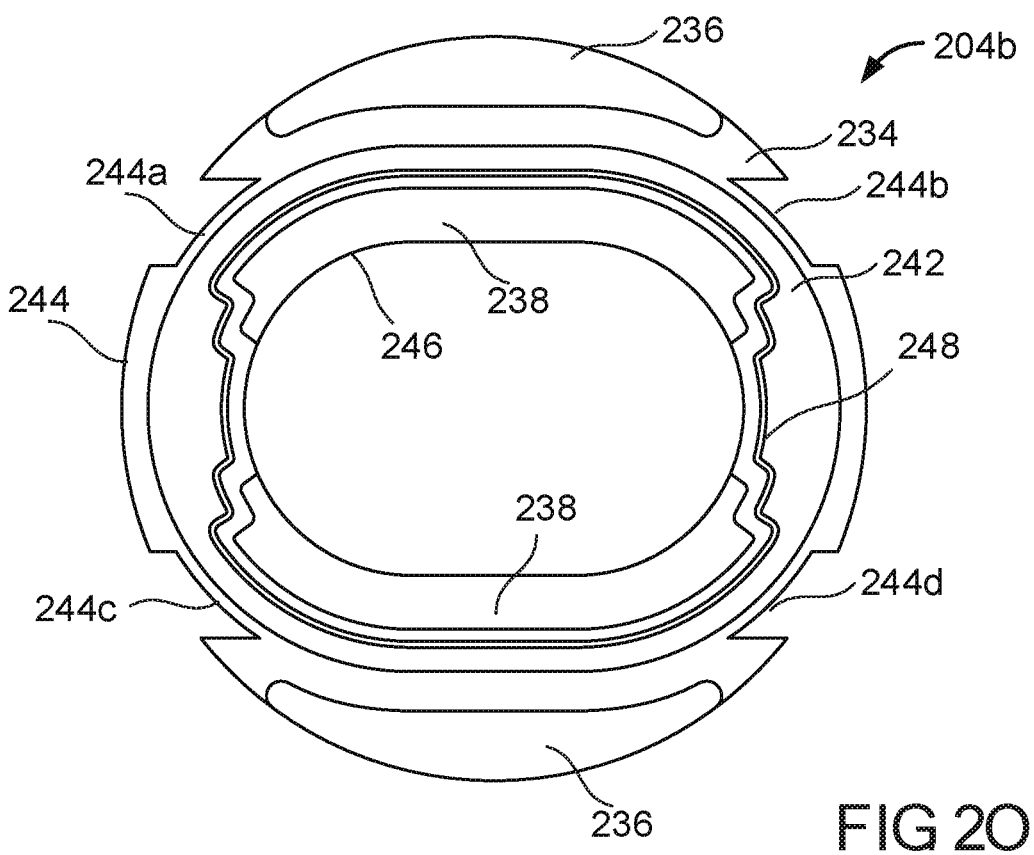
Figure 2P:
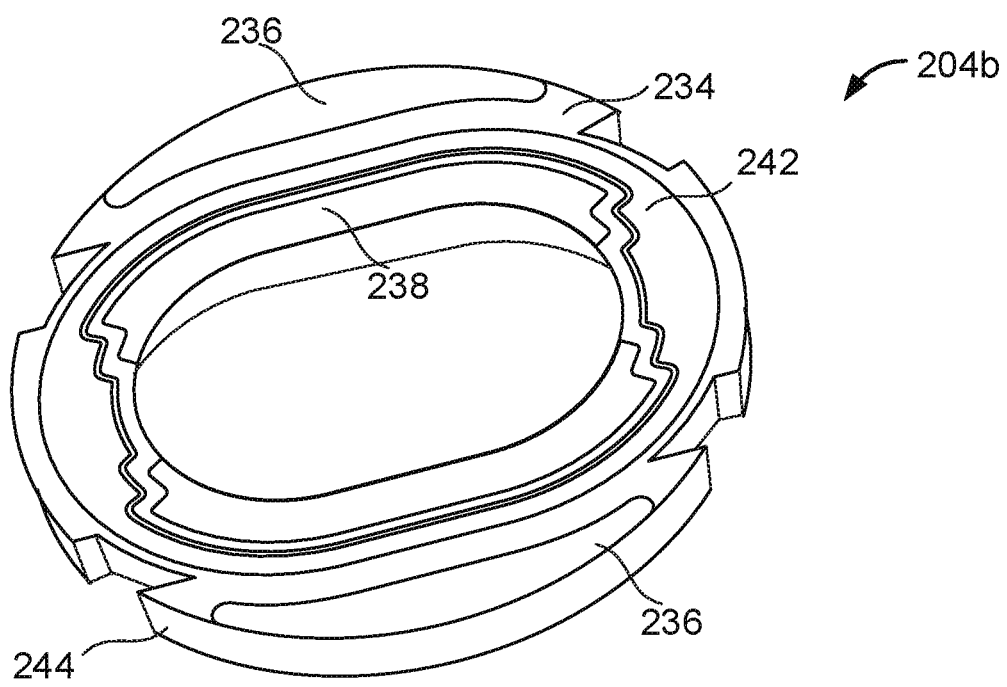

FIGS. 2M and 2N illustrate a top view and a perspective view of the top layer 204a, respectively. In this embodiment, the top layer 204a is constructed to maintain adherence with the active compression decompression device 208. The top layer can include a base 226 and a plurality of barriers 228. The base 226 can be substantially smooth, for example, so as to receive the suction cup of an ACD device. The base 226 can have a thickness of between 1.0 mm and 5.0 mm (e.g., approximately 1.5 mm), between 1.0 mm and 3.0 mm, between 1.0 mm and 2.0 mm, or may have any other suitable thickness. The base 226 can have an approximately circular outer boundary 230 and an opening 232. The opening is located at and extends through a central region of the landing pad and is of a sufficient size to accommodate placement of a chest compression sensor 206 (e.g., CPR puck having an accelerometer or other motion sensor for measuring chest compression rate and depth information to assist in providing CPR feedback). The opening 232 has a geometrical shape (e.g., donut or oval shape) that substantially matches the outer perimeter of the sensor 206 or otherwise provides a space where the sensor 206 may be located. The opening 232 has a size larger than the outer perimeter of the sensor 206 to form an opening 220 with a constant width. The base 226 can be made of a compliant composition material such as foam. The plurality of barriers 228 can be configured to maintain the position of the active compression decompression device 208, or otherwise guide the user in placing the ACD device 208 appropriately on the coupling surface of the landing pad 204. Any suitable number of barriers 228 may be employed, for example, one or more rails of relatively constant width that may be aligned with the outer boundary 230. The barriers 228 can have a thickness of between 1.0 mm and 10.0 mm (e.g., approximately 4.5 mm), between 23.0 mm and 8.0 mm, between 3.0 mm and 5.0 mm, or may have any other suitable thickness.

Figure 2Q:
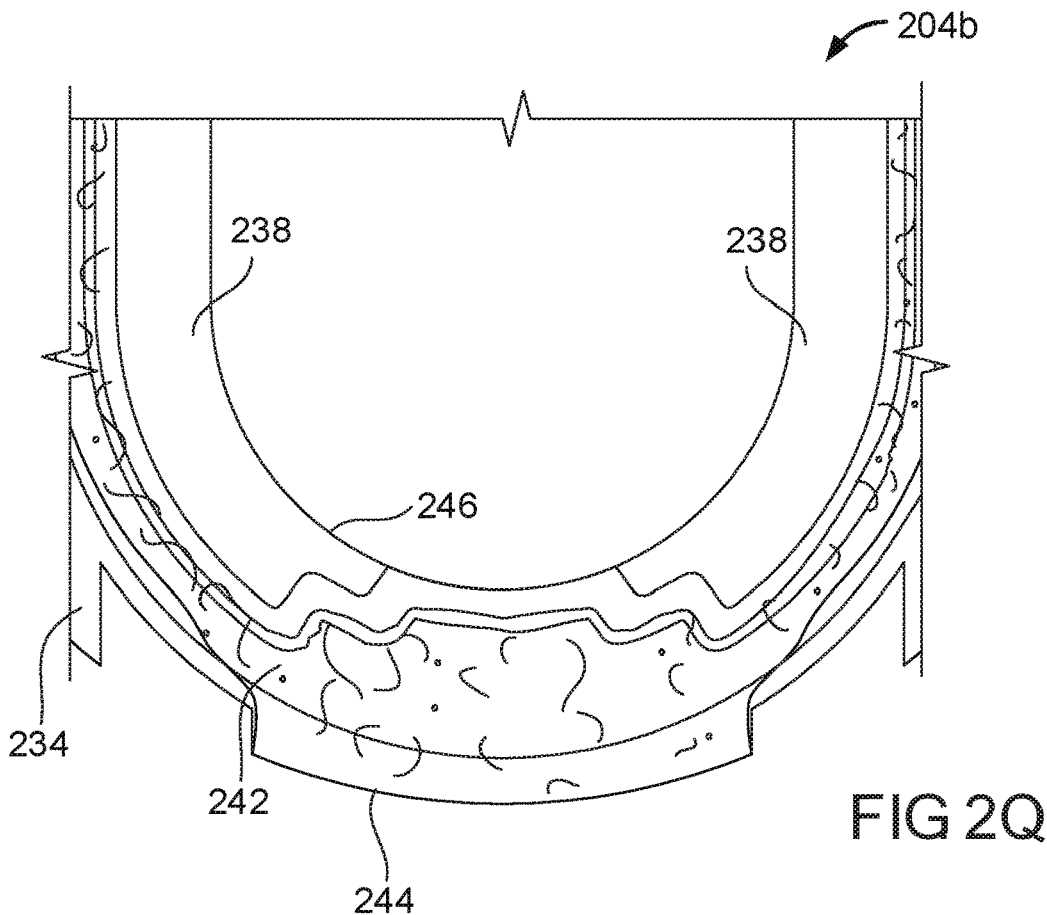
Figure 2R:
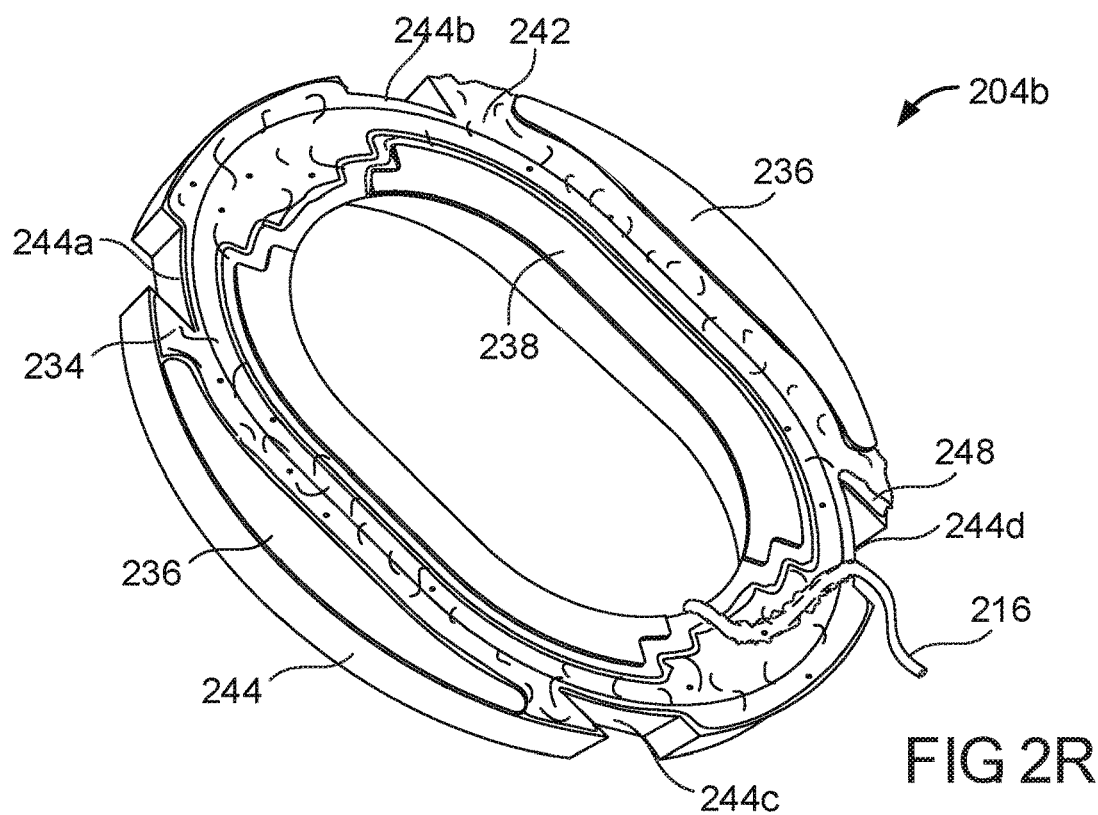

FIGS. 2O-2R illustrate a bottom view and a perspective view of the bottom layer 204b, respectively. The bottom layer 204b can be configured to maintain adherence with the patient's chest, while at the same time forming an appropriate seal with the adhesive pad 202 and/or any cabling that extends from the opening 246 beyond the outer boundary 244. The bottom layer 204b includes a base 234, a pair of laterally extending wings 236, pressure sensitive adhesive 238, and gel-like material 242. The base 234 can be made of a compliant composition material such as foam, plastic, or other suitable material. The base 236 may further have an outer boundary 244 and an opening 246. In this embodiment, segments of the outer boundary 244 are slightly recessed to form segmented regions 244a, 244b, 244c, 244d to better accommodate wire 216, a cable, electrode padding, and/or other components extending from the opening 246 past the periphery of the outer boundary 244 (as illustrated in FIG. 2R). That is, the wire 216 extending from the chest compression sensor located within the opening 246 may extend through one of the segmented regions 244a, 244b, 244c, 244d so that less of the foam material interferes with the seal. The segmented regions 244a, 244b, 244c, 244d reduce the stiffness of the bottom layer 204b. This allows the outer boundary 244 to flex about the segmented regions 244a, 244b, 244c, 244d during decompression. This reduces the force needed to "bend" the bottom layer 204b so that the bottom layer 204b remains in contact with and conforms to the patient's chest or the adhesive pad 202 during decompression. The reduced stiffness of the bottom layer 204b reduces the strain on 236, 238 and 242 during decompression.

The pair of wings 236 can be configured to provide an enhanced level of conformity to the anatomy of the patient 102 when the landing pad is attached to the patient (FIG. 2J). The pair of wings 236 can be made of a compliant material, such as foam that can adapt to the shape of the anatomy of the chest of the patient 102 (FIG. 2J). Accordingly, the flexible wings 236 may be able to deflect away from the relatively more rigid middle layer 204c so as to conform to the shape of the patient's chest. As a result, while the structurally stable middle layer 204c of the landing pad is able to maintain adherence to the ACD device and, hence, maintain its shape when being pushed and pulled, the flexible wings 236 are able to maintain adherence to the patient, no matter the shape of the patient's body (FIG. 2J). The wings 236 can have a thickness of between 0.1 mm and 5.0 mm (e.g., approximately 0.8 mm), between 0.5 mm and 3.0 mm, between 0.5 mm and 2.0 mm, between 0.5 mm and 1.0 mm, or may have any other suitable thickness.

Prior to use, the pressure sensitive adhesive 236 can initially be covered by a removable protective layer. As illustrated in FIGS. 2Q and 2R, the gel-like material 242 may extend completely or partially around the opening 246, allowing for a proper seal to be formed between the landing pad and the body of the patient. As noted above, the physical characteristics (e.g., density, viscosity) of the gel-like material 242 may ensure a suitable seal between the bottom layer 204b and the patient's body, even when various medical components such as cabling or electrode pads are located in between. As depicted, the gel-like material 242 extends in a circumferential (e.g., track-like) fashion around the opening 246 to ensure that the seal is formed no matter where such medical components are placed relative to the landing pad.

The gel-like material may be composed of any suitable material that is able to maintain the seal between the bottom layer 204b of the landing pad and the patient's body. For example, the gel-like material may be a highly biocompatible, transparent gel having a relatively long (months or years) shelf life at room temperature. The gel-like material may also exhibit tacky and adhesive properties. In various embodiments, the gel-like material may be a silicone gel with a density of between 0.5 g/cm3 and 2.0 g/cm3 (e.g., approximately 0.98 g/cm3) and a viscosity varying from about 8000 mPa·s to about 15000 mPa·s. An example of a suitable silicone gel that may be used in embodiments of the present disclosure includes the SILPURAN® 2112 A/B Biocompatible RTV-2 Silicone Adhesive provided by Wacker Chemie AG. In various embodiments, this particular silicone gel has components A and B which may be mixed homogeneously for vulcanization according to a suitable ratio A:B, such as between 1:1 and 1:10, between 1:1 and 1:5, between 1:1 and 1:4, between 1:1 and 1:3, between 1:1 and 1:2, between 1:1 and 1:1.5, amongst others. The gel-like material may exhibit an appropriate thickness 248 extending past the structural material (e.g., compliant foam) bottom layer 204b. For example, the thickness of the gel-like material extending past the compliant foam may be between 1.5 mm and 13 mm (e.g., approximately 3 mm), between 1.5 mm and 6 mm, between 1.5 mm and 3 mm, or another suitable thickness.

Figure 2S:
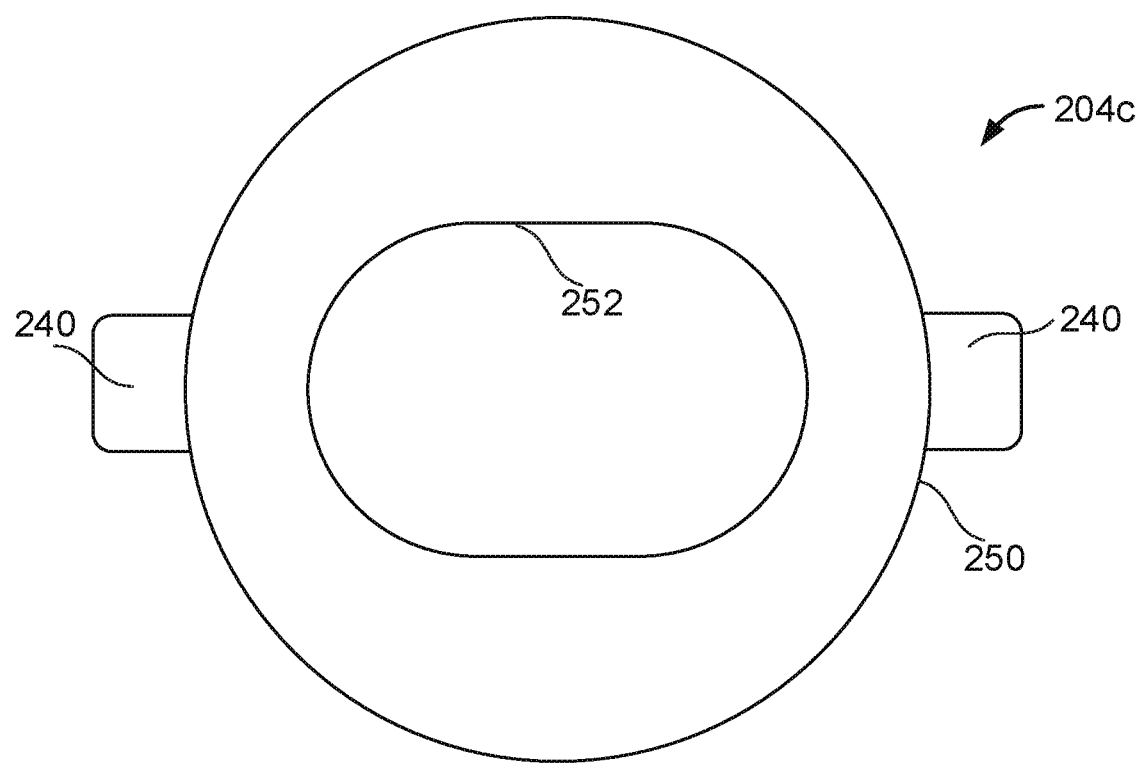
Figure 2T:
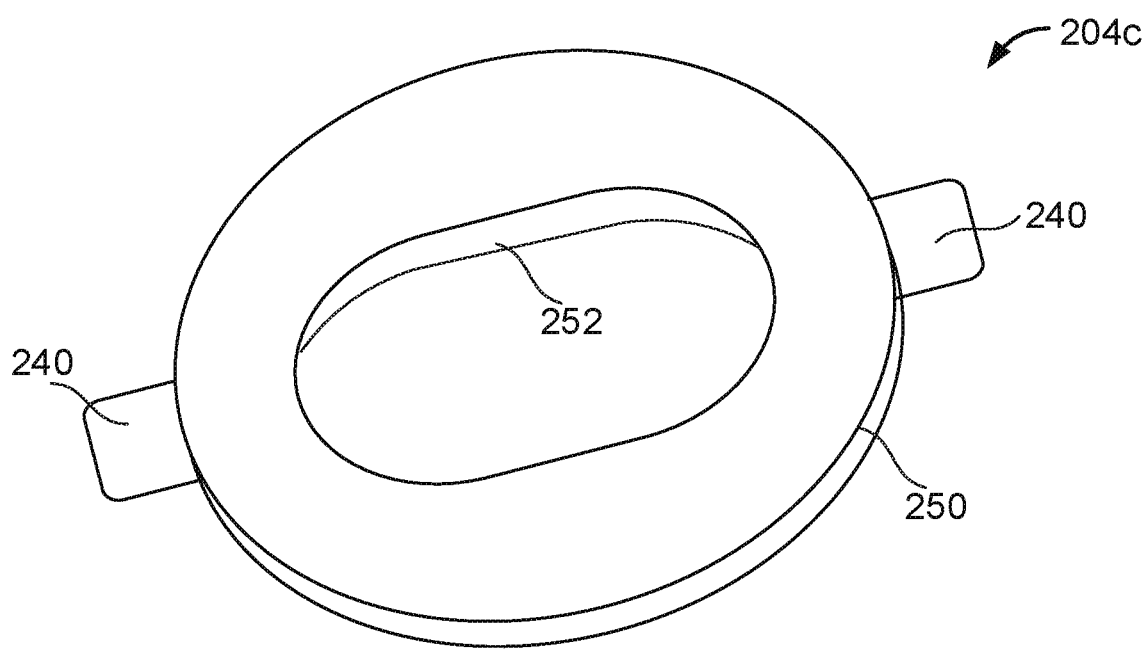
Figure 3A:
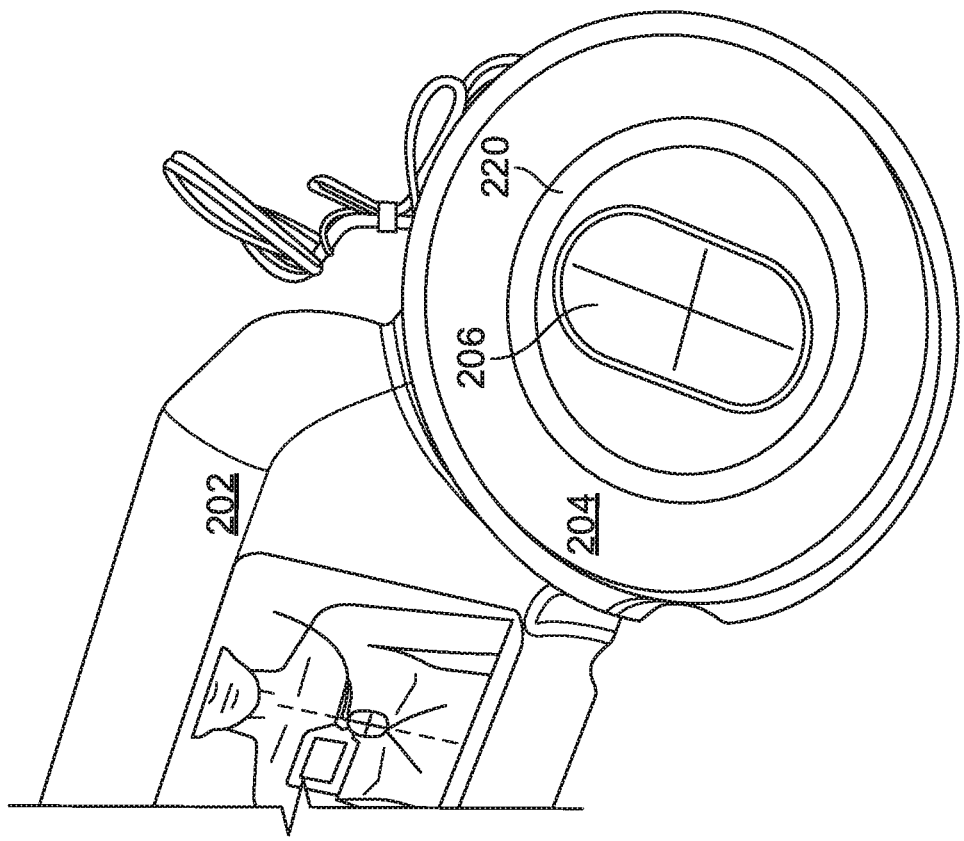
FIGS. 3A-3D show views of example coupling surfaces configured to maintain suction adherence in accordance with the first embodiment of the CPR assistance system.
Figure 3B:
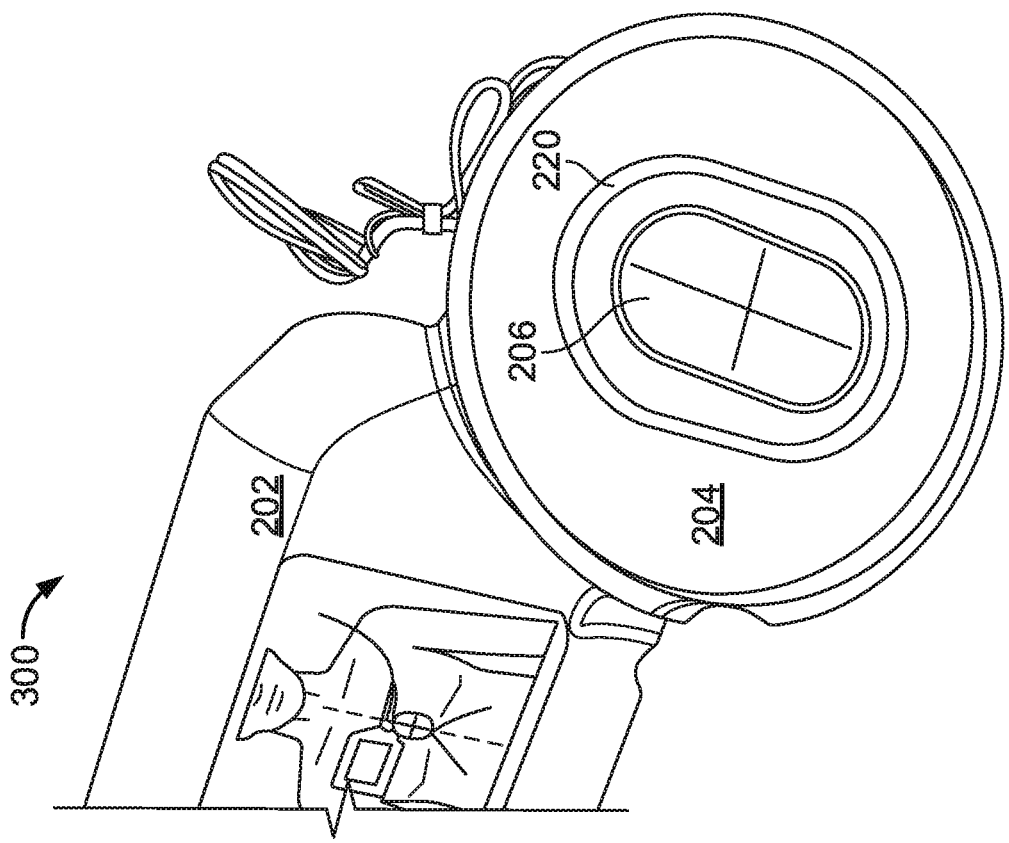
Figure 3D:
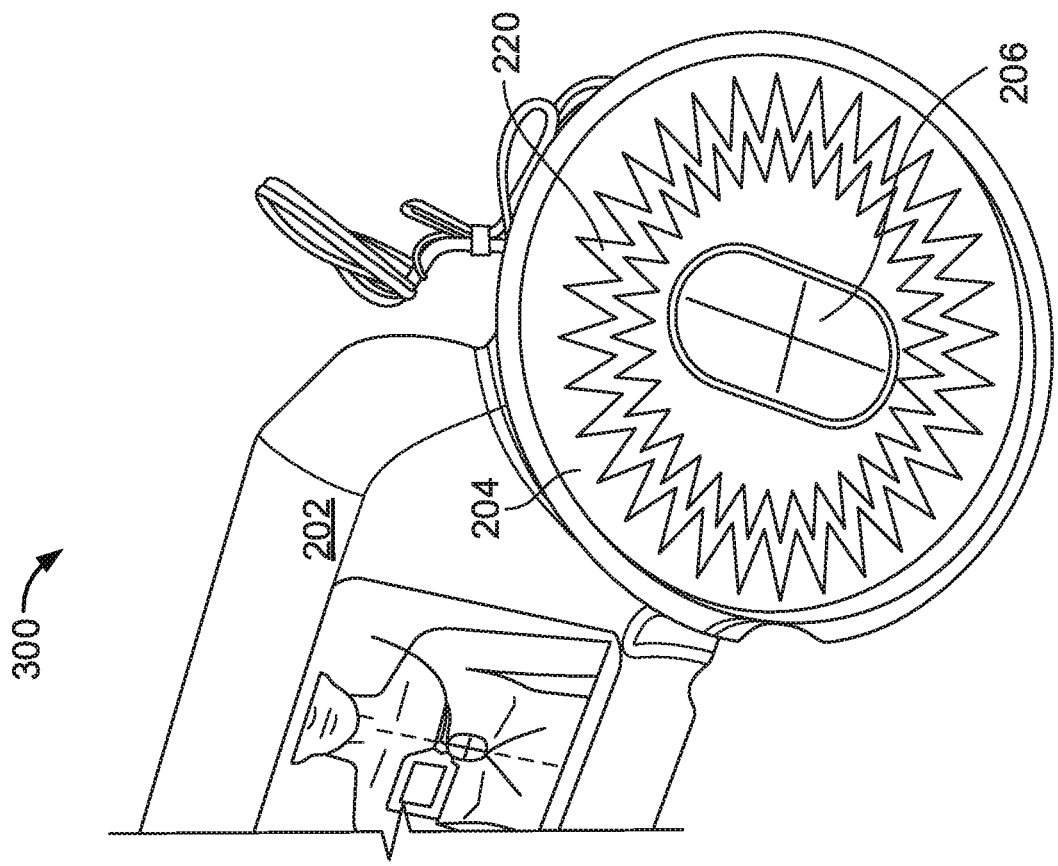
Figure 3C:
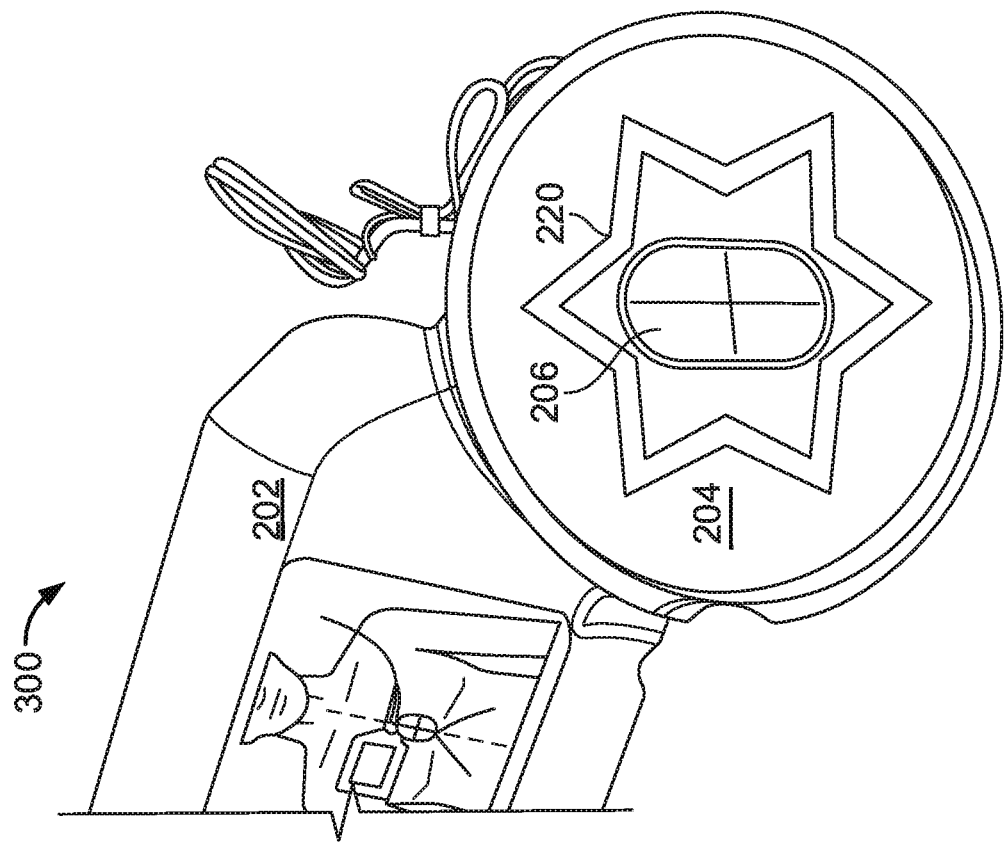

FIGS. 2S and 2T illustrate a top view and a perspective view of the middle layer 204c, respectively. The geometry and the composition material of the middle layer 204c can be selected to provide structural stability to the landing pad 204. The geometrical characteristics of the middle layer 204c can include substantially smooth top and bottom sides, a circular outer perimeter 250 and an inner perimeter 252. Both the outer perimeter 250 and the inner perimeter 252 of the middle layer 204c can be configured to correspond to outer boundaries 230, 244 and inner boundaries 232, 246 of the top layer 204a and the bottom layer 204b, respectively. The middle layer 204c can have a thickness of between 0.1 mm and 5.0 mm (e.g., approximately 1.4 mm), between 0.5 mm and 3.0 mm, between 1.0 mm and 2.0 mm, or any other suitable thickness. The composition material of the middle layer 204c can include a rigid (substantially inelastic) material such as plastic. For example, the middle layer 204c may be relatively more rigid as compared to the more compliant foam forming the top layer 204a and bottom layer 204b. As a result, the ACD device is able to remain situated on and adhered to the landing pad despite substantial force applied during pushing and pulling thereof. At the same time, as discussed above, the bottom layer 204b remains well adhered to the patient. Assisting such adherence are the wings 236 that are able to deflect away from the middle layer 204c and toward the patient. A pair of positioning tabs 240 can be located between the top layer 204a and the middle layer 204c, or at other locations of the landing pad structure. The positioning tabs 240 can be used to enable a rescuer to align the coupling surface 204 to the longitudinal axis of the chest of the patient 102.

FIGS. 3A-3D illustrate a plurality of examples of configurations 300 of the passageway 220 described with reference to FIGS. 2A-2D. In some implementations, the passageway 220 can have an oval cross-section (FIG. 3A), a circular or donut cross-section (FIG. 3B), a star-shaped cross-section (FIGS. 3C and 3D) or another suitable configuration that serves to enhance adherence between the active compression decompression device and the coupling surface. For example, the shape of the passageway 220 can be similar to the outer shape of the sensor 206 (FIG. 3A), it can be similar to the shape of the base of the applicator body (FIG. 3B) or it can be independent from both the shape of the sensor 206 and the shape of the base of the applicator body. In some implementations, the center of the passageway 220 is aligned with the geometrical center of the sensor 206, with the geometrical center of the coupling surface 204, and/or the geometrical center of the applicator body (e.g., applicator body 214 of the active compression decompression device 208). The passageway 220 may be suitable to distribute force between the active compression decompression device and the coupling surface such that force generated from pulling up of the device is transferred to regions outside of the passageway 220.

FIGS. 4A and 4B illustrate example cross-sections of the coupling surfaces 400a and 400b, respectively. The coupling surfaces 400a and 400b include a landing section 402, a sensor area 404, passageways 406, and an optional attachment member 408. The landing section 402 includes a core 402a, a top layer 402b, and external vertical walls 402c. The sensor area 404 includes a core 404a and a top layer 404b.

The passageways 406 include vertical walls 406a defining a gap between the landing section 402 and the sensor area 404. In some implementations, the vertical walls 406a are configured to maintain the passageways 406 open during each phase of the CPR treatment, such that the deformation of the coupling surfaces 400a and 400b under compression does not close the passageways 406. For example, the vertical walls 406a may have a comparatively lower elasticity than the landing section 402 and the sensor area 404.

As illustrated in FIG. 4B, in some implementations, the passageways 406 include an anti-sealing mechanism 406b and a filter 406c. The anti-sealing mechanism 406b can be configured to maintain the passageways 406 open during each phase of the CPR treatment. For example, the anti-sealing mechanism 406b can be configured to deform longitudinally and exhibits good radial strength under longitudinal compressive loads. The anti-sealing mechanism 406b can be a metallic tube or polymer formed by laser cutting a pattern of cylindrical rings and links in the tube, or a wire-based mesh having welds. The filter 406c can be a mesh filter, a baffle filter or any other type of air filter compatible with the function of the coupling surface 400b.

As illustrated in FIGS. 4A and 4B, in some implementations, the sensor area 404 includes one or more sensors 410 and wires 412 connected to the sensors 410. In some implementations, the sensors 410 can be attached to the bottom of the core 404a (FIG. 4A), within the core 404a, or adjacent to the top layer 404b (FIG. 4B). In some implementations, the top layer 404b can be configured to cover the sensors 410 and the wires 412, to prevent disconnection during CPR induced deformations.

Figure 5A:
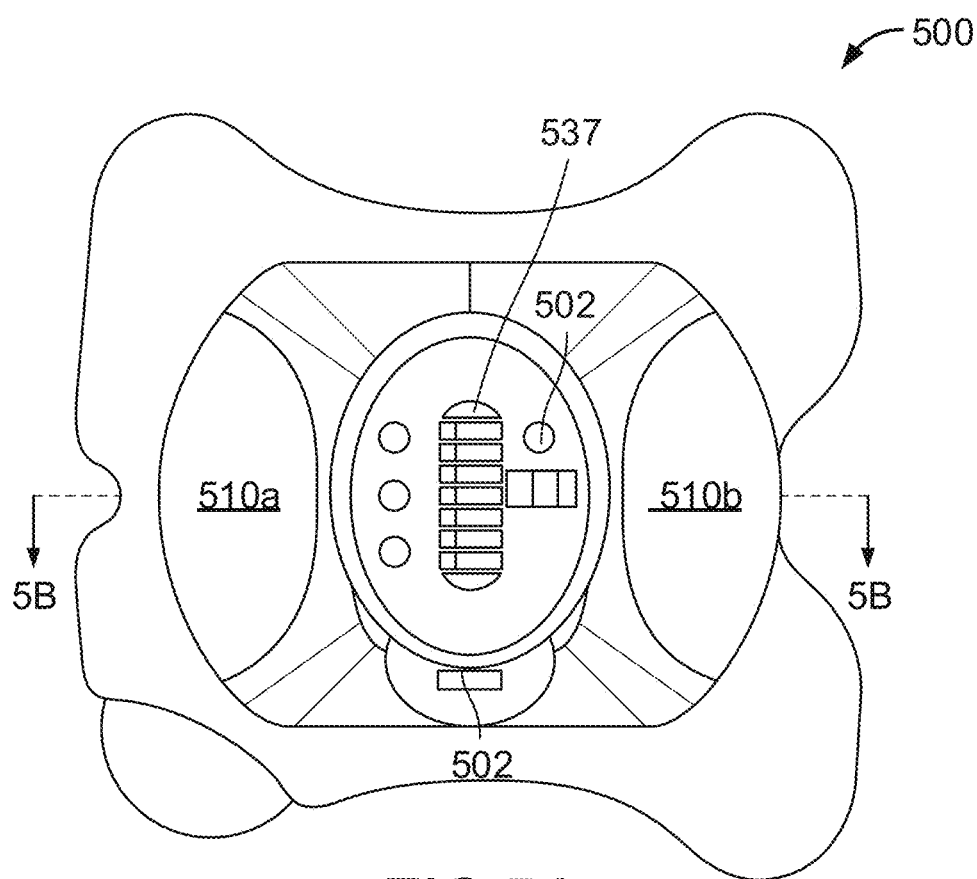
FIGS. 5A and 5B show top and cross-sectional views of an example active compression decompression device that maintains suction adherence.

FIG. 5A illustrates a top view of an example of an active compression decompression device 500 (e.g., active compression decompression device 208 in FIG. 2 or another type of active compression decompression device). The active compression decompression device 500 includes a handle 510 and an applicator body 530. The handle 510 has two handgrips 510a, 510b and a local feedback display 537. The active compression decompression device 500 can be configured for being used to assist with multiple CPR treatments. The active compression decompression device 500 can be switched on and turned off by pressing and holding down the power button 502 for a predetermined amount of time, for example 5 seconds. During this time, the local feedback display 537 can display the battery life remaining in hours. If the power button is not held for a sufficient amount of time (e.g. 5 seconds) the active compression decompression device 500 can remain on, and it automatically power off after 5 minutes if no compressions are sensed. It can be appreciated that such features are not necessary aspects of the present disclosure.

The active compression decompression device 500 can be configured to provide a predetermined number of hours of use. For example, the active compression decompression device 500 can be designed to provide about 30 hours of use. At any time, a rescuer can determine the remaining battery life by pressing and holding a power button. The local feedback display 537 can display the amount of time remaining, for example by displaying the letter H followed by a number. The number can indicate the number of hours of battery life remaining. In some implementations, the local feedback display 537 can display an alert when the active compression decompression device 500 has less than one hour of battery life remaining.

The handle 510 is attached to the applicator body 530. The applicator body 530 can be releasably attached to a coupling surface 522 (e.g., coupling surface 204 described with reference to FIG. 2). In some implementations, the applicator body 530 can be attached to the coupling surface 522 via a magnet. In some implementations, the magnetic coupling is configured such that applicator body 530 becomes detached from coupling surface 522 when excessive decompression force (upward pull) is applied. Other means to couple the applicator body 530 to the coupling surface 522 include various mechanical connections including ball and socket, cantilevered arm, or detent mechanism or the like.

Figure 5B:
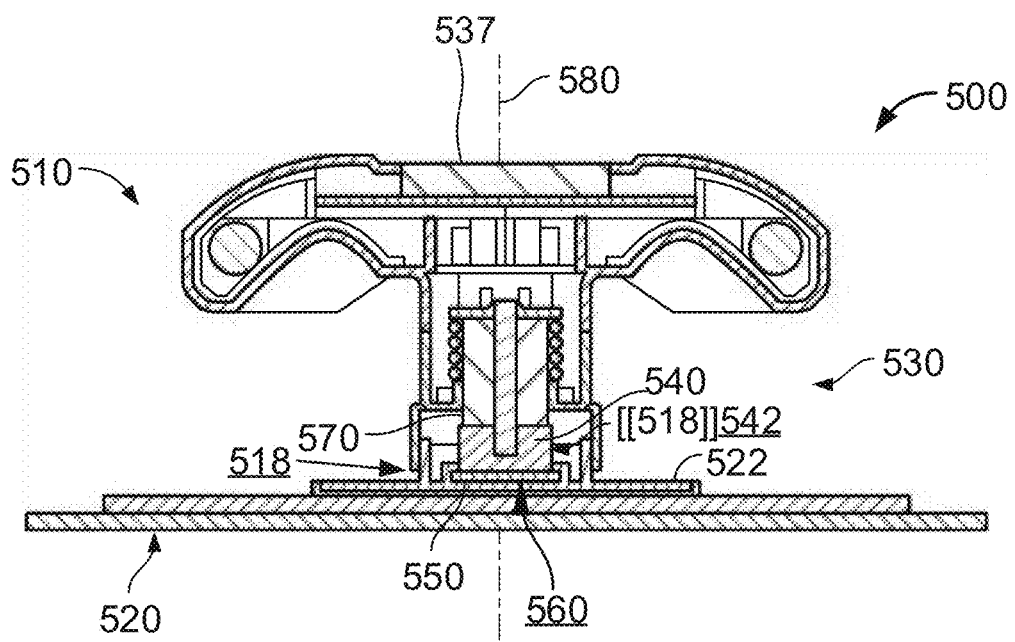

FIG. 5B illustrates an example of a magnetic coupling mechanism in an external chest compression and decompression system. FIG. 5B provides a cross-section view of compression and decompression the active compression decompression device 500, which includes an applicator body 530 releasably coupled to the coupling surface 522, which is attached to an adhesive pad 520. The active compression decompression device 500 can include a coupling mechanism between the coupling surface 522 and the applicator body 530. The coupling mechanism can include a magnet 540 and a magnet keeper 550. In some implementations, the magnet 540 can include or be part of a magnet assembly having a magnet, a non-ferrous spacer, and a ferrous container for directing the magnetic flux from the pole of the magnet furthest away from the magnet keeper to the magnet keeper. The poles of the magnet can be arranged such that the poles are aligned along the axis 580 of the system piston 570. The magnetic keeper 550 on the coupling surface 522 of the active compression decompression device 500 can include a magnet with poles arranged in the opposite direction of the system handle magnet or of a ferrous material such as 12L14 carbon steel having a high capacity for carrying magnetic flux. A magnetic coupling between the applicator body 530 and the coupling surface 522 can be effortless. In some implementations, the force of the disconnection of the magnetic coupling can be stable over a wide range of operating environments.

In some implementations, a magnetic coupler mechanism 518 can include a magnet assembly disposed on or coupled with the applicator body 530, and a keeper assembly disposed on or coupled with the coupling surface 522. For example, a magnetic coupler mechanism 518 can include magnet 540, or magnet assembly, and keeper assembly 550. The magnet 540 or magnet assembly can be coupled with (or part of) the applicator body 530. The keeper assembly 550 can be coupled with or part of the coupling surface 522. The magnet assembly and keeper assembly 550 in combination can be referred to as a coupler assembly. In some implementations, the coupler assembly can operate to provide a consistent release force allowing the applicator body 530 to separate from the coupling surface 522 prior to the adhesive pad releasing from the patient' skin 520. In addition, it may be desirable that the magnet assembly does not have a magnetic field that is widely dispersed, but rather focused in the direction of the keeper. To focus the magnetic field, the magnet assembly can include a magnetic core, a non-magnetic sleeve, and a ferromagnetic pot which conducts the magnetic flux from the pole on the enclosed side of the magnet to the open side of the magnet. The arrangement of a jacket with the magnet can focus the majority of the magnetic flux to the open end of the assembly. For example, the magnet assembly 560c may include a magnetic ore 540, a non-magnetic sleeve 542, and a ferromagnetic pot, which conducts the magnetic flux from the pole on the enclosed side 540 of the magnet to the open side 540 of the magnet. The arrangement of a jacket with the magnet can focus the majority of the magnetic flux to the open end of the assembly 560. Control or selection of the material properties of the keeper 550 can be helpful to achieve a consistent release force. In some implementations, the material can have a high magnetic saturation such as a 12L14 or American Iron and Steel Institute (AISI) 1010 or 1020 material and the magnetic properties of the material can be controlled through the control of material temper. For example, materials can be processed to a fully annealed condition. In addition to the magnetic coupling mechanism 518 described herein, other types of breakaway mechanisms can be used in an external chest compression and decompression for coupling the coupling surface 522 with the active compression decompression device 500. Examples of breakaway mechanisms can be configured to allow the active compression decompression device 500 to disengage from the coupling surface 522 in a controlled manner.

FIGS. 5C-5E illustrate examples of bottom views of the active compression decompression device 500. The bottom views include the applicator body 530 of the active compression decompression device 500 (e.g., applicator body 214 of the active compression decompression device 208 described with reference to FIG. 2). In some implementations, the applicator body 530 can be a plunger with structure that provides for a suitable suction adherence. The applicator body 530 includes a distal end 592 and a proximal end 594. The proximal end 594 defines the inner part of the applicator body 530. The distal end 592 defines the part of the applicator body 530 that impacts the patient's chest through the coupling surface 522. The applicator body 530 can include one or more check valves allowing fluid to escape the passageway during attachment to the coupling surface 522, but preventing fluid from entering the passageway via the check valves, enhancing adhering between the applicator body and the coupling surface. In some implementations, such check valve(s) may be provided with the coupling surface or other feature of the system for allowing fluid to escape the passageway and provide improved adhering between the applicator body and the coupling surface. The check valves include one or more of duckbill valves, umbrella valves, cross slit valves, ball-check valves, cone-check valves, and swing valves.

In some implementations, the applicator body 530 includes a compression pad 596. The compression pad 596 can be a flexible surface element configured to regulate the force applied to the patient's chest through the air passageway of the coupling surface. The compression pad 596 can include an adhesive layer. The compression pad 596 can include one or more suction cups 598 that apply compression and decompression forces to the patient's chest through the coupling surface 522. For example, in FIG. 5C, the applicator body 530 forms a large suction cup surrounding the compression pad. Or, as shown in FIGS. 5D and 5E, the compression pad itself may include one or more additional suction cups. In some cases, the adhesive layer can line the margins of the suction cups 598. The compression pad 596 can be secured to the coupling surface 522 by suction created by the suction cups 598 formed on distal end 592. A rescuer can pull back the active compression decompression device 500, which in response extends the applicator body 530, to confirm secure coupling between the compression pad 596 and the coupling surface 522.

The compression pad 596 has a stiffness that increases from margins towards a geometrical center of the compression pad 596. The compression pad 596 can present any suitable complex shape, including multiple appendages, arms or lobes. Each arm or lobe of the compression pad 596 can optionally contain numerous suction cups 598. The use of multiple lobes enables the compression pad 596 with many suction cups 598 to conform to irregularities in the top layer of the coupling surface 522 (e.g., irregularities due to sensor and wire inclusions). The lobes of the compression pad can be conformable and inelastic to convey the decompression force between active compression decompression device 500 and the coupling surface 522.

In some implementations, the size and/or shape of the suction cups 598 can be selected based on one or more characteristics of the coupling surface 522. In some implementations, the number and the location of the suction cups 598 can be selected based on one or more characteristics of the coupling surface 522. For example, the suction cups 598 can be arranged in two groups 598a and 598b, distanced from each other, such that no suction cup covers the passageway of the coupling surface 522 during coupling between the compression pad 596 and the coupling surface 522.

Figure 6B:
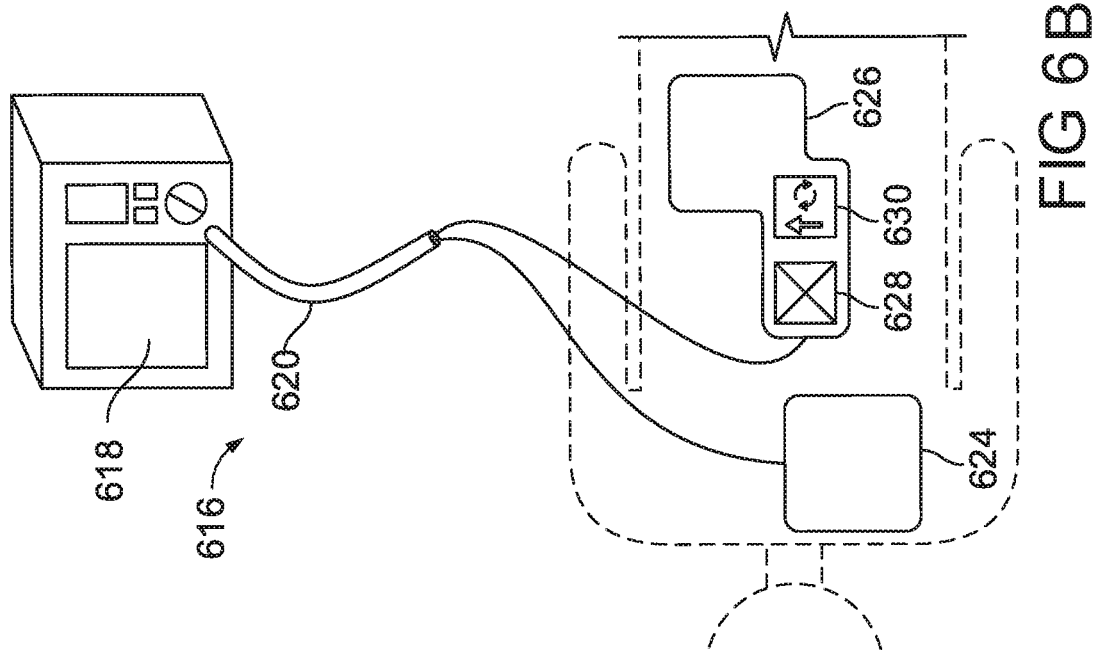
FIGS. 6A and 6B show a portable defibrillator and ancillary components arranged to provide feedback and instruction to rescuers in accordance with certain implementations.
Figure 6A:
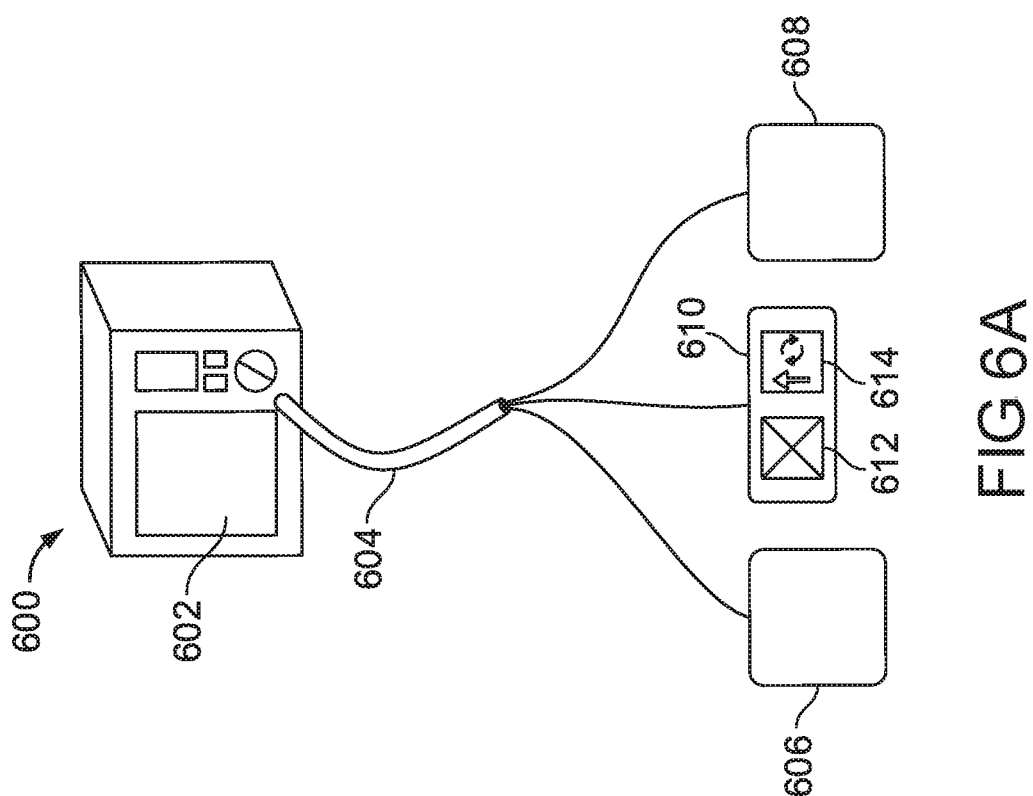

Referring to FIG. 6A, an example system 600 is shown, in which a defibrillator 602, including a standard configuration, is upgraded to provide an additional user feedback functionality. The defibrillator 602 is connected to an electrode assembly by way of a wiring harness 604. The wiring harness 604 can include a number of wire leads that are connected together by a common plastic shroud that can surround the wires or can have been integrally formed around the wires such as through an extrusion process, and can be connected to the defibrillator 602 by way of a single plug. For example, the defibrillator 602 can be provided with a female or male connection, and the plug can be provided with a corresponding connection in a manner that is well known in the art. The wires can carry power from the defibrillator 602, such as current to provide a shock to a patient who is being provided with emergency care, or to the defibrillator 602, such as in the form of signals for generating ECG information, accelerometer information, and measurements of trans-thoracic impedance of a patient.

The electrode assembly in this example includes a first electrode 606, a second electrode 608, and a chest compression assembly 610. The first electrode 606 can be configured to be placed above the patient's right breast, while the second electrode 608 can be configured to be placed below the patient's left breast. During a rescue operation, printed insignia on one or both of the electrodes 606, 608 can indicate to a rescuer how to deploy the electrodes 606, 608, and where each of them should be placed. In addition, the defibrillator 602 can display such instructions on a graphical display and can also provide verbal instructions to supplement was is shown in the visual instructions, such as instructions for the sequential operation of the defibrillator.

The chest compression assembly 610, in this example, includes a detector 612 and a display 614. The detector 612 can include a plastic housing within which is mounted an accelerator assembly. The accelerator assembly can move with the housing as chest compressions and decompressions are performed on a patient so that motion of the accelerometer matches motion of the patient's sternum. The detector 612 is shown in the figure as having an "X" printed on its top surface to indicate to the rescuer where to place his or her hands when delivering chest compressions and decompressions to a patient. The accelerator in the housing can be connected to pass signals through harness 604 to defibrillator 602 (or can include a wireless transceiver for passing the information wirelessly), which can be provided with circuitry and or software for converting such signals into the indications about the rate and depth of compressions and decompressions being performed on the patient, in manners such as those described below.

The display 614 can provide feedback that is directed to the rescuer who is performing chest compressions and decompressions. In this example, the feedback comprises symbols similar to those shown on the display of defibrillator 112 in FIG. 1, in particular, a real-time representation of the rescuer who performs chest compressions and decompressions synchronously displayed with an optimized rescuer position. The representation can be selected to be independent of the orientation from which it is viewed, so that it has the same meaning to a rescuer who is on the right side of the patient as to a rescuer who is on the left side of the patient. In that manner, the system 600 does not need to determine where the rescuer is positioned. Also, a haptic vibrating mechanism can be provided at the assembly 610, so as to provide tactile beats or metronomes for a user to follow in providing chest compressions and decompressions.

FIG. 6B shows a slightly different arrangement in a system 616 that includes a defibrillator 618 that is the same as defibrillator 602. In actual implementation also, the same defibrillator could be used with two different types of electrode assemblies like those shown in FIGS. 6A and 6B. With specific reference to FIG. 6B, a wiring harness 620 in this example can be the same as wiring harness 604 in FIG. 6A, though here it connects defibrillator 618 to an electrode 624, and an assembly 626. The electrode 624 can simply be a single electrode that is connected to receive energy from the defibrillator 618, and is arranged to be placed in a conventional manner above a patient's right breast. The electrode 624 can also include mechanisms for sensing an ECG reading from a patient, and for communicating sensed parameters back to the defibrillator 618.

The assembly 626 can present a slightly L-shaped form, with one leg comprising an electrode designed to be placed below a patient's left breast, and another leg arranged to lie in a line with the patient's sternum. The assembly can be mounted on a flexible foam layer that includes a gel layer on the bottom of the electrode for conducting a shocking pulse to a patient, but no gel under the sensor portion. However, the sensor portion can have a form of adhesive on its bottom side so that the accelerometer does not bounce and separate from the patient during chest compressions and decompressions, and thus give an inaccurate reading to the defibrillator 618.

In this example, the hypothetical patient is shown in dotted lines to indicate how the electrode 624 and the assembly 626 can be positioned in actual use. Before they are deployed, however, the various electrodes and assemblies can be stored in a sealed packet, and the wires can be coiled to reduce needed space, in conventional manners. At the time of an emergency, the wires can have already been plugged into the defibrillator (e.g., via the wires extending through a sealed hole out of a packet in which the electrodes are stored to keep their gels moist). A rescuer can then open the package, plug the wires in if they are not already plugged in, and if necessary, read instructions on the back sides of the electrodes regarding the proper manner to apply the electrodes (e.g., with graphics that show the peeling off of covers over the electrode gels and also show images of the proper placement of the electrodes on a line-drawn patient).

In addition to electrodes, the assembly 626 can include a sensor assembly 628 and a display 630, similar to the sensor assembly 612 and display 614 in FIG. 6A. In addition, the components that provide functionality of the assembly 628 and display 630 can be the same as those described above for assembly 612 and display 614 in FIG. 6A. In this example, though, the assembly 628 and display 630 are connected directly to the electrode 626 by flexible structures that are arranged and sized so as to place the electrode and sensors in appropriate locations for a patient (under a left breast and aligned over the top of the sternum). Such an arrangement allows the system 616 to have fewer components that need to be applied to a patient than the system 600, while still having the flexibility to space the two electrodes relative to each other depending on the size of the patient (e.g., because the electrodes are separate from each other, it can be easier to position them both on small patients and very tall/long patients).

In both of the systems 600, 616, the placement of a display near the hands of a rescuer can provide one of more benefits in some implementations. For example, a rescuer is typically looking at his or her hands when applying chest compressions and decompressions, both because it is most natural to look forward, and as a mechanism to obtain feedback on how deep the chest compressions and decompressions are and how the patient is doing. Thus, the rescuer can see the feedback without having to look around, and can constantly receive the feedback even while performing chest compressions and decompressions. Also, the components can be provided in such locations conveniently and with relatively low cost, since the electrodes and accelerometers will already be provided, and a display need simply be added to one of these existing components (though in other implementations, the display can be located elsewhere). The feedback device also is naturally positioned to provide haptic feedback, which might be more directly processed by a rescuer. And by using visual feedback that is in the field of view of a particular rescuer and using haptic feedback, the system can reduce "attention pollution" at a scene, in that is lessens the level of noise and other distractions that other rescuers have to deal with in a very stressful environment.

Feedback devices away from the main medical device can also take other forms. For example, an LED can simply be provided in the top surface of one of the electrodes or near a puck, and the LED can blink to indicate a rate of chest compressions and decompressions to be performed, and stay solid on to indicate that rescuers should switch positions. Also, an LED or graphical display can be provided on the ventilation bag 612, such as to blink to indicate a rate at which the bag is to be squeezed, and can be made solid in coordination with a display for the person performing chest compressions and decompressions being made solid. In other words, the same signal can be provided to each of the rescuers to switch places, though on the respective subsystem that they are currently operating. As a result, the rescuers will only need to know a single "change" signal and will be able to react more intuitively and more quickly.

Figure 6C:
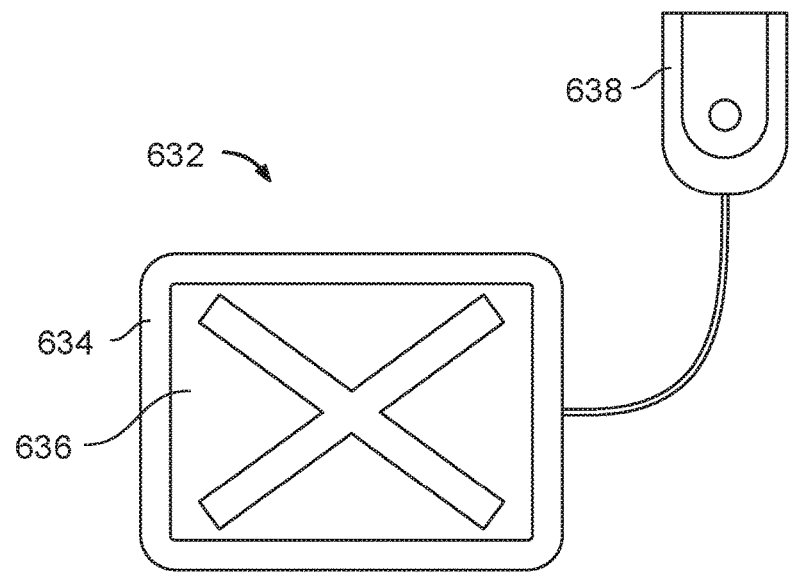
FIGS. 6C-6E show chest compression pucks that can capture information provide from activities of a rescuer in accordance with certain implementations.
Figures 6D, 6E:
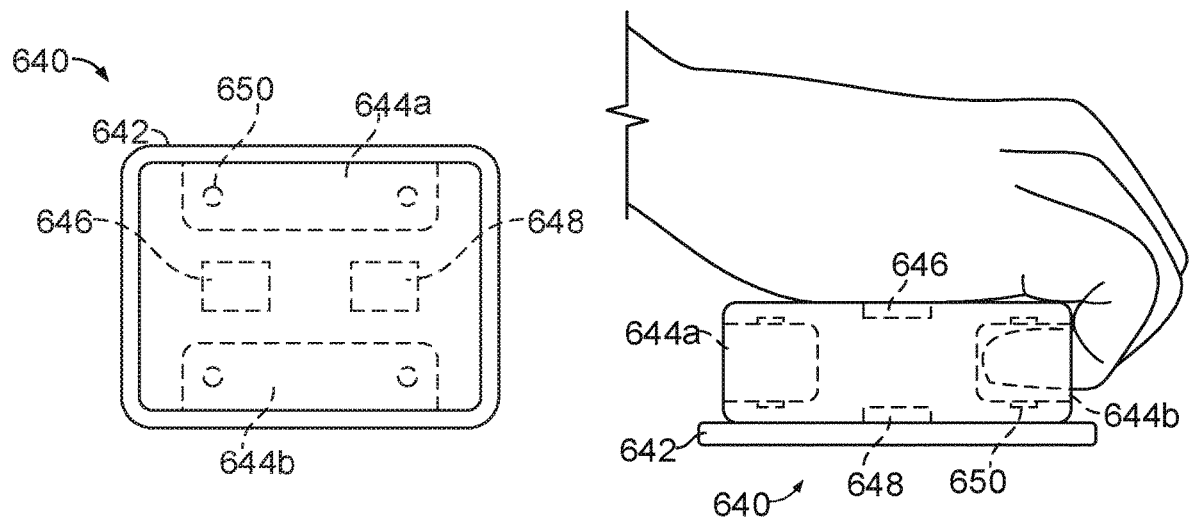

FIGS. 6C-6E show chest compression pucks that can capture information from a rescuer. In general, typical pulse oximetry sensor components can be integrated into a device on or in which a rescuer places his or her fingers, and can be used to provide a connected (wired or wirelessly) medical device such as a defibrillator, with indications of the blood oxygen level and pulse rate of a rescuer holding the device, which in these examples can be referred to as a CPR puck. The pucks shown in FIGS. 6C-6E can be provided as part of the systems also shown in FIGS. 6A and 6B, such as by integrating the components for sensing rescuer condition into the components in those other figures.

Referring now specifically to FIG. 6C, there is shown an assembly 632 made up of a puck housing 636 and substrate 634. The substrate 634 can have on its lower side a gel-based adhesive so that the assembly 632 adheres to the chest of a patient on which it is placed. The housing 636 can in turn be solidly adhere to the top of the substrate 634 do that the housing 636 moves with a patient's sternum when a rescuer places his or her hands on top of the "X" shown on the top surface of the housing 636 and performs chest compressions and decompressions. Connected to the substrate 634 and/or housing 636 by wire is a pulse oximeter 638. The pulse oximeter can report a blood oxygen level and pulse rate through the wire from which it is attached into the remainder of the assembly 632, from which it can be reported to a defibrillator or other medical device, either wirelessly or by wired connection.

In operation, when a rescuer begins performing chest compressions and decompressions, he or she can be instructed to slip a fingertip into the pulse oximeter 638 before placing his or her palms on top of the housing 336. The wire can permit movement of the rescuer's fingertip as they perform chest compressions and decompressions, while measuring the relevant values. Such values can then be used, as discussed above, along with other factors such as rate and depth of compressions and decompressions, to determine when the rescuer should be instructed to stop performing chest compressions and decompressions and yield to another rescuer. Also, the assembly 632 can be provided as a stand-alone unit separate from a defibrillator or other medical, so as to provide more general feedback to a rescuer, where the feedback integrates consideration of rescuer blood oxygen level, pulse, or both.

Referring to FIGS. 6D and 6E, there is shown a top and side section view of an assembly 640 that is similar to assembly 632 in FIG. 6C, but integrates sensing functionality for the rescuer into the puck housing.

Again, the housing is shown on top of an adhesive substrate 642, but in this example, the housing is provided with depressions 644a, 644b into which a rescuer can slide his or her fingertips while performing chest compressions and decompressions, as shown by the hand in FIG. 6E. The housing is provided with depressions 644a, 644b on opposed sides, so that rescuers on both sides of a patient can use the assembly 640 and take advantage of its rescuer monitoring functionality. Also, as shown, sensors 650 can be provided at multiple locations, including four different locations to reflect rescuers who can be on either side of the patient and can places fingers from their right or left hands into the depressions 644a, 644b.

The assembly can simply send signals back to a medical device such as a defibrillator. Separately, the assembly 640 can modify or analyze the signals right on the assembly 640 in the housing. Thus, for example, an oximeter processor 648 is shown inside the housing and can receive signals from the sensors 650 and convert them partially or fully into blood oxygen and pulse rate values that can then be displayed or further processed on the assembly 640 (e.g., to identify that the rescuer is becoming fatigued). Similarly, an accelerometer pack 646 can be provided inside the housing in a position so as to sense proper motion of the patient's sternum. The pack 646 can, for example, compute depths of compressions and decompressions and rates of compressions and decompressions, and can also be connected to an output mechanism on the assembly 640 or connected to a medical device that is separate from the assembly 640 so as to provide chest compression feedback in manners like those discussed above and below.

Figure 7:
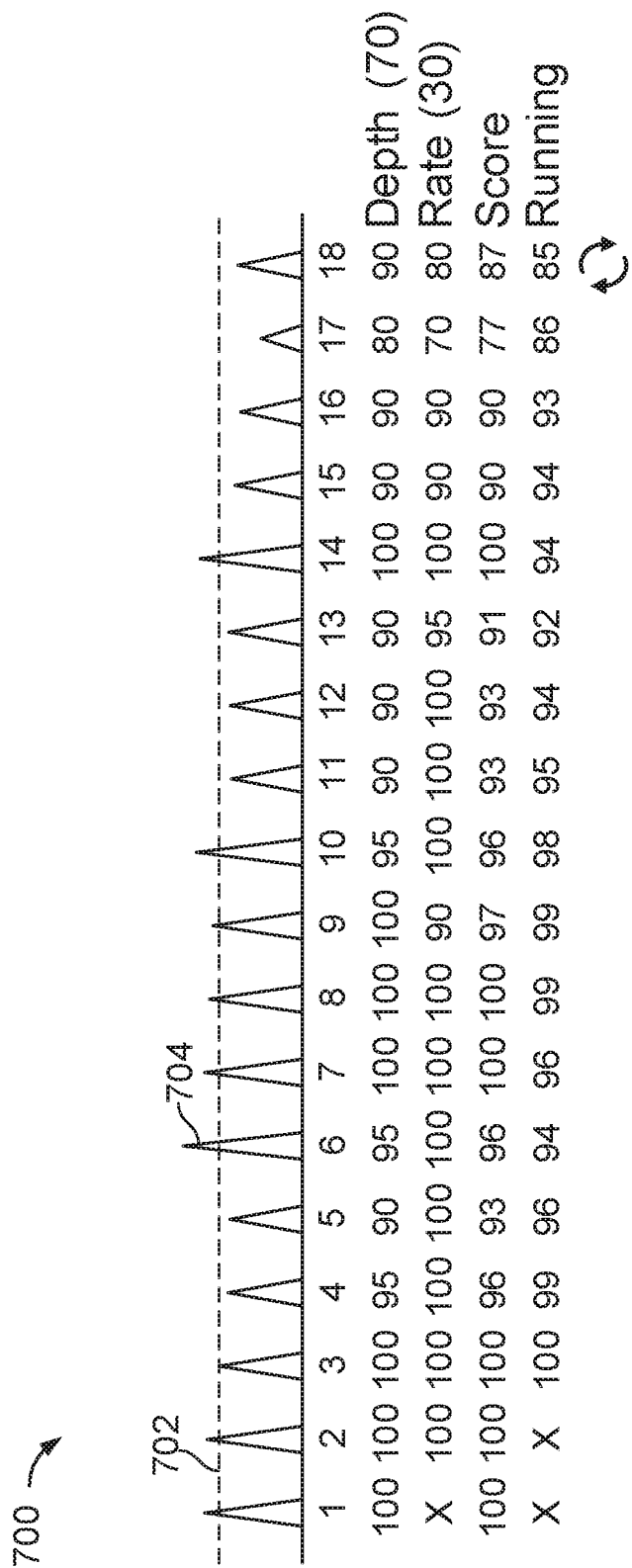
FIG. 7 shows example chest compression inputs and mechanisms for analyzing the inputs to determine whether a different person should provide chest compressions.

FIG. 7 shows example chest compression inputs and mechanisms for analyzing the inputs to determine whether a different rescuer should provide chest compressions and decompressions. In general, the illustrated example includes a series of eighteen chest compressions and decompressions 700 that have been graphed along a horizontal time axis, along with a variety of numbers that represent parameters of how the chest compressions and decompressions were performed. Such sensed compression data and derived numbers can then be used to determine when the quality of the chest compressions and decompressions indicates that the rescuer is getting fatigued and cannot maintain the optimized CPR technique identified by the system, and the system should indicate to the rescuer that they should switch with another, fresher rescuer.

Referring more specifically to the graphed compressions and decompressions, a dashed line 702 represents a target chest compression depth. Each of the spikes 704 indicate a distance level of downward compression (y axis), graphed according to time (x axis). In particular, the compressions and decompressions are sharp motions followed by pauses, with the overall pattern repeated eighteen times during the time (which can be a fraction of a minute when the rescuer is performing about 100 compressions and decompressions per minute). Such compressions and decompressions can be sensed by an accelerometer assembly that is between the hands of the rescuer performing chest compressions and decompressions and the sternum of the patient. Sensed signals can then be passed through a wiring harness to circuitry and software in a defibrillator or other medical device that can analyze the signals to identified compression depths and timing of the chest compressions and decompressions.

As can be seen, the initial chest compressions and decompressions are at an appropriate level and an appropriate rate, but began to dip at the fourth and fifth compressions and decompressions. The compressions and decompressions then pick up and hit the dashed line 702, perhaps because the fall in compressions and decompressions caused a defibrillator to indicate to a rescuer that they should compress harder, and the user followed such direction. The depth of compressions and decompressions over time then falls again at compressions and decompressions 11, 12, and 13, but then picks up at 14 and falls yet again near the end, indicating that the user has become fatigued.

Below the graph are shown numbers that, for this example, indicate values that can be computed by a defibrillator that is connected to a system for determining when to signal that a provider of chest compressions and decompressions to a patient should be changed by the system. The top row shows a score that can be given to a user to rate the quality of the depth of the chest compressions and decompressions. Such a score can be given a baseline of 100 around a depth that approximates the desired line of 702. The score can fall the further one gets from line 702, though the score can fall more quickly for deviations on the under-compression side than the over-compression side, e.g., if a determination is made that under-compression is a more serious error than over-compression. Thus, for example, the fifth compression falls below line 702 by an amount less than the sixth compression falls above the line, but the fifth compression receives a lower score than does the sixth compression.

In this example, the depth of compression factor is provided 70% of a weighting in determining an overall score for the quality of the chest compression. The other 70% of the score is driven by the rate at which the user provides the compressions and decompressions. Thus, for example, one can see fairly even spacing for compressions two through eight, but a slight delay for compression nine, so that the ninth compression receives a score of 90 instead of a score of 100. In addition, one can see lengthening delays between compressions and decompressions at the end of the period. The rate scores reflect, in each instance, how far a compression was performed from the time at which it was supposed to be performed according to protocol. Again, the scores are scaled to a maximum of 100 for ease of explanation, but could take other forms also.

The third line in the numbers indicates an overall score for each of the compressions and decompressions, where the overall score is simply the combined weighted value of the two component scores for depth and rate, respectively. Finally, the fourth line shows a running score that is a running average of the current score and the two previous scores. By using a running average, singular deviations from a perfect compression can be ignored, while lingering deviations can be captured so that continual failure by a user, which indicates fatigue of the user, can result in the generation of a signal to switch users in performing chest compressions and decompressions. Thus, for example, compression number five is a bad compression, but the running score is relatively high because the previous two compressions and decompressions were better.

In this example, the trigger for generating an indication that users should change position is a running score at or below 85. Thus, although the running score in the example rises and falls as a user has periodic problems with performing compressions and decompressions, it does not fall to the triggering level until compression eighteen, after there had been three weak compressions and decompressions in a row that were also spaced too far apart—so that the running average score really fell. In actual implementation, software can monitor the value as a user provides compressions and decompressions, can periodically update the value (e.g., once for each compression or on another basis), and can cause a defibrillator, such as defibrillator 112, to emit output to one or more rescuers to indicate the need for a change, such as the indication shown in the prior figures above.

While the particular running average scoring technique described is provided for its simplicity and ease of understanding, different approaches can be used to identify when a user is likely becoming too fatigued to maintain quality chest compressions and decompressions or other components of CPR treatment. For example, various inputs can be subjected to derivations in order to determine rates of change of those inputs. An indication to change rescuers can be generated when the rate of change in the quality of performance exceeds a preset amount in a negative direction. Also, models can be generated to represent fatigued users, and actual inputs can be compared to such models to indicate when fatigue is setting in for a real user and to cause an alert to be generated.

In some instances, such as when the number of rescuers is known, data can be stored across multiple cycles of chest compression sessions for each of the users. For example, the system can identify in early cycles of a rescue that one of the rescuers has a sudden drop-off in chest compression performance but then recovers, and can store such understanding and use it in subsequent cycles so as to not trigger an indication to change rescuers simply because the particular rescuer is having momentary problems. Another rescuer can be seen to have a slower drop in performance but can be more erratic in his provision of chest compressions and decompressions, so that a system can permit more variability before it triggers an indication to switch rescuers, since variability by that user can not indicate fatigue, but can simply be standard variability in the manner in which the user performs chest compressions and decompressions. Other factors can also be taken into account in addition to depth and rate of providing chest compressions and decompressions. For example, a heart rate monitor can be applied to a rescuer and an increase in heart rate can indicate fatigue by the rescuer, and can be used to generate a signal to switch rescuers. Also, the shape of a compression profile can be used, such that a jerky or sharp profile can indicate fatigue by a user, and also contribute to the triggering of a signal to switch rescuers.

Figure 8:
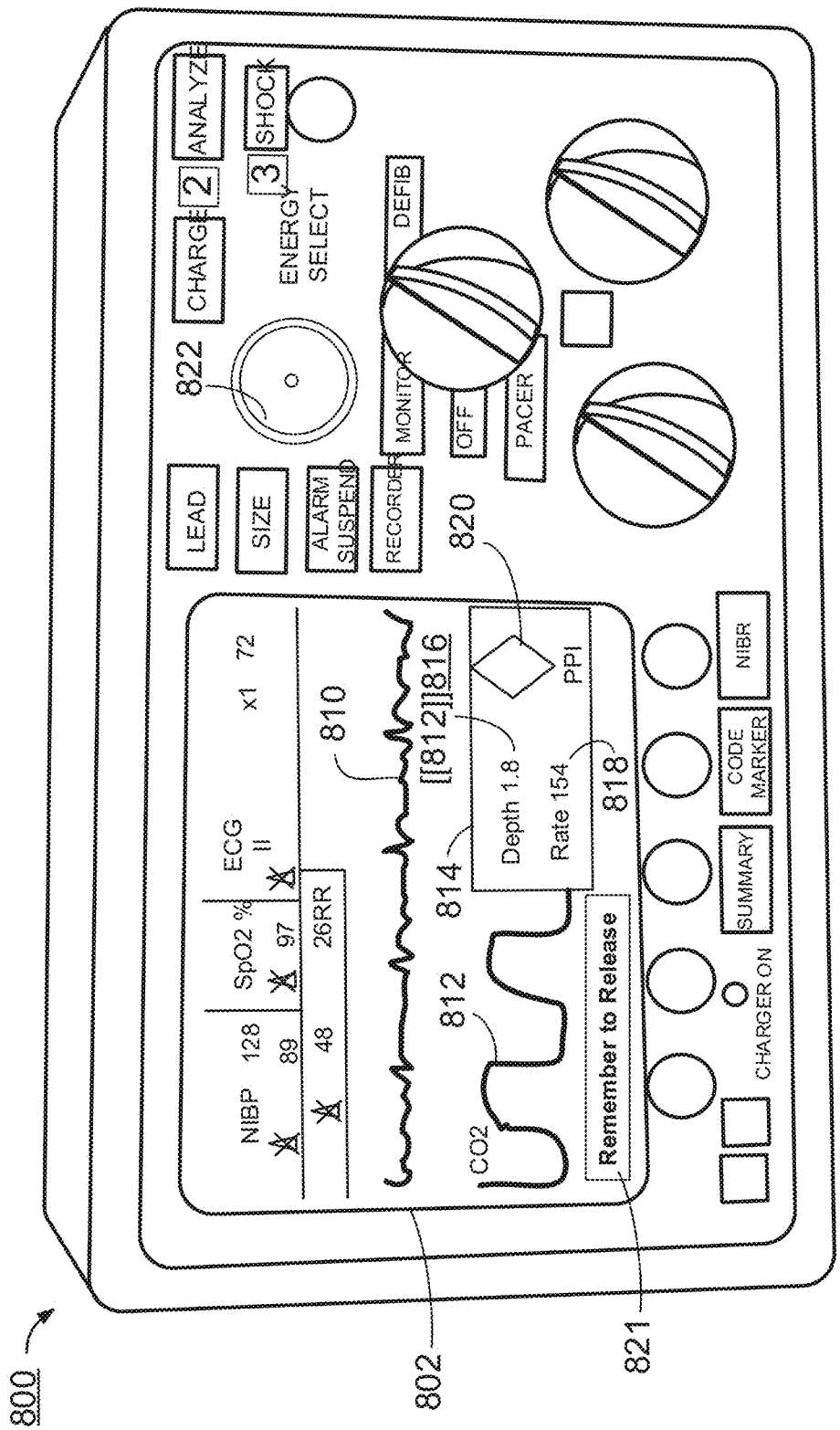
FIG. 8 illustrates a defibrillator showing some types of information that can be displayed to a rescuer.

As illustrated in FIG. 8, a defibrillator or a computing device 800 including a display can provide real-time feedback to the rescuers. For illustrative purposes, two particular examples of feedback are shown on a display 802 of the defibrillator 800 (e.g., defibrillator 112 described with reference to FIG. 1). FIG. 8 shows a defibrillator showing some types of information that can be displayed to a rescuer. In the figure, a defibrillation device 800 with a display portion 802 provides information about patient status and CPR administration quality during the use of the defibrillator device. As shown on display 802, during the administration of chest compressions and decompressions, the device 800 displays information about the chest compressions and decompressions in box 814 on the same display as is displayed a filtered ECG waveform 810 and a CO2 waveform 812 (alternatively, an SpO2 waveform can be displayed).

During chest compressions and decompressions, the ECG waveform is generated by gathering ECG data points and accelerometer readings, and filtering the motion-induced (e.g., CPR-induced) noise out of the ECG waveform. Measurement of velocity or acceleration of chest compression during chest compressions can be performed according to the techniques taught by U.S. Pat. No. 7,220,335, titled Method and Apparatus for Enhancement of Chest Compressions during Chest Compressions, the contents of which are hereby incorporated by reference in their entirety. Displaying the filtered ECG waveform helps a rescuer reduce interruptions in CPR because the displayed waveform is easier for the rescuer to decipher. If the ECG waveform is not filtered, artifacts from manual chest compressions and decompressions can make it difficult to discern the presence of an organized heart rhythm unless compressions and decompressions are halted. Filtering out these artifacts can allow rescuers to view the underlying rhythm without stopping chest compressions and decompressions.

The CPR information in box 814 is automatically displayed when compressions and decompressions are detected by a defibrillator. The information about the chest compressions and decompressions that is displayed in box 814 includes rate 818 (e.g., number of compressions and decompressions per minute) and depth 816 (e.g., depth of compressions and decompressions in inches or millimeters). The rate and depth of compressions and decompressions can be determined by analyzing accelerometer readings. Displaying the actual rate and depth data (in addition to, or instead of, an indication of whether the values are within or outside of an acceptable range) can also provide useful feedback to the rescuer. For example, if an acceptable range for chest compression depth is 25 to 60 mm, providing the rescuer with an indication that his/her compressions and decompressions are only 15 mm can allow the rescuer to determine how to correctly modify his/her administration of the chest compressions and decompressions (e.g., he or she can know how much to increase effort, and not merely that effort should be increased some unknown amount).

The information about the chest compressions and decompressions that is displayed in box 814 also includes a perfusion performance indicator (PPI) 820. The PPI 820 is a shape (e.g., a diamond) with the amount of fill that is in the shape differing over time to provide feedback about both the rate and depth of the compressions and decompressions. When CPR is being performed adequately, for example, at a rate of about 100 compressions and decompressions per minute (CPM) with the depth of each compression greater than 40 mm, the entire indicator will be filled. As the rate and/or depth decreases below acceptable limits, the amount of fill lessens. The PPI 820 provides a visual indication of the quality of the CPR such that the rescuer can aim to keep the PPI 820 completely filled.

As shown in display 802, the filtered ECG waveform 810 is a full-length waveform that fills the entire span of the display device, while the second waveform (e.g., the CO2 waveform 812) is a partial-length waveform and fills only a portion of the display. A portion of the display beside the second waveform provides the CPR information in box 814. For example, the display splits the horizontal area for the second waveform in half, displaying waveform 812 on left, and CPR information on the right in box 814.

The data displayed to the rescuer can change based on the actions of the rescuer. For example, the data displayed can change based on whether the rescuer is currently administering CPR chest compressions and decompressions to the patient. Additionally, the ECG data displayed to the user can change based on the detection of CPR chest compressions and decompressions. For example, an adaptive filter can automatically turn ON or OFF based on detection of whether CPR is currently being performed. When the filter is on (during chest compressions and decompressions), the filtered ECG data is displayed and when the filter is off (during periods when chest compressions and decompressions are not being administered), unfiltered ECG data is displayed. An indication of whether the filtered or unfiltered ECG data is displayed can be included with the waveform.

Also shown on the display is a reminder 821 regarding "release" in performing chest compression. Specifically, a fatigued rescuer can begin leaning forward on the chest of a patient and not release pressure on the sternum of the patient at the top of each compression. This can reduce the perfusion and circulation accomplished by the chest compressions and decompressions. The reminder 821 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication can be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback. For example, the defibrillator 112 can emit a sound through speaker 822 in the form of a metronome to guide the rescuer 106a in the proper rate of applying CPR treatment.

Figure 9A:
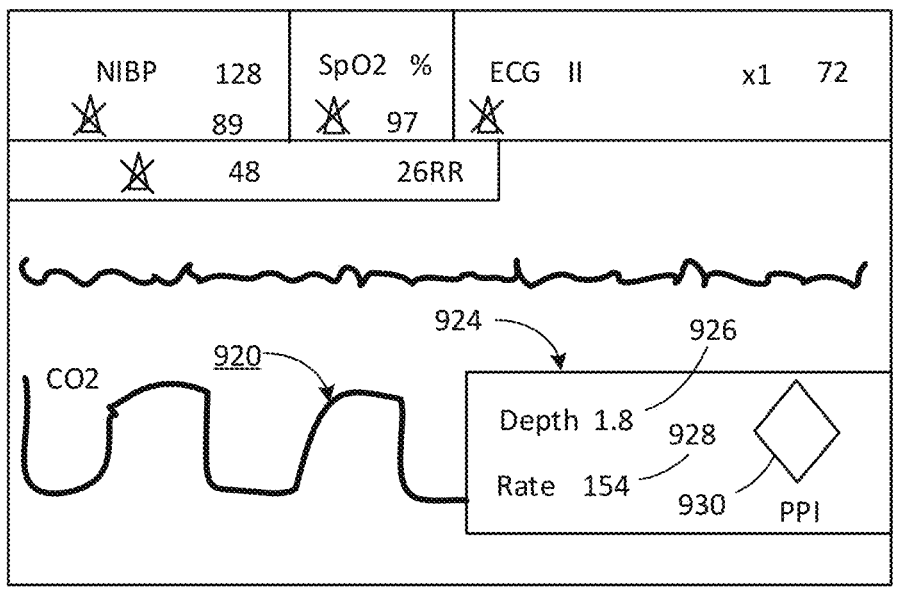
FIGS. 9A-9C show screenshots of a defibrillator display that provides feedback concerning chest compressions performed on a patient.
Figure 9B:
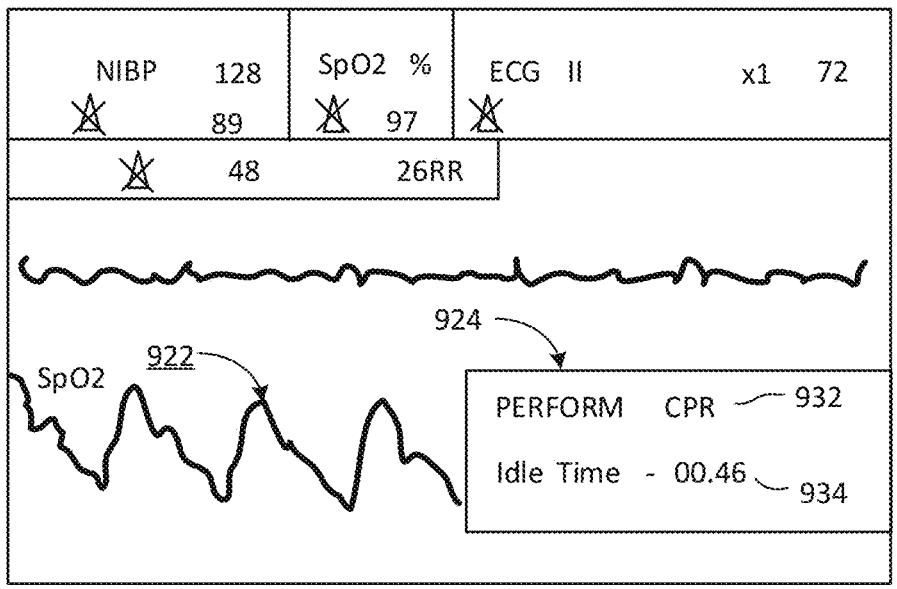
Figure 9C:
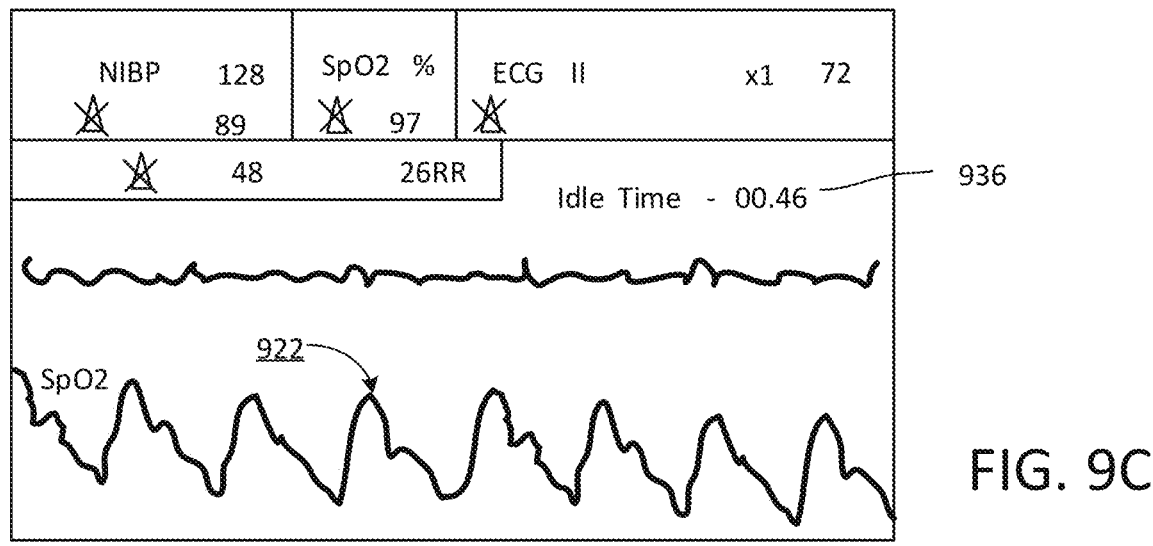

FIGS. 9A-9C show example screens that can be displayed to a rescuer on a defibrillator. Each of the displays can be supplemented with a display like box 602 in FIGS. 6A and 6B when the defibrillator determines that rescuers providing some component of care (e.g., chest compressions and decompressions) should be changed.

FIG. 9A shows exemplary information displayed during the administration of CPR chest compressions and decompressions, while FIGS. 9B and 9C show exemplary information displayed when CPR chest compressions and decompressions are not being sensed by the defibrillator. The defibrillator automatically switches the information presented based on whether chest compressions and decompressions are detected. An exemplary modification of the information presented on the display can include automatically switching one or more waveforms that the defibrillator displays. In one example, the type of measurement displayed can be modified based on the presence or absence of chest compressions and decompressions. For example, CO2 or depth of chest compressions and decompressions can be displayed (e.g., a CO2 waveform 920 is displayed in FIG. 9A) during CPR administration, and upon detection of the cessation of chest compressions and decompressions, the waveform can be switched to display a $SpO_2$ or pulse waveform (e.g., a $SpO_2$ waveform 922 is displayed in FIG. 9B).

Another exemplary modification of the information presented on the display can include automatically adding/removing the CPR information from the display upon detection of the presence or absence of chest compressions and decompressions. As shown in FIG. 9A, when chest compressions and decompressions are detected, a portion 924 of the display includes information about the CPR such as depth 926, rate 928, and PPI 930. As shown in FIG. 9B, when CPR is halted and the system detects the absence of CPR chest compressions and decompressions, the defibrillator changes the CPR information in the portion 924 of the display, to include an indication 932 that the rescuer should resume CPR, and an indication 934 of the idle time since chest compressions and decompressions were last detected. In a similar manner, when the defibrillator determines that rescuers should change, the label 932 can change to a message such as "Change Who is Administering CPR." In some implementations, as shown in FIG. 9C, when CPR is halted, the defibrillation device can remove the portion of the display 924 previously showing CPR data and can display a full view of the second waveform. Additionally, information about the idle time 936 can be presented on another portion of the display.

Figure 10A:
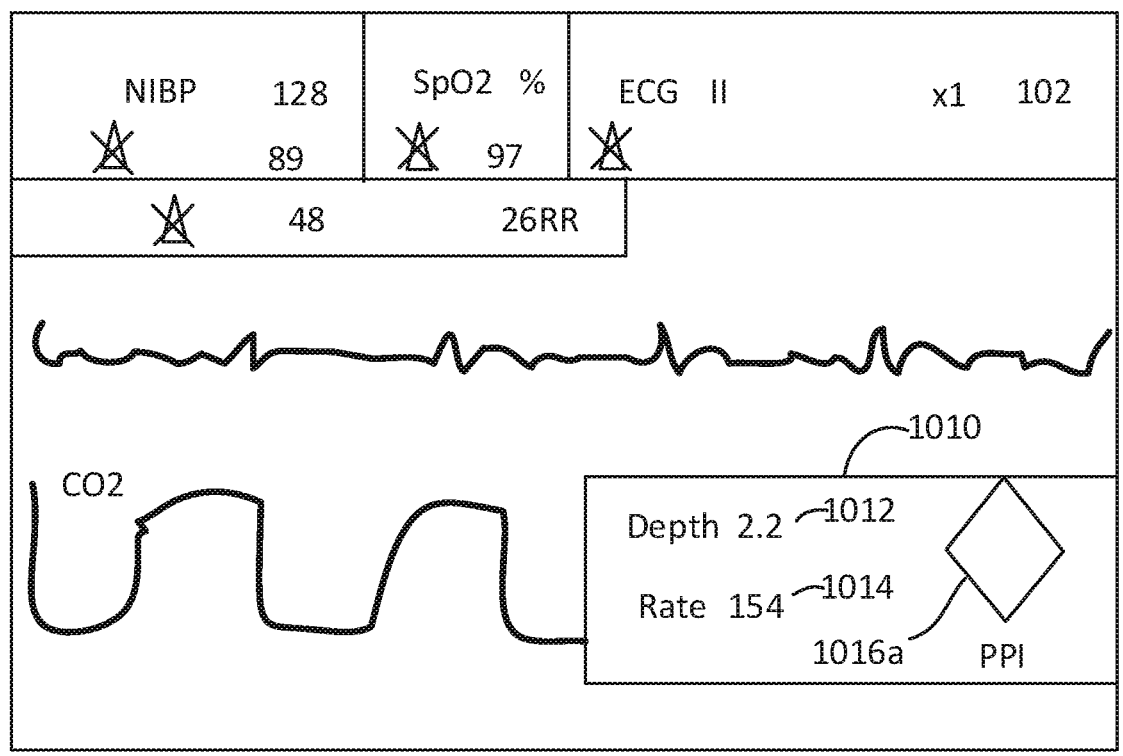
FIGS. 10A and 10B show screenshots providing feedback regarding a perfusion index created form chest compressions.
Figure 10B:
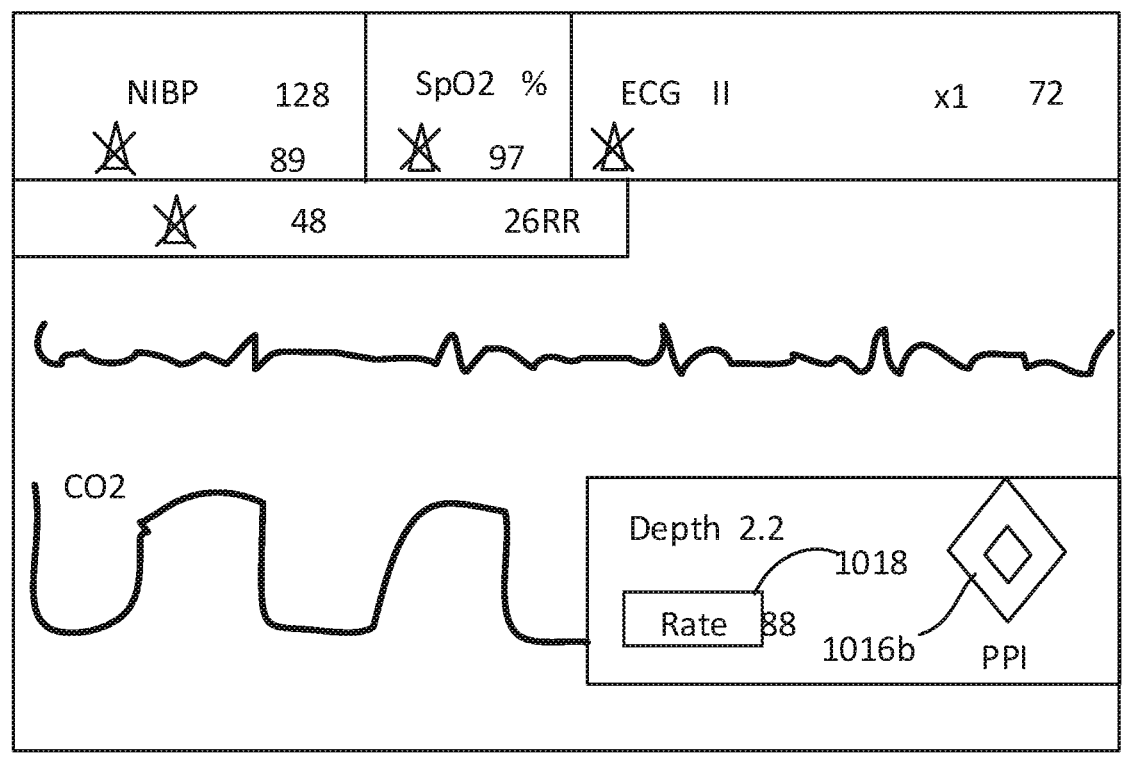

FIGS. 10A and 10B show defibrillator displays that indicate to a rescuer levels of perfusion being obtained by chest compressions and decompressions that the rescuer is performing. FIG. 10A shows exemplary data displayed during the administration of CPR chest compressions and decompressions when the CPR quality is within acceptable ranges, while FIG. 10B shows modifications to the display when the CPR quality is outside of the acceptable range.

In the example shown in FIG. 10B, the rate of chest compressions and decompressions has dropped from 154 compressions and decompressions per minute (FIG. 10A) to 88 compressions and decompressions per minute. The defibrillator device determines that the compression rate of 88 compressions and decompressions per minute is below the acceptable range of greater than 100 compressions and decompressions per minute. In order to alert the user that the compression rate has fallen below the acceptable range, the defibrillator device provides a visual indication 1018 to emphasize the rate information. In this example, the visual indication 1018 is a highlighting of the rate information. Similar visual indications can be provided based on depth measurements when the depth of the compressions and decompressions is shallower or deeper than an acceptable range of depths. Also, when the change in rate or depth indicates that a rescuer is becoming fatigued, the system can display a message to switch who is performing the chest compressions and decompressions, and can also emit aural or haptic feedback to the same effect.

In the examples shown in FIGS. 10A and 10B, a perfusion performance indicator (PPI) 1016 provides additional information about the quality of chest compressions and decompressions during CPR treatment. The PPI 1016 includes a shape (e.g., a diamond) with the amount of fill in the shape differing based on the measured rate and depth of the compressions and decompressions. In FIG. 10A, the depth and rate fall within the acceptable ranges (e.g., at least 100 compressions and decompressions/minute (CPM) and the depth of each compression is greater than 40 mm) so the PPI indicator 1016a shows a fully filled shape. In contrast, in FIG. 10B, when the rate has fallen below the acceptable range, the amount of fill in the indicator 1016b is lessened such that only a portion of the indicator is filled. The partially filled PPI 1016b provides a visual indication of the quality of the CPR is below an acceptable range.

As noted above with respect to FIG. 6A, in addition to measuring information about the rate and depth of CPR chest compressions and decompressions, in some implementations the defibrillator provides information about the active decompression. For example, as a rescuer tires, the rescuer can begin leaning on the patient between chest compressions and decompressions such that the chest cavity is not able to fully expand at the end of a compression. If the rescuer does not properly perform (portions of) chest compressions and/or decompressions the quality of the CPR can diminish. As such, providing a visual or audio indication to the user when the user does not fully release can be beneficial. In addition, such factors can be included in a determination of whether the rescuer's performance has deteriorated to a level that the rescuer should be instructed to permit someone else perform the chest compressions and decompressions, and such information can be conveyed in the various manners discussed above.

Figure 11A:
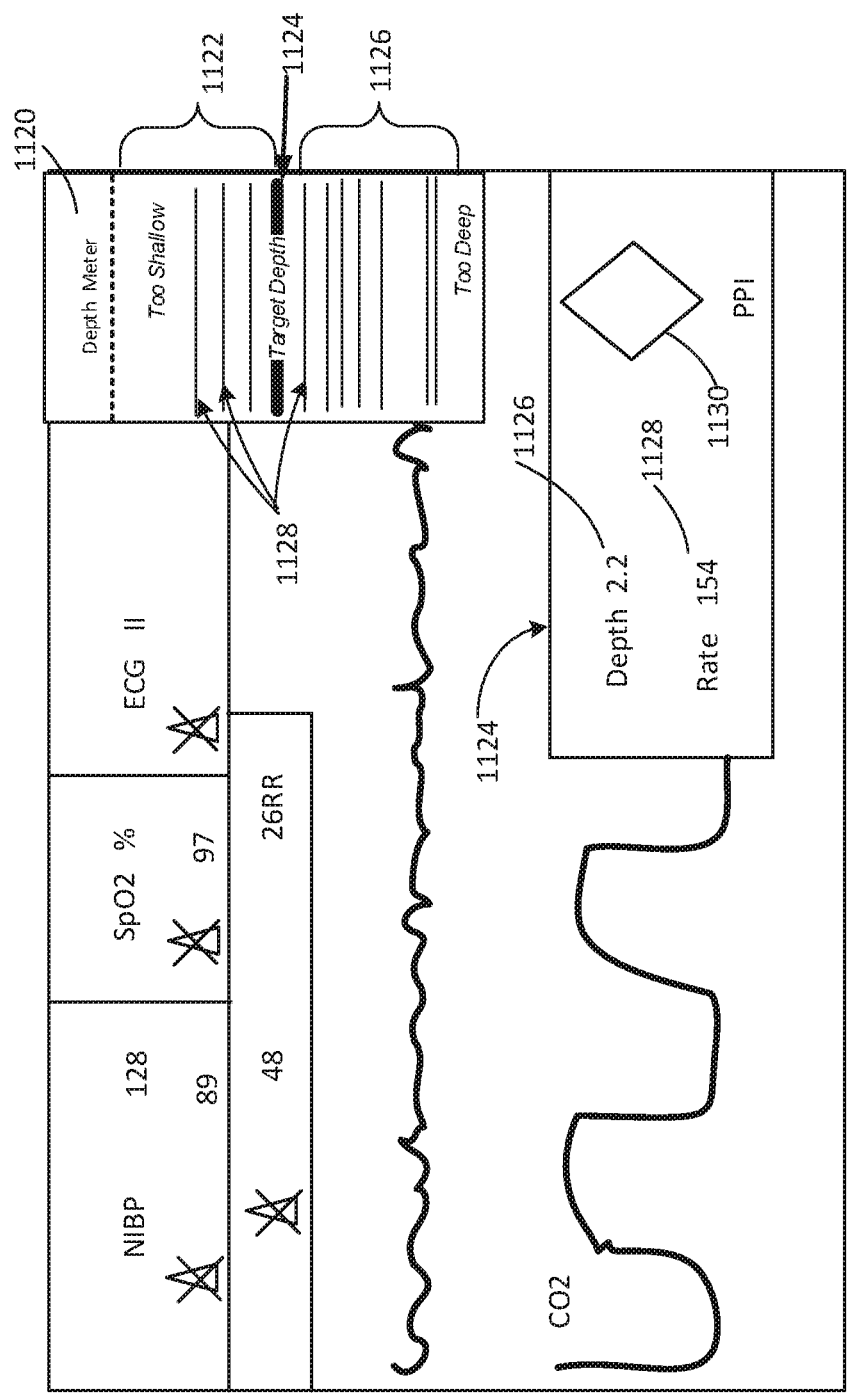
FIGS. 11A and 11B show screenshots with gradated scales indicating target chest compression depths.

As shown in FIG. 11A, a visual representation of CPR quality can include an indicator of CPR compression depth such as a CPR depth meter 1120. The CPR depth meter 1120 can be automatically displayed upon detection of CPR chest compressions and decompressions.

On the CPR depth meter 1120, depth bars 1128 visually indicate the depth of the administered CPR compressions and decompressions relative to a target depth 1124. As such, the relative location of the depth bars 1128 in relation to the target depth 1124 can serve as a guide to a rescuer for controlling the depth of CPR compressions and decompressions. For example, depth bars 1128 located in a region 1122 above the target depth bar 1124 indicate that the compressions and decompressions were shallower than the target depth, and depth bars 1128 located in a region 1126 below the target depth bar 1124 indicate that the compressions and decompressions were deeper than the target depth. Again, then depth is inadequate (along with perhaps other factors) for a sufficient time to indicate that the rescuer is fatiguing, an indicator to switch rescuers can be provided in the manners discussed above.

Figure 11B:
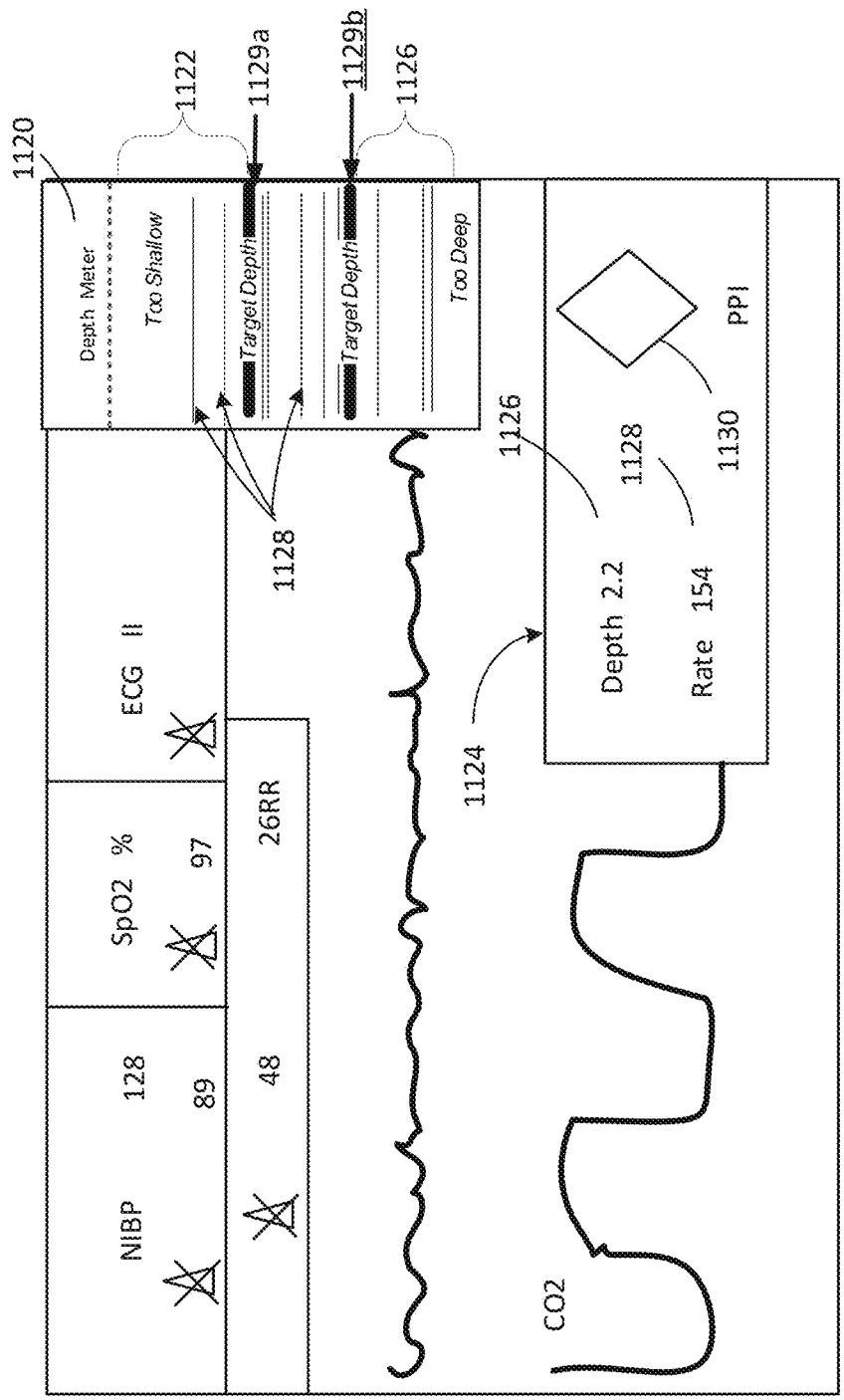

While the example shown in FIG. 11A displayed the target depth 1124 as a single bar, in some additional examples, the target depth can be displayed as a range of preferred depths. For example, two bars 1129a and 1129b can be included on the depth meter 1120 providing an acceptable range of compression depths (e.g., as shown in FIG. 11B) and an acceptable amplitude of decompression. Additionally, in some implementations, compressions and decompressions that have amplitudes outside of an acceptable range can be highlighted in a different color than compressions and decompressions that have depths within the acceptable range of compression depths.

The depth bars 1128 displayed on the CPR depth meter 1120 can represent the compression depths of the most recent CPR compressions and decompressions administered by the rescuer. For example, the CPR depth meter 1120 can display depth bars 1128 for the most recent 10-20 CPR compressions and decompressions (e.g., the most recent 10 CPR compressions and decompressions, the most recent 15 compressions and decompressions, the most recent 20 CPR compressions and decompressions). In another example, CPR depth meter 1120 can display depth bars 1128 for CPR compressions and decompressions administered during a particular time interval (e.g., the previous 10 seconds, the previous 20 seconds).

In some additional implementations, physiological information (e.g., physiological information such as end-tidal $CO_2$ information, arterial pressure information, volumetric $CO_2$, pulse oximetry (presence of amplitude of waveform possibly), and carotid blood flow (measured by Doppler) of the patient (and in some cases, the rescuer) can be used to provide feedback on the effectiveness of the CPR delivered at a particular target depth. Based on the physiological information, the system can automatically determine a target CPR compression depth (e.g., calculate or look-up a new CPR compression target depth) and, for example, provide feedback to a rescuer to increase or decrease the depth/rate of the CPR compressions and decompressions. Such feedback can include a sequence of desirable positions to guide the rescuer to adjust his/her body position and/or body motion to achieve a desirable combination of CPR compressions and decompressions (e.g., depth, rate), rescuer fatigue, and/or physiological outcome. Thus, the system can provide both feedback related to how consistently a rescuer is administering CPR compressions and decompressions at a target depth/rate, and feedback related to whether the target depth/rate should be adjusted based on measured physiological parameters, along with how the rescuer may enhance his/her body positioning in administering CPR treatment. If the rescuers do not respond to such feedback and continues performed sub-optimal CPR, the system can then display an additional message to switch out the person performing CPR chest compressions and decompressions.

In some implementations, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch or a centimeter and prompt the rescuer to increase or decrease the compression depth by the determined amount. For example, the system can adjust the target compression depth by 2.5-10 mm (e.g., 2.5 mm to 5 mm or about 5 mm) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, can determine whether to make further adjustments to the target compression depth.

And again, the actual performance of the rescuer against the revised target can be continually monitored to determine when the rescuer's performance has fallen below an acceptable level, so that the rescuer and perhaps others can be notified to change who is performing the chest compressions and decompressions. Also, each of the relevant parameters of patient condition discussed above with respect to the various screenshots can be made one of multiple inputs to a process for determining when rescuers who are performing one component of a rescue technique should be switched out with another rescuer, such as for reasons of apparent fatigue on the part of the first rescuer.

While at least some of the implementations described above describe techniques and displays used during manual human-delivered chest compressions and decompressions, similar techniques and displays can be used with automated chest compression devices such as the AUTOPULSE device manufactured by ZOLL Medical, MA.

Figure 12:
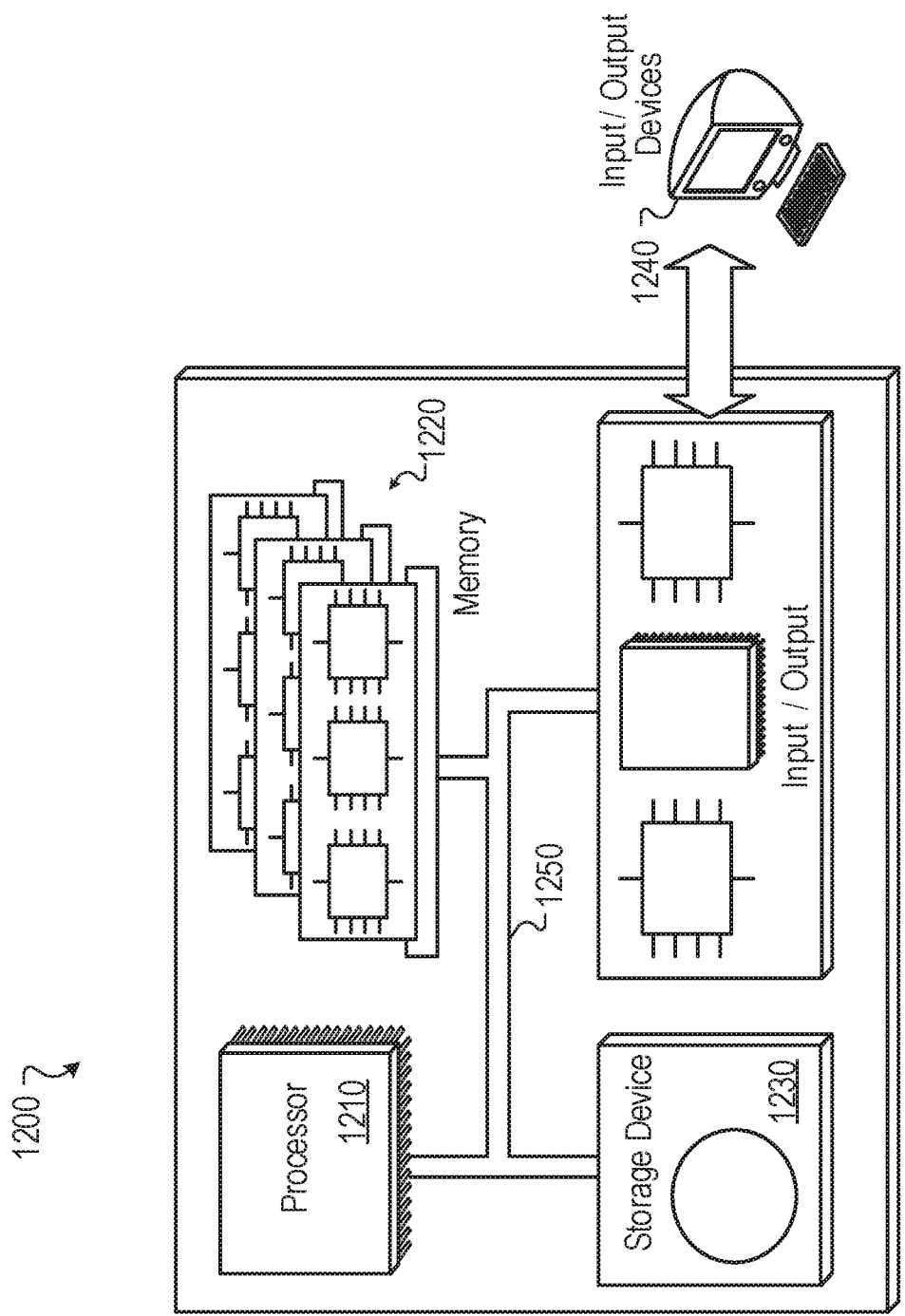
FIG. 12 shows a general computer system that can provide interactivity with a user of a medical device, such as feedback to a user in the performance of CPR treatment.

The described techniques can be assisted by the use of a computer-implemented medical device, such as a defibrillator that includes computing capability. Such defibrillator or other device is shown in FIG. 12, and can communicate with and/or incorporate a computer system 1200 in performing the operations discussed above, including operations for computing the quality of one or more components of CPR provided to a patient and generating feedback to rescuers, including feedback to change rescuers who are performing some components of the CPR treatment. The system 1250 can be implemented in various forms of digital computers, including computerized defibrillators laptops, personal digital assistants, tablets, and other appropriate computers. Additionally, the system can include portable storage media, such as, Universal Serial Bus (USB) flash drives. For example, the USB flash drives can store operating systems and other applications. The USB flash drives can include input/output components, such as a wireless transmitter or USB connector that can be inserted into a USB port of another computing device.

The system 1250 includes a processor 1210, a memory 1220, a storage device 1230, and an input/output device 1240. Each of the components 1210, 1220, 1230, and 1240 are interconnected using a system bus. The processor 1210 is capable of processing instructions for execution within the system 1250. The processor can be designed using any of a number of architectures. For example, the processor 1210 can be a CISC (Complex Instruction Set Computers) processor, a RISC (Reduced Instruction Set Computer) processor, or a MISC (Minimal Instruction Set Computer) processor.

In one implementation, the processor 1210 is a single-threaded processor. In another implementation, the processor 1210 is a multi-threaded processor. The processor 1210 is capable of processing instructions stored in the memory 1220 or on the storage device 1230 to display graphical information for a user interface on the input/output device 1240.

The memory 1220 stores information within the system 1250. In one implementation, the memory 1220 is a computer-readable medium. In one implementation, the memory 1220 is a volatile memory unit. In another implementation, the memory 1220 is a non-volatile memory unit.

The storage device 1230 is capable of providing mass storage for the system 1250. In one implementation, the storage device 1230 is a computer-readable medium. In various different implementations, the storage device 1230 can be a floppy disk device, a hard disk device, an optical disk device, or a tape device.

The input/output device 1240 provides input/output operations for the system 1250. In one implementation, the input/output device 1240 includes a keyboard and/or pointing device. In another implementation, the input/output device 1240 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described can be employed, and can be encompassed by the following claims.

What is claimed is:

1. A system for assisting in administration of cardiopulmonary resuscitation (CPR) treatment to a patient in need of emergency assistance, the system comprising:
   an adhesive pad configured to be adhered to at least a portion of a patient's chest;
   a sensor configured to be placed on the patient's chest and to measure at least one chest compression parameter during CPR treatment; and
   a landing pad having a coupling surface configured to maintain adherence with an applicator body of an active compression decompression device, the adherence with the applicator body being sufficient to transfer a decompression force between the active compression decompression device and at least the portion of the patient's chest during the CPR treatment, wherein the landing pad comprises a lower portion configured to be adhered to the portion of the patient's chest and having a material extended around a perimeter of an opening located at a central region of the landing pad and adapted to form a seal between the portion of the patient's chest and at least one of the adhesive pad and the sensor.

2. The system of claim 1; wherein the adhesive pad comprises an electrode configured to transmit a defibrillation current to the patient.

3. The system of claim 1, wherein the material comprises silicone gel.

4. The system of claim 1, wherein the lower portion of the landing pad comprises an adhesive for adhering the landing pad to the portion of the patient's chest.

5. The system of claim 1, wherein the coupling surface comprises a surface that complements at least one suction cup.

6. The system of claim 1, wherein the coupling surface comprises a compliant material that comprises a foam sheet and is smooth.

7. The system of claim 1, wherein the landing pad comprises a lower portion configured to be adhered to the portion of the patient's chest, the lower portion comprising wings that are constructed and arranged to flex away from the coupling surface of the landing pad to maintain adherence with the portion of the patient's chest during the administration of active compression decompression.

8. The system of claim 1, wherein the landing pad comprises an upper portion comprising the coupling surface, wherein the upper portion comprises at least one barrier extending along an outer boundary of the landing pad.

9. The system of claim 1, comprising at least one wire coupled to the sensor for providing electrical connection between the sensor and a medical device.

10. The system of claim 9, wherein the coupling surface covers the at least one wire.

11. The system of claim 1, wherein the sensor is coupled to the adhesive pad.

12. The system of claim 1, wherein the coupling surface of the landing pad at least partially surrounds the sensor.

13. The system of claim 1, wherein the landing pad includes a lower portion configured to be adhered to the patient's chest and having a gel material that forms a seal between the patient's chest and at least one of the adhesive pad and the sensor.

14. The system of claim 1, comprising a passageway located between the sensor and the coupling surface.

15. The system of claim 14, wherein the passageway encircles the sensor.

16. The system of claim 14, wherein the passageway comprises a gap between the sensor and the coupling surface.

17. The system of claim 14, wherein the passageway comprises at least one filter.

18. The system of claim 14, wherein upon adherence between the coupling surface and the active compression decompression device, the applicator body of the active compression decompression device surrounds the passageway.

19. The system of claim 14, wherein the passageway has a donut shape.

20. The system of claim 14, wherein the passageway has an oval shape.

21. The system of claim 14, wherein the passageway is aligned with a geometrical center of the active compression decompression device.

22. The system of claim 1, wherein the coupling surface comprises a mechanical attachment member complementary to a corresponding attachment member of the active compression decompression device.

23. The system of claim 22, wherein the mechanical attachment member comprises a mating interface.

24. An apparatus for assisting active compression decompression cardiopulmonary resuscitation (CPR) treatment to a patient in need of emergency assistance, the apparatus comprising:
   a landing pad comprising an upper portion and a lower portion mechanically, coupled to one another,
   wherein the lower portion is configured to be adhered to at least a portion of a patient's chest and comprises a material extended around a perimeter of an opening located at a central region of the landing pad and adapted to form a seal between the portion of the patient's chest and a component located between the portion of the patient's chest and the lower portion of the landing pad, and
   wherein the upper portion comprises a coupling surface configured to maintain adherence with an applicator body of an active compression decompression device, the adherence with the applicator body being sufficient to transfer a decompression force between the active compression decompression device and the portion of the patient's chest during the CPR treatment.

25. The apparatus of claim 24, wherein the coupling surface is smooth and complements at least one suction cup.

26. The apparatus of claim 24, wherein the coupling surface comprises a compliant material.

27. The apparatus of claim 26, wherein the compliant material comprises a foam sheet.

28. The apparatus of claim 26, wherein the compliant material comprises a foam sheet.

29. The apparatus of claim 24, wherein the upper portion of the landing pad comprises at least one barrier extending along an outer boundary of the landing pad.

30. The apparatus of claim 24, wherein the upper portion of the landing pad comprises a top layer and the lower portion of the landing pad comprises a bottom layer, the landing pad further comprising a middle layer that is more rigid than the top layer and the bottom layer.

31. The apparatus of claim 24, wherein the material comprises silicone gel.

32. The apparatus of claim 24, wherein the lower portion of the landing pad has an outer boundary comprising recessed segments.

33. The apparatus of claim 24, wherein the lower portion of the landing pad comprises wings that are constructed and arranged to flex away from the upper portion of the landing pad to maintain adherence with the portion of the patient's chest during the administration of active compression decompression.

34. The apparatus of claim 24, wherein the lower portion of the landing pad comprises an adhesive for adhering the landing pad to the portion of the patient's chest.

* * * * *

UNITED STATES PATENT AND TRADEMARK OFFICE
CERTIFICATE OF CORRECTION

PATENT NO. : 10,780,020 B2
APPLICATION NO. : 15/721101
DATED : September 22, 2020
INVENTOR(S) : Scott Edward Hunt et al.

Page 1 of 1

It is certified that error appears in the above-identified patent and that said Letters Patent is hereby corrected as shown below:

In the Claims

Column 33, Line 13, Claim 2, delete "1;" and insert -- 1, --.

Column 34, Line 18, Claim 24, delete "mechanically," and insert -- mechanically --.

Signed and Sealed this
First Day of December, 2020

Andrei Iancu
*Director of the United States Patent and Trademark Office*